United States Patent
Kawanishi et al.

(10) Patent No.: US 7,851,130 B2
(45) Date of Patent: *Dec. 14, 2010

(54) PHOTOSENSITIVE COMPOSITION, COMPOUND FOR USE IN THE PHOTOSENSITIVE COMPOSITION, AND PATTERN-FORMING METHOD USING THE PHOTOSENSITIVE COMPOSITION

(75) Inventors: Yasutomo Kawanishi, Ashigarakami-gun (JP); Kenji Wada, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 42 days.

This patent is subject to a terminal disclaimer.

(21) Appl. No.: 11/857,645

(22) Filed: Sep. 19, 2007

(65) Prior Publication Data

US 2008/0081288 A1  Apr. 3, 2008

(30) Foreign Application Priority Data

Sep. 19, 2006  (JP)  ............................ 2006-253381

(51) Int. Cl.
*G03F 7/038* (2006.01)
*G03F 7/039* (2006.01)
*G03F 7/20* (2006.01)
*G03F 7/30* (2006.01)
*C07D 497/00* (2006.01)

(52) U.S. Cl. .................... 430/270.1; 430/922; 430/325; 430/326; 430/942; 430/966; 549/26; 549/16; 549/17; 549/20

(58) Field of Classification Search ........................ None
See application file for complete search history.

(56) References Cited

U.S. PATENT DOCUMENTS

| 6,680,157 B1 | 1/2004 | Fedynyshyn |  |
|---|---|---|---|
| 2006/0210919 A1* | 9/2006 | Mizutani et al. | 430/270.1 |
| 2007/0072117 A1* | 3/2007 | Mizutani et al. | 430/270.1 |

FOREIGN PATENT DOCUMENTS

| EP | 1480078 A1 | 5/2004 |  |
| EP | 1 693 705 A2 | * | 8/2006 |
| EP | 1 703 326 A2 | * | 9/2006 |
| EP | 1 767 991 A2 | * | 3/2007 |
| JP | 6-41221 A | | 2/1994 |
| JP | 2000-122291 A | | 4/2000 |
| JP | 3173368 B2 | | 3/2001 |
| JP | 2001-114825 A | | 4/2001 |
| JP | 2001-206917 A | | 7/2001 |
| JP | 2002-323768 A | | 11/2002 |
| JP | 2003-149800 A | | 5/2003 |
| JP | 3549592 B2 | | 4/2004 |
| JP | 2006-276759 | * | 10/2006 |

OTHER PUBLICATIONS

Machine-assisted English translation of JP2006-276759 provided by JPO.*

* cited by examiner

*Primary Examiner*—Sin J. Lee
(74) *Attorney, Agent, or Firm*—Sughrue Mion, PLLC

(57) ABSTRACT

A photosensitive composition includes (A) a compound represented by the following formula (I):

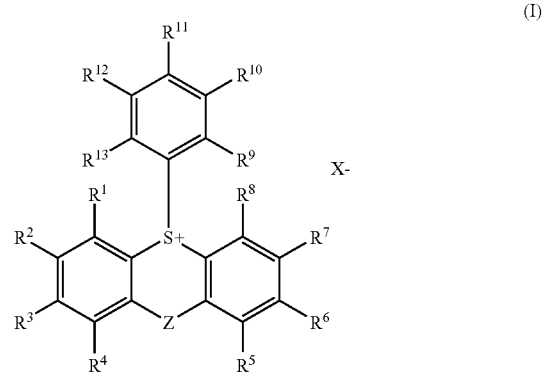

wherein $R^1$ to $R^{13}$ each independently represents a hydrogen atom or a substituent, Z represents a single bond or a divalent linking group, and $X^-$ represents an anion containing a proton acceptor functional group.

16 Claims, 1 Drawing Sheet

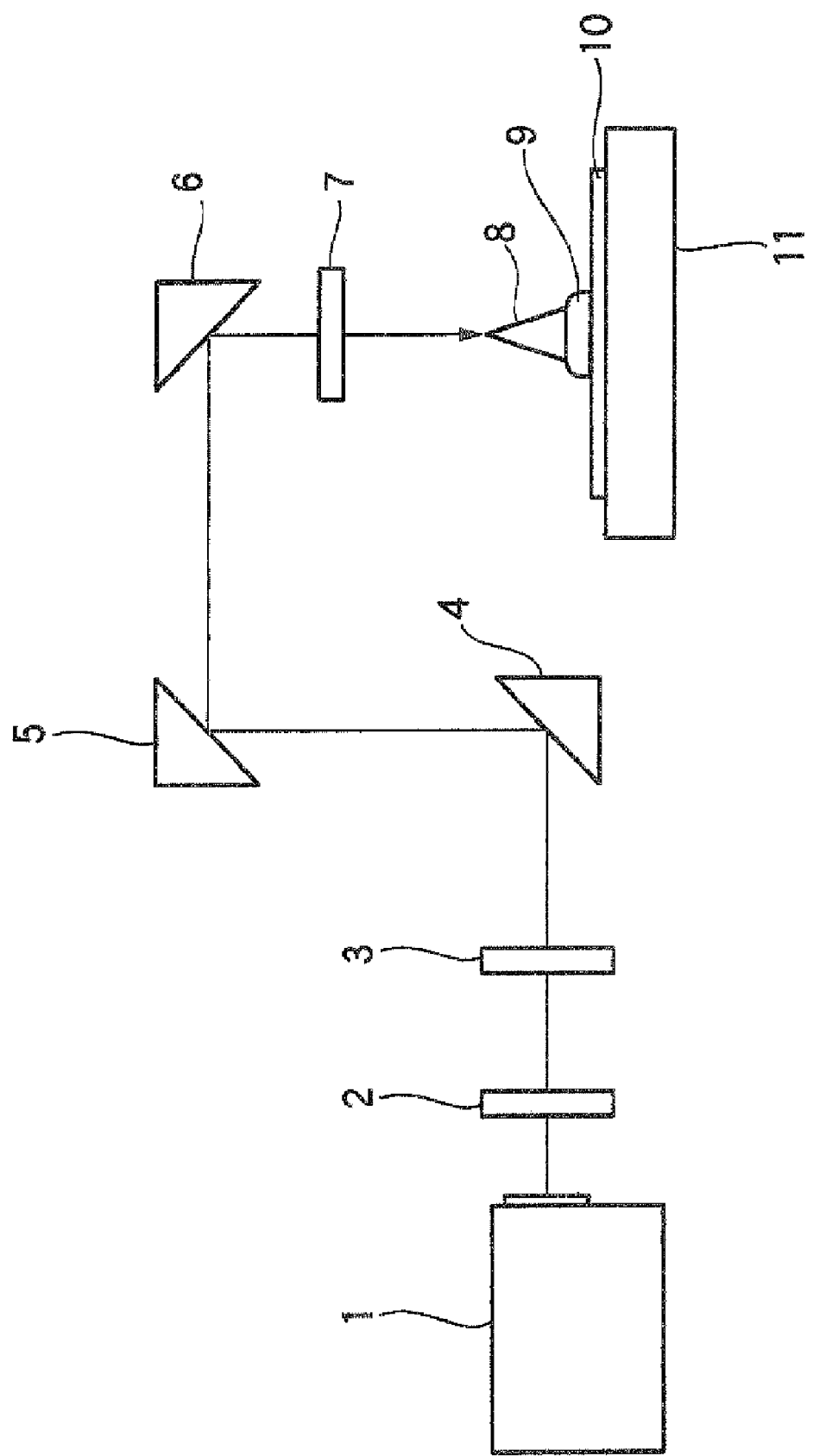

PHOTOSENSITIVE COMPOSITION, COMPOUND FOR USE IN THE PHOTOSENSITIVE COMPOSITION, AND PATTERN-FORMING METHOD USING THE PHOTOSENSITIVE COMPOSITION

BACKGROUND OF THE INVENTION

1. Field of the Invention

The present invention relates to a photosensitive composition preferably used in super-microlithography processes such as the manufacture of super LSI and high capacity microchips, and other photo-publication processes. More specifically, the invention relates to a positive photoresist capable of forming a highly refined pattern with electron beams, X-rays or EUV rays, and a resist composition suitable for fine processing of semiconductor devices using electron beams, X-rays or EUV rays (wavelength: 13 nm or so).

2. Description of the Related Art

In the manufacturing process of semiconductor devices such as IC and LSI, fine processing by lithography using photoresist compositions has been conventionally carried out. In recent years, with the increment of integration of integrated circuits, ultrafine pattern formation of the levels of a sub-micron and quarter-micron has come to be required. Under such a circumstance, the exposure wavelengths show a tendency to be shortening, such as from g-ray to i-ray, further to KrF excimer laser beam. Further, lithography using electron beams, X-rays or EUV rays in addition to excimer laser beams has been developed nowadays.

In particular, electron beam lithography is taken as the pattern forming technique of the next generation or the next of the next generation, so that resists of high sensitivity and high resolution are required. The increase in sensitivity is very important object in view of shortening of the processing time of wafers, but in positive resists for electron beams, pursuit of increment of sensitivity is accompanied by not only reduction of resolution but also deterioration of line edge roughness, so that the development of a resist satisfying these characteristics at the same time is strongly desired. Here, line edge roughness means that the edge of the interface between the line pattern of a resist and a substrate irregularly changes in perpendicular direction to the line direction attributable to the characteristics of the resist, and the edge looks unevenly when it is observed from right above. This unevenness is transferred to the substrate by etching processing with the resist as a mask and deteriorates electric characteristic and results in the reduction of yield. In particular, line edge roughness is an extremely important object to be solved in a hyperfine region of 0.25 µm or less. High sensitivity, high resolution, a good pattern form and good line edge roughness are in relationship of trade-off, and how to satisfy these factors at the same time is a very important object.

Further, when EUV is used as the light source, since wavelengths of the lights belong to the extreme ultraviolet region having high energy, there is a problem of contrast reduction due to concentration of photochemical reaction such as the tendency to be negative attributable to EUV rays and the like. In lithography using X-rays or EUV rays, it is also an important object to reconcile high sensitivity and high resolution, and the resolution of this problem is indispensable.

As the resist suitable for lithographic process using electron beams, X-rays or EUV rays, chemical amplification resists utilizing acid catalytic reaction are mainly used from the viewpoint of the enhancement of sensitivity, and in positive resists, phenolic polymers having properties that are insoluble or hardly soluble in an alkali developing solution but become soluble in an alkali developing solution by the action of an acid (hereinafter referred to as phenolic acid-decomposable resin), and chemical amplification resist compositions comprising acid generators are effectively used as the main components.

In connection with these positive resists for electron beams, X-rays or EUV rays, some resist compositions containing phenolic acid-decomposable resin are known (e.g., JP-A-2002-323768 (The term "JP-A" as used herein refers to an "unexamined published Japanese patent application".), JP-A-6-41221, Japanese Patent No. 3173368, JP-A-2000-122291, JP-A-2001-114825, and JP-A-2001-206917).

Further, when light sources such as electron beams, X-rays and EUV are used, exposure is carried out under a vacuum, so that compounds having a low boiling point such as solvents and resist materials decomposed by high energy are volatilized to thereby contaminate the exposure apparatus, i.e., outgassing is a serious problem. In recent years, various investigations are in progress on the reduction of outgassing, and a variety of trials are suggested, e.g., restraint of volatilization of low molecular weight compounds by forming a top coat layer (e.g., refer to EP 1480078), and addition of a radical trapping agent capable of inhibiting decomposition of a polymer (e.g., refer to U.S. Pat. No. 6,680,157). Some contrivances of outgassing are also required in connection with acid generators.

In addition, contrivances such as linking of a benzene ring of triphenyl sulfonium (JP-A-2003-149800), and addition of a base capable of decomposing and becoming a neutral compound by actinic radiation exposure (Japanese Patent No. 3549592) have been tried.

However, it is the present situation that high sensitivity, high resolution, good line edge roughness and low outgassing in a hyperfine region cannot be satisfied at the same time with any of these combinations.

SUMMARY OF THE INVENTION

An object of the invention is to solve the problems of the improving technique of performances in fine processing of semiconductor devices using high energy rays, X-rays, electron beams or EUV rays, and another object is to provide a photosensitive composition capable of satisfying high sensitivity, high resolution, good line edge roughness and low outgassing at the same time.

As a result of eager examinations, the present inventors have found that the above objects of the invention can be achieved surprisingly with a photosensitive composition containing specific compound (A).

That is, the invention can be achieved by the following constitutions.

(1) A photosensitive composition comprising:

(A) a compound represented by the following formula (I):

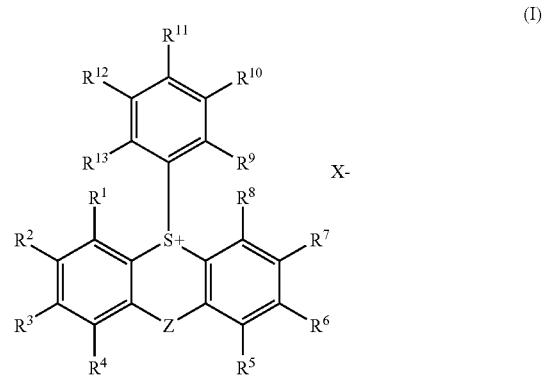

wherein $R^1$ to $R^{13}$ each independently represents a hydrogen atom or a substituent;

Z represents a single bond or a divalent linking group; and

X⁻ represents an anion containing a proton acceptor functional group.

(2) The photosensitive composition as described in (1), further comprising:

(B) a compound which generates an acid by decomposition of the compound upon irradiation with an actinic ray or radiation.

(3) The photosensitive composition as described in (1), further comprising:

(C) a resin, of which a solubility in an alkali developing solution increases by decomposition of the resin by action of an acid.

(4) The photosensitive composition as described in (1), further comprising:

(D) a resin which is soluble in an alkali developing solution; and (E) an acid crosslinking agent which crosslinks with the resin (D) by action of an acid.

(5) The photosensitive composition as described in (3), wherein the resin (C) contains at least one of an alicyclic structure and an aromatic cyclic structure.

(6) The photosensitive composition as described in (1), further comprising:

(F) a basic compound.

(7) The photosensitive composition as described in (1), further comprising:

(G) at least one of a fluorine surfactant and a silicon surfactant.

(8) The photosensitive composition as described in (2), wherein the compound (B) is a sulfonium compound.

(9) The photosensitive composition as described in (2), wherein the compound (B) contains a sulfonate anion.

(10) The photosensitive composition as described in (1), further comprising:

a solvent.

(11) The photosensitive composition as described in (10), wherein the solvent comprises a propylene glycol monomethyl ether acetate.

(12) The photosensitive composition as described in (11), wherein the solvent further comprises a propylene glycol monomethyl ether.

(13) The photosensitive composition as described in (1), which is exposed with X-rays, electron beams or EUV.

(14) A pattern forming method comprising:

a processes of forming a photosensitive film with the photosensitive composition as described in (1);

a process of exposing the photosensitive film; and a process of developing the photosensitive film.

(15) A compound represented by the following formula (I):

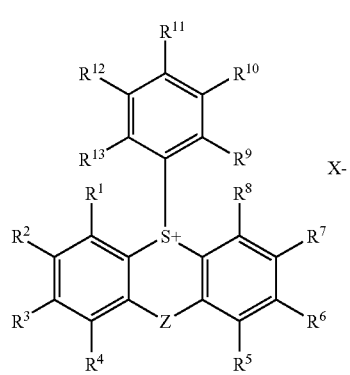

wherein $R^1$ to $R^{13}$ each independently represents a hydrogen atom or a substituent;

Z represents a single bond or a divalent linking group; and

X⁻ represents an anion containing a proton acceptor functional group.

BRIEF DESCRIPTION OF THE DRAWING

The drawing schematically illustrates a laboratory apparatus of two-beam interference exposure, wherein 1 denotes Laser, 2 denotes Diaphragm, 3 denotes Shutter, 4, 5 and 6 denote Reflection mirrors, 7 denotes Condenser lens, 8 denotes Prism, 9 denotes Immersion liquid, 10 denotes Wafer having an antireflection film and a resist film, and 11 denotes Wafer stage.

DETAILED DESCRIPTION OF THE INVENTION

The compound for use in the invention will be described in detail below.

In the description of a group (an atomic group) in the specification of the invention, the description not referring to substitution or unsubstitution includes both a group not having a substituent and a group having a substituent. For example, "an alkyl group" includes not only an alkyl group having no substituent (an unsubstituted alkyl group) but also an alkyl group having a substituent (a substituted alkyl group).

The invention is based on the finding of novel compound (A) represented by formula (I) useful for a photosensitive composition.

The photosensitive composition containing compound (A) may be either a positive or negative photosensitive composition.

The positive photosensitive composition in the invention, more preferably a positive resist composition, contains, in addition to compound (A), acid generator (B), and resin (C) capable of decomposing by the action of an acid to increase solubility in an alkali developing solution, and further, if necessary, a dissolution inhibiting compound having a molecular weight of 3,000 or less that is capable of decomposing by the action of an acid to increase solubility in an alkali developing solution.

The negative photosensitive composition in the invention, more preferably a negative resist composition, contains, in addition to compound (A), acid generator (B), resin (D) soluble in an alkali developing solution, and acid crosslinking agent (E) capable of crosslinking with the resin soluble in an alkali developing solution by the action of an acid.

Compound (A):

Compound (A) contained in the photosensitive composition in the invention will be described below.

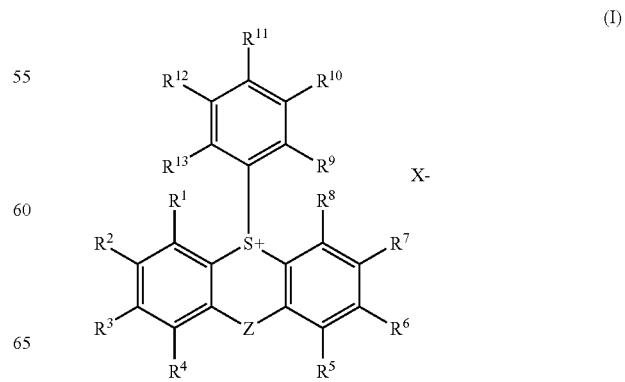

In formula (I), $R^1$ to $R^{13}$ each represents a hydrogen atom or a substituent; Z represents a single bond or a divalent linking group; and $X^-$ represents an anion containing a proton acceptor functional group.

$R^1$ to $R^{13}$ each represents a hydrogen atom or a substituent, and the substituent is not especially restricted and any one can be used, e.g., a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group, a cyano group, a nitro group, a carboxyl group, an alkoxyl group, an aryloxy group, a silyloxy group, a heterocyclic oxy group, an acyloxy group, a carbamoyloxy group, an alkoxycarbonyloxy group, an aryloxycarbonyloxy group, an amino (including an anilino group, an acylamino group, an aminocarbonylamino group, an alkoxycarbonylamino group, an aryloxycarbonylamino group, a sulfamoylamino group, an alkylsulfonylamino group, an arylsulfonylamino group, and a phosphinylamino group), an ammonio group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxy-carbonyl group, a carbamoyl group, an arylazo group, a heterocyclic azo group, an imido group, a phosphino group, a phosphinyl group, a phosphinyloxy group, a phosphono group, a silyl group, a hydrazino group, a ureido group, a boronic acid group ($-B(OH)_2$), a phosphato group ($-OPO(OH)_2$), a sulfato group ($-OSO_3H$), and other known substituents are exemplified.

Further, contiguous two of $R^1$ to $R^{13}$ can also form a ring together. As the rings to be formed, for example, aromatic or non-aromatic hydrocarbon rings, and heterocyclic rings are exemplified, and these rings can further form polycyclic condensed rings by combination. For example, a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxthine ring, a phenothiazine ring, and a phenazine ring are exemplified.

$R^1$ to $R^{13}$ each preferably represents a hydrogen atom, a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a cyano group, a carboxyl group, an alkoxyl group, an aryloxy group, an acyloxy group, a carbamoyloxy group, an acylamino group, an amino-carbonylamino group, an alkoxycarbonylamino group, an aryloxycarbonylamino group, a sulfamoylamino group, an alkyl-sulfonylamino group, an arylsulfonylamino group, an alkylthio group, an arylthio group, a sulfamoyl group, an alkylsulfonyl group, an arylsulfonyl group, an aryloxycarbonyl group, an alkoxycarbonyl group, a carbamoyl group, an imido group, a silyl group, or a ureido group.

$R^1$ to $R^{13}$ each more preferably represents a hydrogen atom, a halogen atom, an alkyl group (including a cycloalkyl group, a bicycloalkyl group, and a tricycloalkyl group), a cyano group, an alkoxyl group, an acyloxy group, an acylamino group, an aminocarbonylamino group, an alkoxycarbonylamino group, an alkylsulfonylamino group, an arylsulfonylamino group, an alkylthio group, a sulfamoyl group, an alkylsulfonyl group, an arylsulfonyl group, an alkoxycarbonyl group, or a carbamoyl group.

$R^1$ to $R^{13}$ each especially preferably represents a hydrogen atom, an alkyl group (including a cycloalkyl group, a bicycloalkyl group, and a tricycloalkyl group), a halogen atom, or an alkoxyl group.

Z represents a single bond or a divalent linking group, and as the divalent linking group, e.g., an alkylene group, an arylene group, a carbonyl group, a sulfonyl group, a carbonyloxy group, a carbonylamino group, a sulfonylamido group, an ether group, a thioether group, an amino group, a disulfide group, an acyl group, an alkylsulfonyl group, $-CH=CH-$, $-C\equiv C-$, an aminocarbonylamino group, and an aminosulfonylamino group are exemplified, which groups may have a substituent. As the substituents of these groups, the same substituents as described in $R^1$ to $R^{13}$ are exemplified. Z preferably represents a carbonyl group, a sulfonyl group, $-CH=CH-$, or $-C\equiv C-$, more preferably a sulfonyl group or a single bond, and still more preferably a single bond.

In view of the reduction of outgassing, the boiling point of a compound represented by the following formula (II) that is generated by decomposition of compound (I) is preferably 160° C. or more per 1 atm., more preferably 180° C. or more per 1 atm., and especially preferably 200° C. or more per 1 atm.

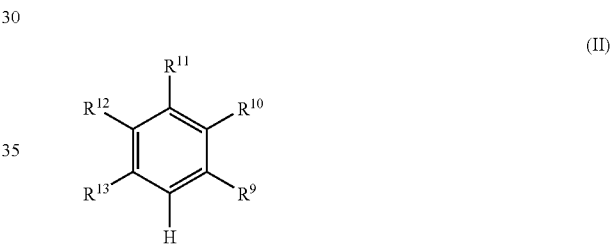

(II)

In formula (II), $R^9$ to $R^{13}$ each represents a hydrogen atom or a substituent, and specifically the same substituents as described in formula (I) are exemplified.

$X^-$ represents an anion containing a proton acceptor functional group. The proton acceptor functional group here represents a functional group having a conjugate base of an acid weaker than a sulfonic acid (an anion obtained by taking off a proton from an acid) or having basicity.

When $X^-$ contains a functional group having a conjugate base of an acid weaker than a sulfonic acid, as the proton acceptor functional group contained in $X^-$, a carboxylate anion, a phenoxy anion, and a hydroxy anion are exemplified, and preferably a carboxylate anion.

When $X^-$ contains a functional group having a conjugate base of an acid weaker than a sulfonic acid, as the proton acceptor functional group contained in $X^-$, a formate anion, an acetate anion, a propionate anion, a butanoate anion, a pentanoate anion, a hexanoate anion, a benzoate anion, a p-methylbenzoate anion, a phenoxy anion, a p-methylphenoxy anion, a naphthoxy anion, and a hydroxyl anion are specifically exemplified, and preferably an acetate anion, a propionate anion and a benzoate anion.

When $X^-$ contains a functional group having basicity, as the basic functional group, an amino group, an anilino group, a pyridino group, an amidino group, and a guanidino group are exemplified, and preferably an amino group and an anilino group.

When X⁻ contains a functional group having basicity, the anion is preferably strongly acidic, specifically a sulfonate anion, a disulfonamide anion, and a trisulfoncarbo anion are exemplified, and preferably a disulfonamide anion.

The content of compound (A) is preferably from 0.01 to 20 mass % based on all the solids content of the composition, more preferably from 0.5 to 10 mass %, and still more preferably from 1 to 7 mass %.

Compound (A) can be synthesized by synthesizing a known cyclic triphenylsulfonium compound, and then performing salt exchange by using ion chromatographic column or by the difference in solubility. Specifically, when Z in formula (I) represents a single bond, compound (A) is synthesized as follows: dibenzothiophene is made sulfoxide with aqueous hydrogen peroxide, the resulting sulfoxide is dissolved in a mixed solvent of methanesulfonic acid and phosphoric anhydride, further a benzene compound that may have a substituent is added thereto and they are reacted at from room temperature to 80° C. to make S-phenyldibenzothiophenium salt, and anion X is changed to a proton accepting anion. When Z represents a linking group having a hetero atom, compound (A) can also be synthesized according to fundamentally the same method.

The specific examples of compound (A) are shown below, but the invention is not restricted to these compounds.

(A1)
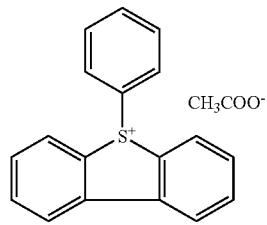

(A2)
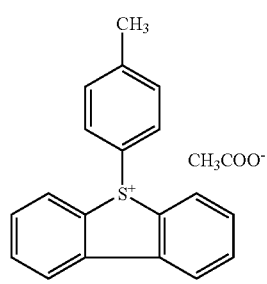

(A3)
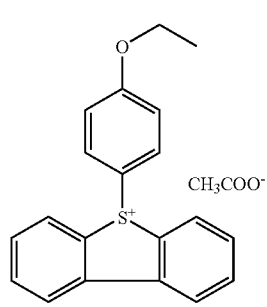

(A4)
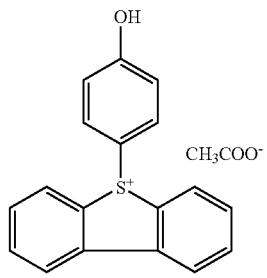

(A5)
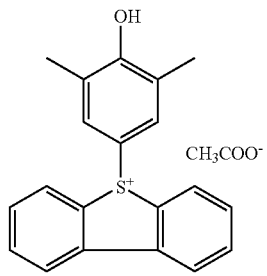

(A6)
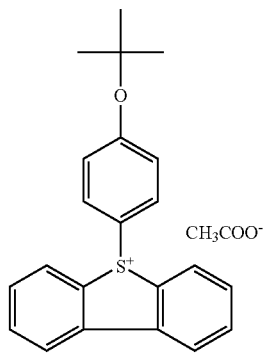

(A7)
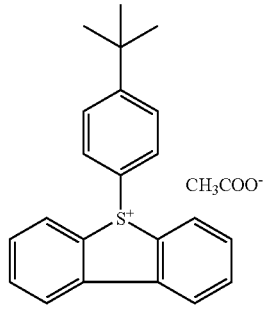

(A8)
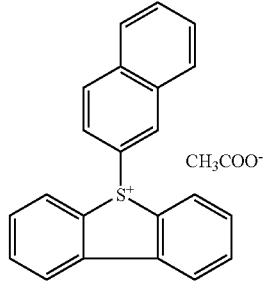

-continued
(A9)
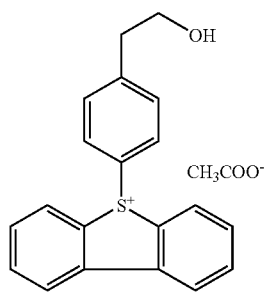
(A10)
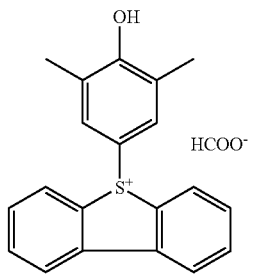
(A11)
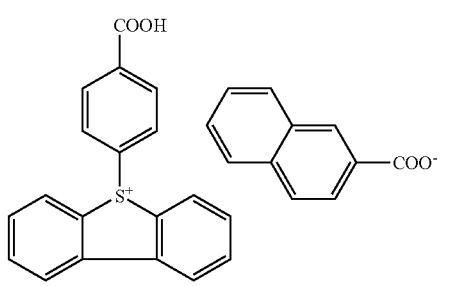
(A12)
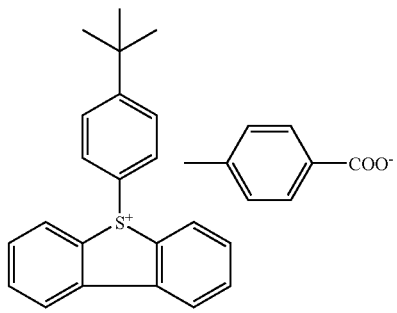
(A13)
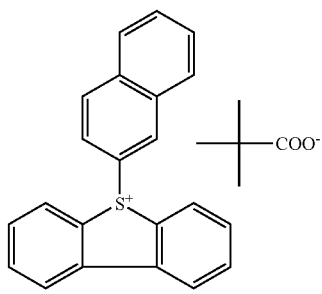
-continued
(A14)
(A15)
(A16)
(A17)
(A18)
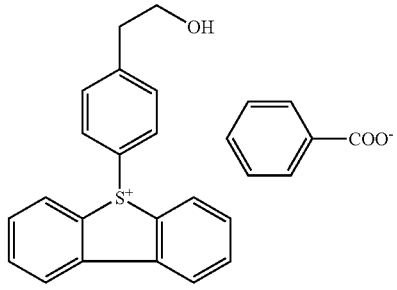

-continued
(A19)
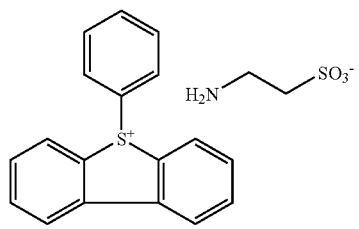
(A20)
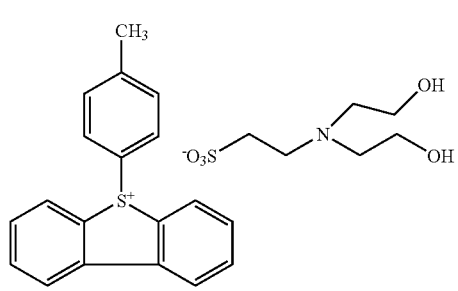
(A21)
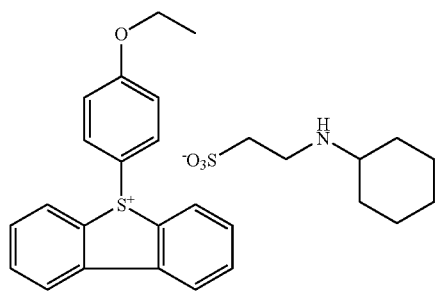
(A22)
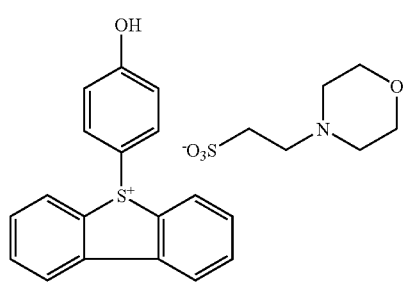
(A23)
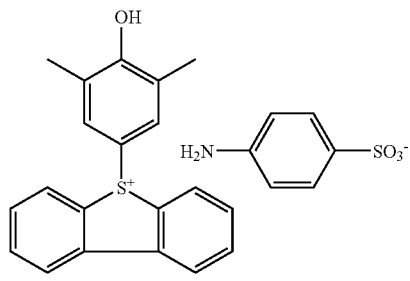
-continued
(A24)
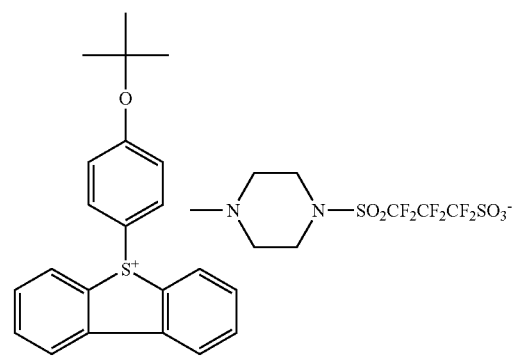
(A25)
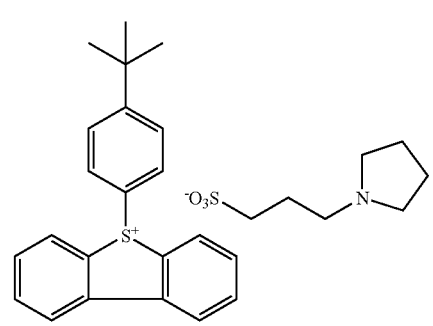
(A26)
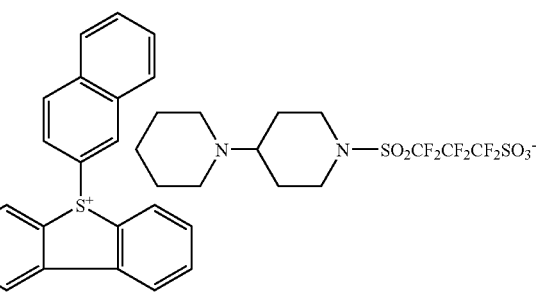
(A27)
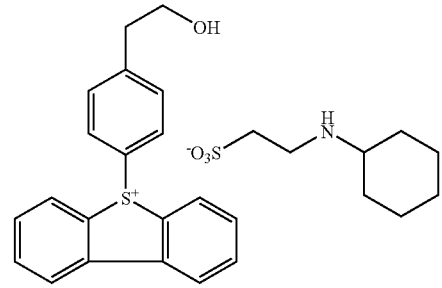
(A28)
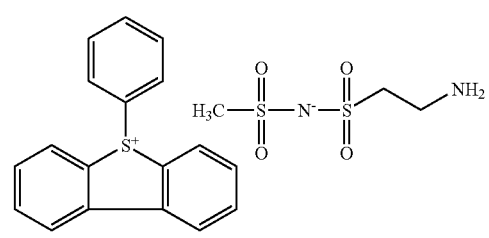

(A29) 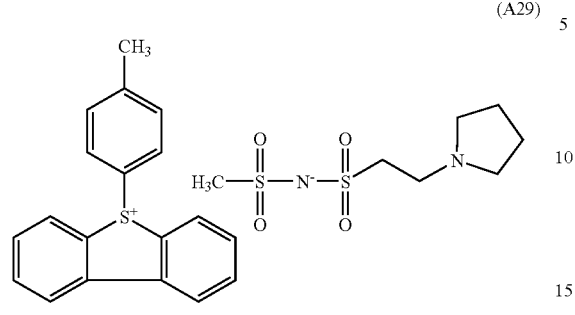
(A30) 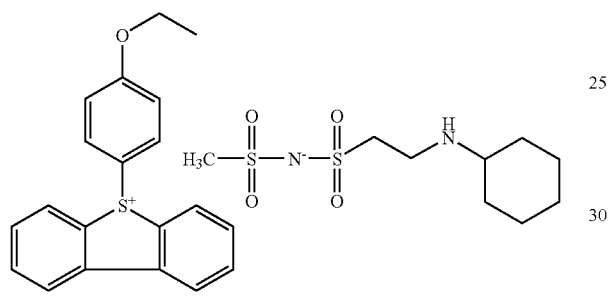
(A31) 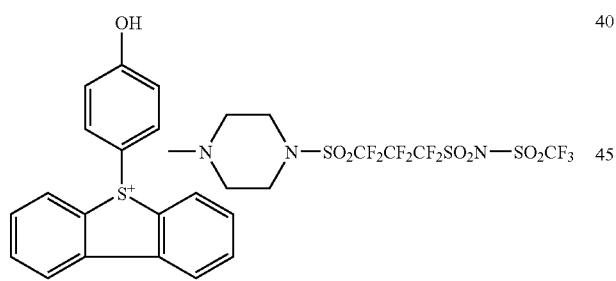
(A32) 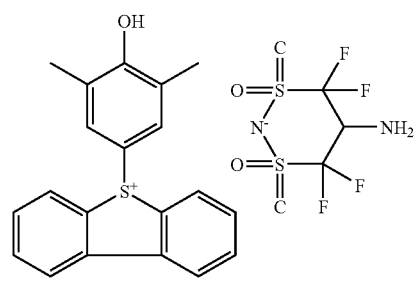
(A33) 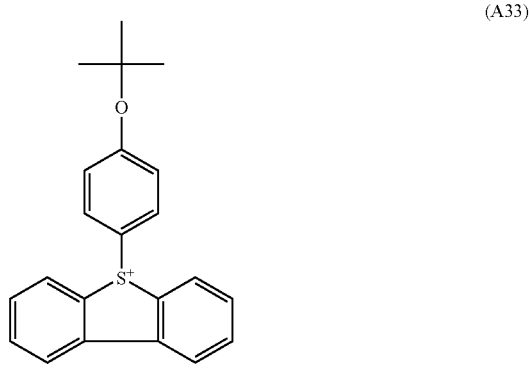
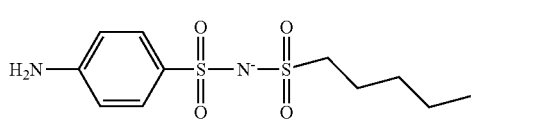
(A34) 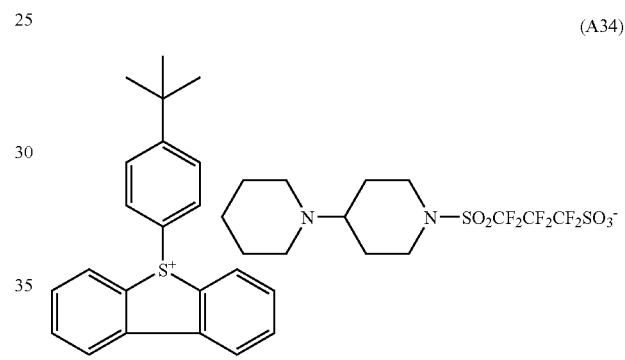
(A35) 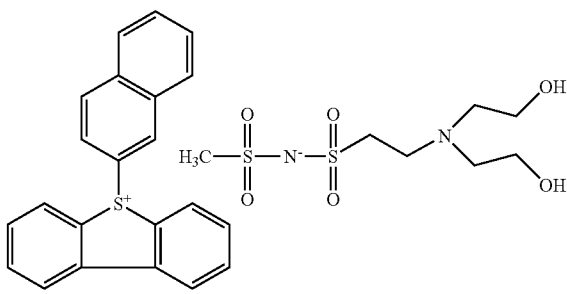
(A36) 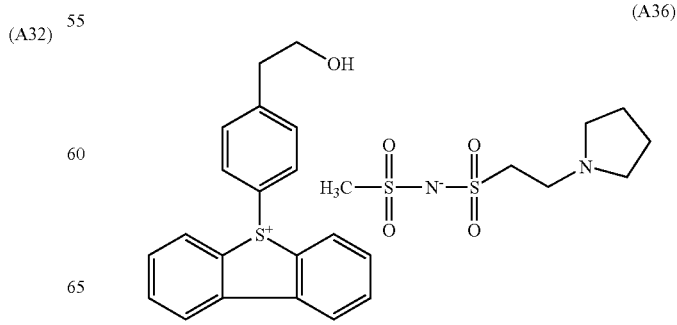

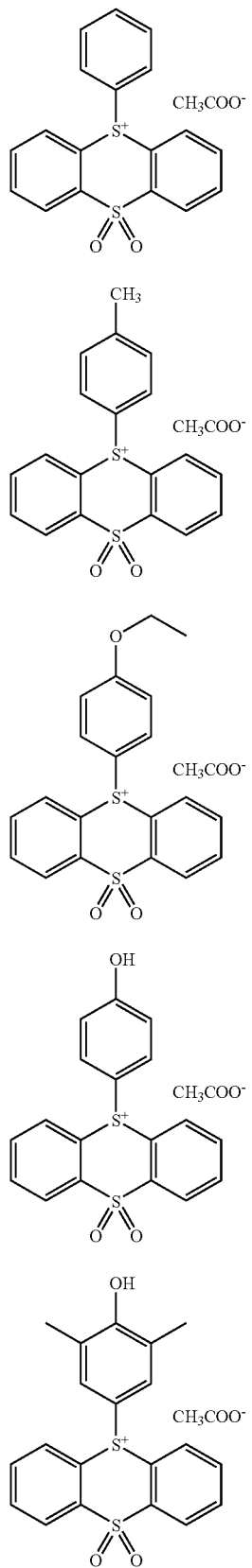
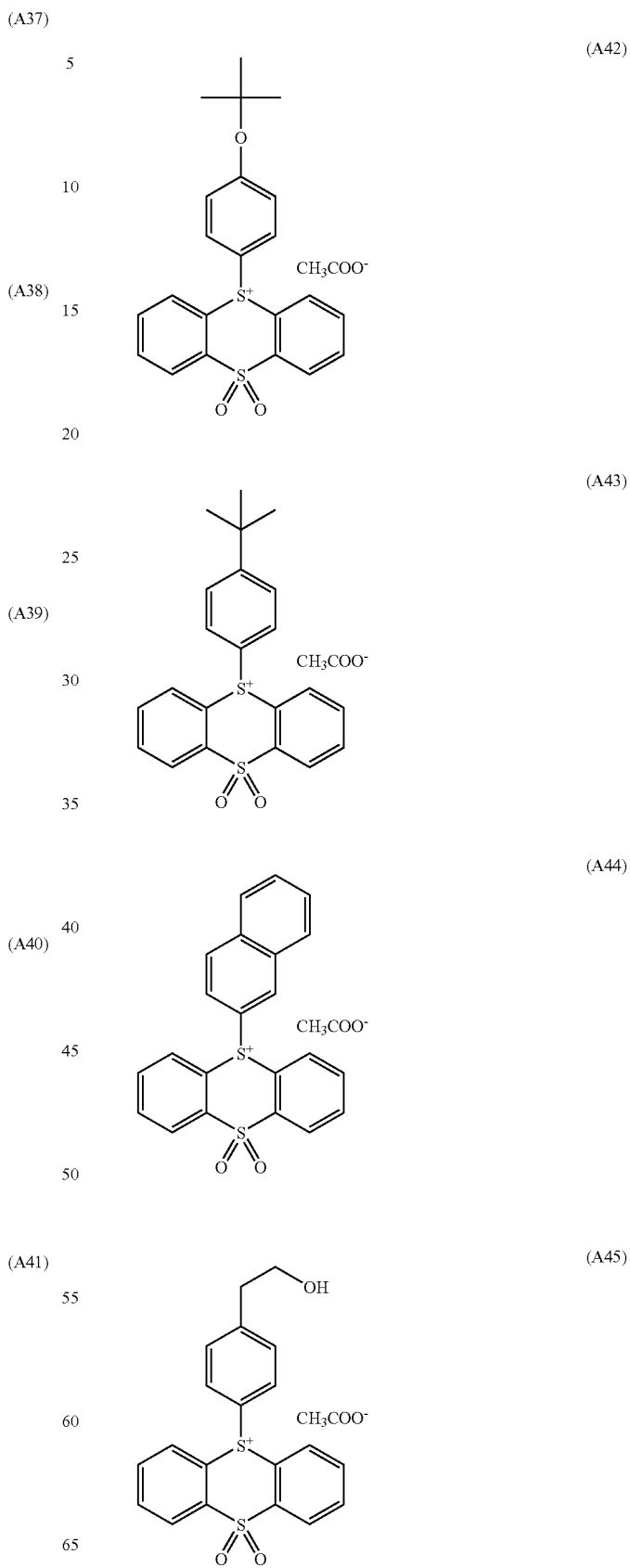

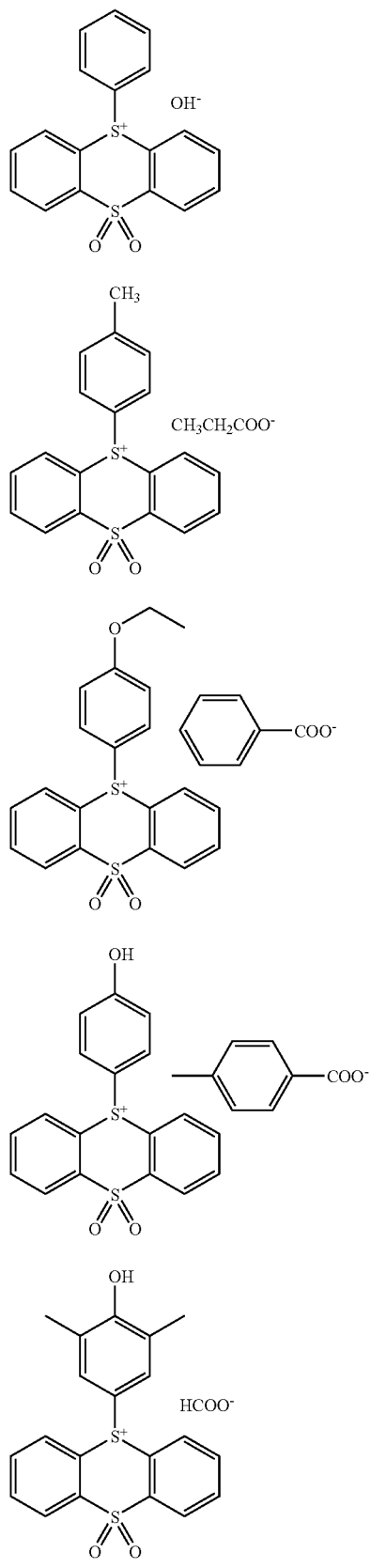
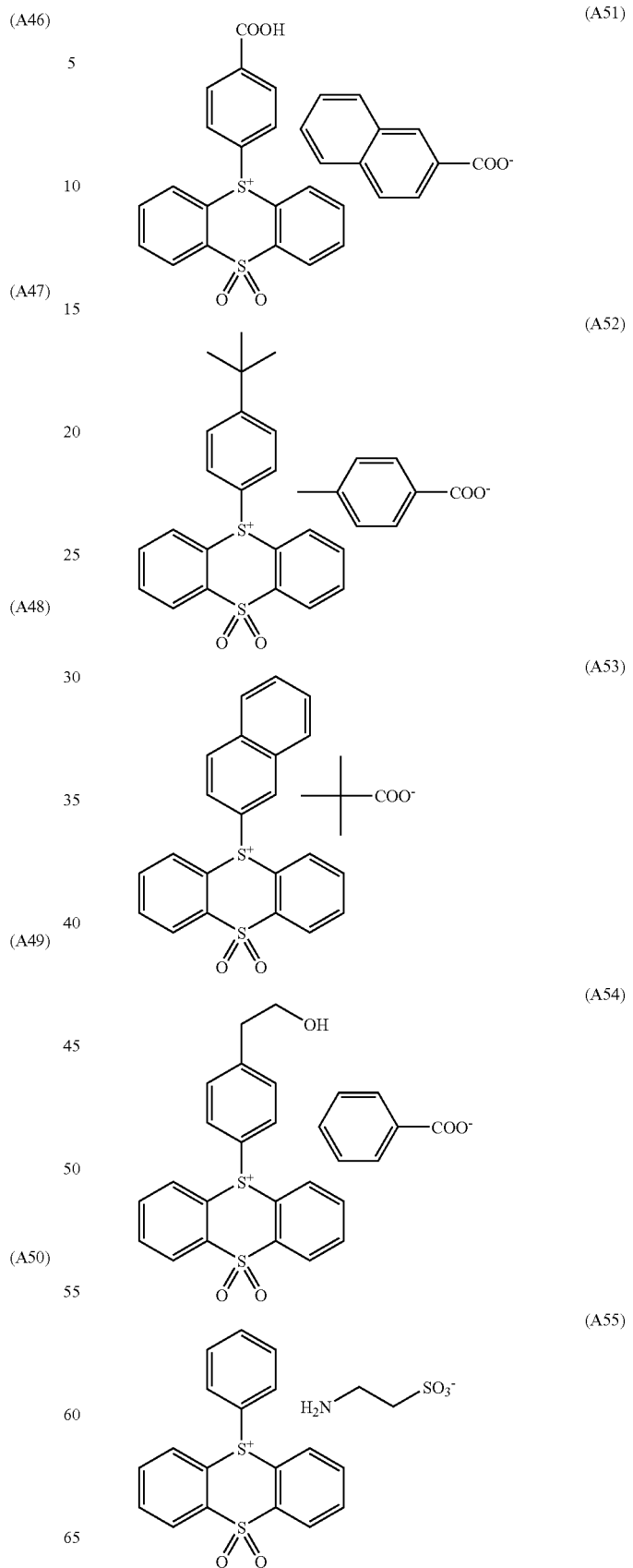

(A56)
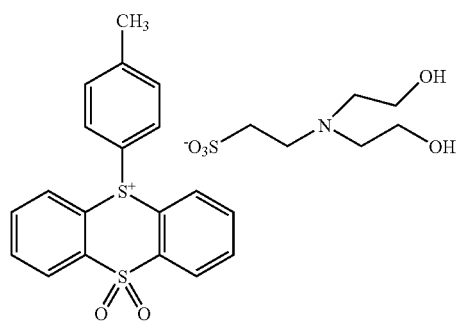
(A57)
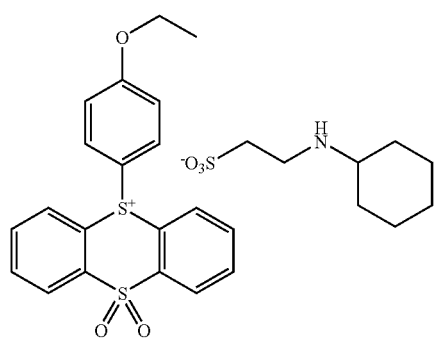
(A58)
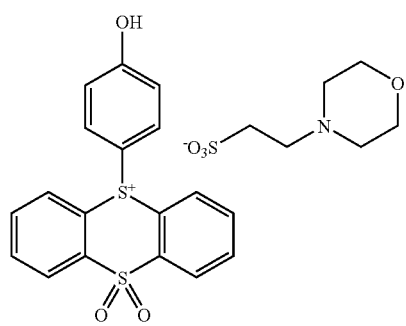
(A59)
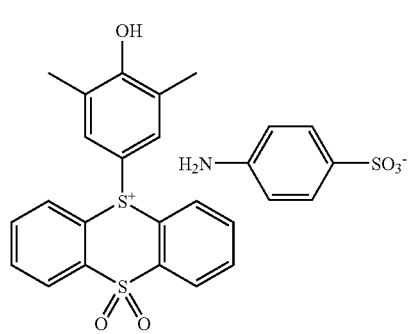
(A60)
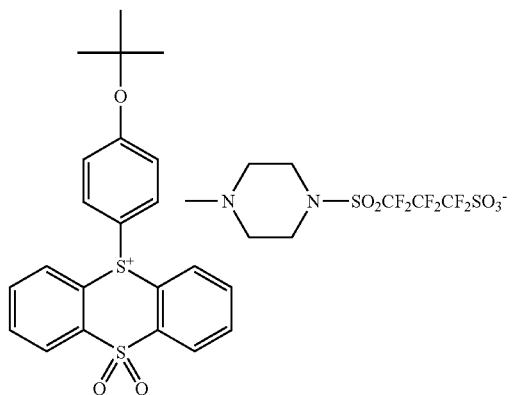
(A61)
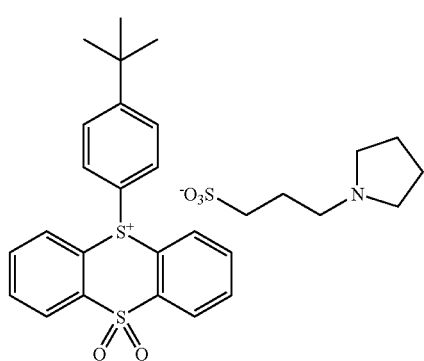
(A62)
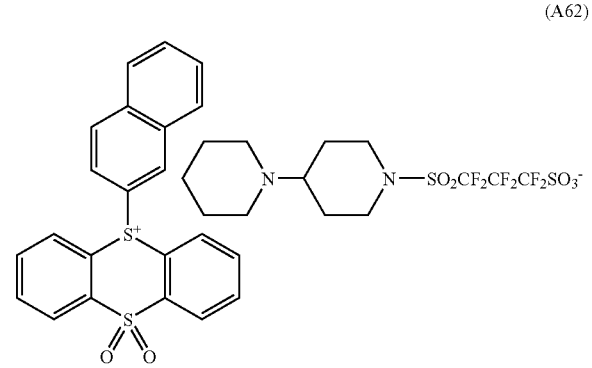
(A63)
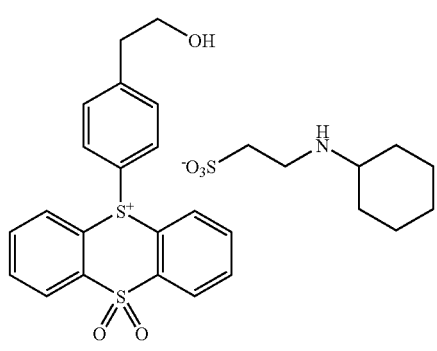

-continued
(A64)
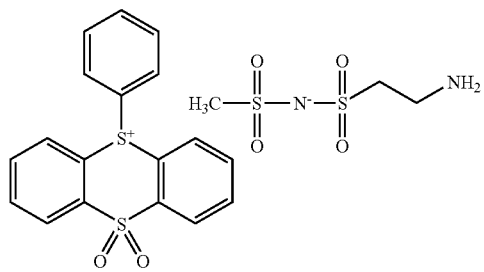
(A65)
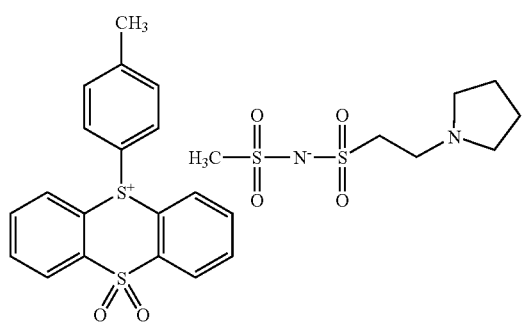
(A66)
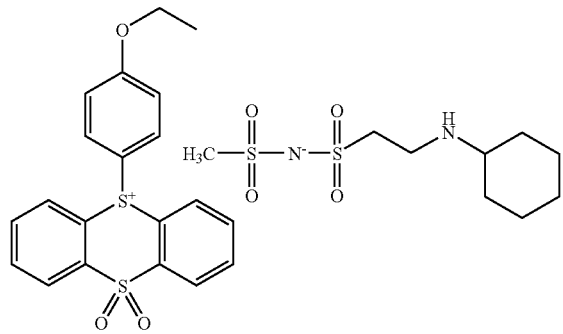
(A67)
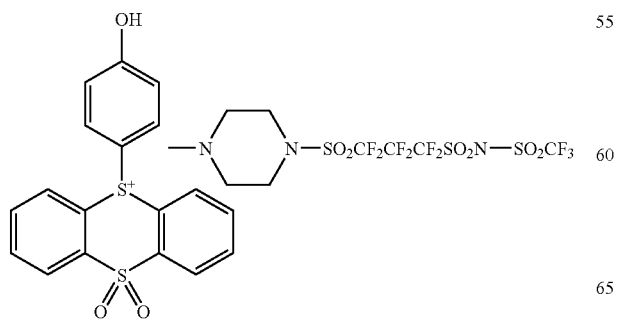
-continued
(A68)
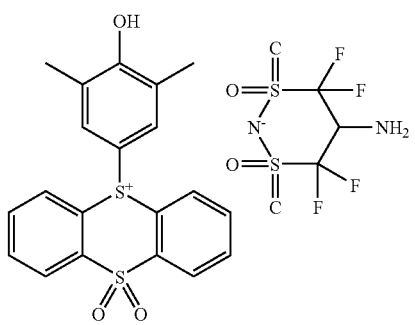
(A69)
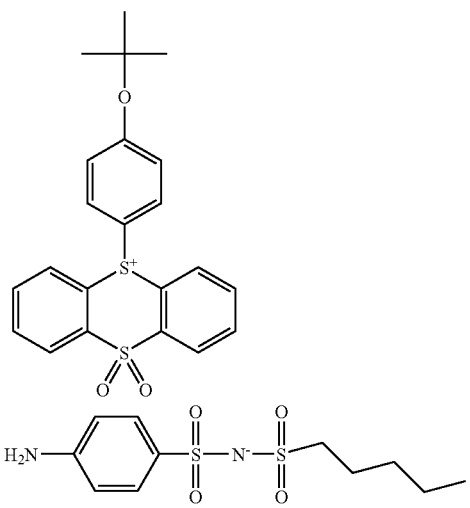
(A70)
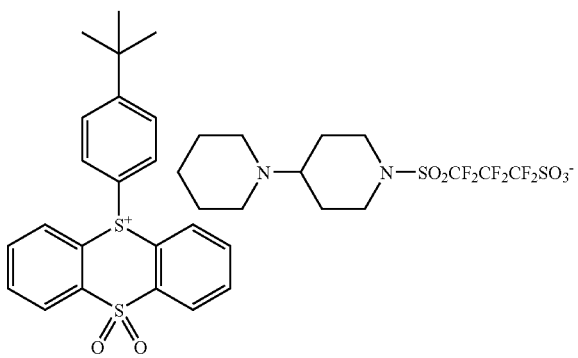
(A71)
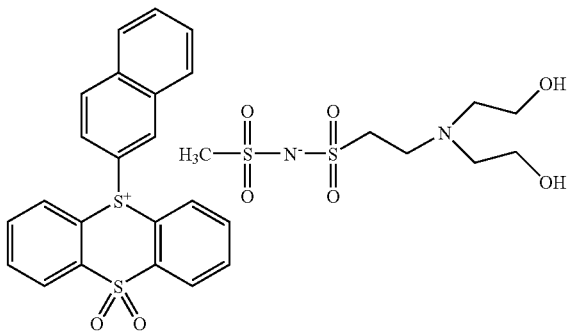

(A72)

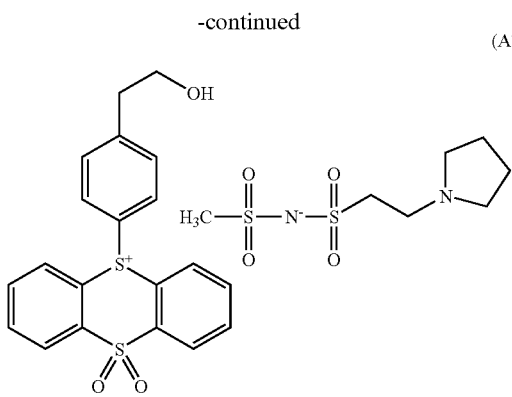

Compound (B) Capable of Generating an Acid Upon Irradiation with an Actinic Ray or Radiation:

The photosensitive composition in the invention may contain the following shown compound (B) capable of generating an acid upon irradiation with an actinic ray or radiation (acid generator B) one kind alone, or may contain two or more kinds of acid generators in combination. As acid generator B, photocationic polymerization photoinitiators, photoradical polymerization photoinitiators, photo-decoloring agents and photo-discoloring agents of dyestuffs, well-known compounds capable of generating an acid upon irradiation with an actinic ray or radiation that are used in micro-resists and the like, and the mixtures of these compounds can be optionally selected and used.

For example, diazonium salt, phosphonium salt, sulfonium salt, iodonium salt, imidosulfonate, oximesulfonate, diazodisulfone, disulfone, and o-nitrobenzylsulfonate are exemplified as acid generator B.

Further, compounds obtained by introducing a group or a compound capable of generating an acid upon irradiation with an actinic ray or radiation to the main chain or side chain of polymers, for example, the compounds disclosed in U.S. Pat. No. 3,849,137, German Patent 3,914,407, JP-A-63-26653, JP-A-55-164824, JP-A-62-69263, JP-A-63-146038, JP-A-63-163452, JP-A-62-153853, JP-A-63-146029, etc., can be used.

The compounds generating an acid by the action of light as disclosed in U.S. Pat. No. 3,779,778, EP 126712, etc., can also be used.

As preferred compounds among the compounds capable of generating an acid upon irradiation with an actinic ray or radiation, compounds represented by the following formula (ZI), (ZII) or (ZIII) can be exemplified.

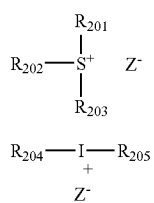

ZI

ZII

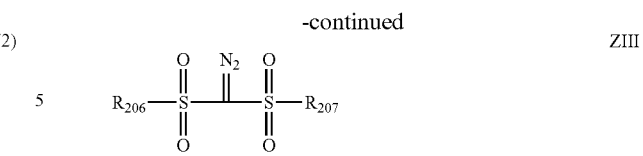

ZIII

In formula (ZI), $R_{201}$, $R_{202}$ and $R_{203}$ each represents an organic group.

The number of carbon atoms of the organic groups represented by $R_{201}$, $R_{202}$ and $R_{203}$ is preferably from 1 to 30, and more preferably from 1 to 20.

Any two of $R_{201}$, $R_{202}$ and $R_{203}$ may be bonded to each other to form a cyclic structure, and an oxygen atom, a sulfur atom, an ester bond, an amido bond or a carbonyl group may be contained in the ring. As the group formed by bonding two of $R_{201}$, $R_{202}$ and $R_{203}$, an alkylene group (e.g., a butylene group, a pentylene group) can be exemplified.

$Z^-$ represents a non-nucleophilic anion.

The examples of the non-nucleophilic anions represented by $Z^-$ include, e.g., a sulfonate anion, a carboxylate anion, a sulfonylimide anion, a bis(alkylsulfonyl)imide anion, and a tris(alkylsulfonyl)methyl anion.

A non-nucleophilic anion is an anion having extremely low ability of causing a nucleophilic reaction and capable of restraining the aging decomposition due to an intramolecular nucleophilic reaction, so that the aging stability of a resist can be improved with a non-nucleophilic anion.

As sulfonate anions, e.g., an aliphatic sulfonate anion, an aromatic sulfonate anion and a camphor sulfonate anion are exemplified.

As carboxylate anions, e.g., an aliphatic carboxylate anion, an aromatic carboxylate anion and an aralkylcarboxylate anion are exemplified.

The aliphatic moiety in the aliphatic sulfonate anion may be an alkyl group or a cycloalkyl group, preferably an alkyl group having from 1 to 30 carbon atoms and a cycloalkyl group having from 3 to 30 carbon atoms, e.g., a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbonyl group, and a boronyl group are exemplified.

The aromatic group in the aromatic sulfonate anion is preferably an aryl group having from 6 to 14 carbon atoms, e.g., a phenyl group, a tolyl group, and a naphthyl group are exemplified.

The alkyl group, cycloalkyl group and aryl group in the aliphatic sulfonate anion and aromatic sulfonate anion may have a substituent. As the substituents of the alkyl group, cycloalkyl group and aryl group in the aliphatic sulfonate anion and aromatic sulfonate anion, e.g., a nitro group, a halogen atom (a fluorine atom, a chlorine atom, a bromine atom, and an iodine atom), a carboxyl group, a hydroxyl group, an amino group, a cyano group, an alkoxyl group (preferably having from 1 to 5 carbon atoms), a cycloalkyl group (preferably having from 3 to 15 carbon atoms), an aryl group (preferably having from 6 to 14 carbon atoms), an alkoxycarbonyl group (preferably having from 2 to 7 carbon atoms), an acyl group (preferably having from 2 to 12 carbon atoms), an alkoxycarbonyloxy group (preferably having from 2 to 7 carbon atoms), etc., are exemplified. As for the aryl group and the cyclic structure in each group, an alkyl group (preferably having from 1 to 15 carbon atoms) can further be exemplified as the substituent.

As the aliphatic moiety in the aliphatic carboxylate anion, the same alkyl groups and cycloalkyl groups as in the aliphatic sulfonate anion can be exemplified.

As the aromatic group in the aromatic carboxylate anion, the same aryl groups as in the aromatic sulfonate anion can be exemplified.

As the aralkyl group in the aralkylcarboxylate anion, preferably an aralkyl group having from 6 to 12 carbon atoms, e.g., a benzyl group, a phenethyl group, a naphthylmethyl group, and a naphthylethyl group can be exemplified.

The alkyl group, cycloalkyl group, aryl group, and aralkyl group in the aliphatic carboxylate anion, aromatic carboxylate anion and aralkylcarboxylate anion may have a substituent. As the substituents of the alkyl group, cycloalkyl group, aryl group and aralkyl group in the aliphatic carboxylate anion, aromatic carboxylate anion and aralkyl-carboxylate anion, e.g., the same halogen atom, alkyl group, cycloalkyl group, alkoxyl group and alkylthio group as in the aromatic sulfonate anion can be exemplified.

As the sulfonylimide anion, e.g., a saccharin anion can be exemplified.

The alkyl group in the bis(alkylsulfonyl)imide anion and tris(alkylsulfonyl)methyl anion is preferably an alkyl group having from 1 to 5 carbon atoms, e.g., a methyl group, an ethyl group, a propyl group, an isopropyl group, an n-butyl group, an isobutyl group, a sec-butyl group, a pentyl group, a neopentyl group, etc., are exemplified. As the substituents of these alkyl groups, a halogen atom, an alkyl group substituted with a halogen atom, an alkoxyl group, an alkylthio group, etc., can be exemplified, and an alkyl group substituted with a fluorine atom is preferred.

As other non-nucleophilic anions, e.g., fluorinated phosphorus, fluorinated boron and fluorinated antimony can be exemplified.

As the non-nucleophilic anions represented by Z⁻, an aliphatic sulfonate anion in which the α-position of the sulfonic acid is substituted with a fluorine atom, an aromatic sulfonate anion substituted with a fluorine atom or a group having a fluorine atom, a bis(alkylsulfonyl)imide anion in which the alkyl group is substituted with a fluorine atom, and a tris (alkylsulfonyl)methide anion in which the alkyl group is substituted with a fluorine atom are preferred. More preferred non-nucleophilic anions are an aliphatic perfluoro-sulfonate anion having from 4 to 8 carbon atoms, and a benzenesulfonate anion having a fluorine atom, and still more preferred non-nucleophilic anions are a nonafluorobutane-sulfonate anion, a perfluorooctanesulfonate anion, a pentafluorobenzenesulfonate anion, and a 3,5-bis(trifluoromethyl)benzenesulfonate anion.

As the examples of the organic groups represented by $R_{201}$, $R_{202}$ and $R_{203}$, the corresponding groups in the later-described compounds represented by formula (ZI-1), (ZI-2) or (ZI-3) can be exemplified.

The compound may be a compound having a plurality of structures represented by formula (ZI). For instance, the compound may have a structure that at least one of $R_{201}$, $R_{202}$ and $R_{203}$ of a compound represented by formula (ZI) is bonded to at least one of $R_{201}$, $R_{202}$ and $R_{203}$ of another compound represented by formula (ZI).

The following compounds (ZI-1), (ZI-2) and (ZI-3) can be exemplified as more preferred components (ZI).

Compound (ZI-1) is an arylsulfonium compound that at least one of $R_{201}$ to $R_{203}$ in formula (ZI) represents an aryl group, i.e., a compound having arylsulfonium as the cation.

All of $R_{201}$ to $R_{203}$ of the arylsulfonium compound may be aryl groups, or a part of $R_{201}$ to $R_{203}$ may be an aryl group and the remainder may be an alkyl group or a cycloalkyl group.

As the arylsulfonium compounds, e.g., a triarylsulfonium compound, a diarylalkylsulfonium compound, an aryldialkyl-sulfonium compound, a diarylcycloalkylsulfonium compound, and an aryldicycloalkylsulfonium compound are exemplified.

As the aryl groups of the arylsulfonium compound, a phenyl group and a naphthyl group are preferred, and the more preferred group is a phenyl group. The aryl group may be an aryl group having a heterocyclic structure having an oxygen atom, a nitrogen atom or a sulfur atom. As the aryl group having a heterocyclic structure, e.g., a pyrrole residue (a group formed by eliminating one hydrogen atom from pyrrole), a furan residue (a group formed by eliminating one hydrogen atom from furan), a thiophene residue (a group formed by eliminating one hydrogen atom from thiophene), an indole residue (a group formed by eliminating one hydrogen atom from indole), a benzofuran residue (a group formed by eliminating one hydrogen atom from benzofuran), and a benzothiophene residue (a group formed by eliminating one hydrogen atom from benzothiophene) can be exemplified. When the arylsulfonium compound has two or more aryl groups, these two or more aryl groups may be the same or different.

The alkyl group or the cycloalkyl group that the arylsulfonium compound has according to necessity is preferably a straight chain or branched alkyl group having from 1 to 15 carbon atoms or a cycloalkyl group having from 3 to 15 carbon atoms, e.g., a methyl group, an ethyl group, a propyl group, an n-butyl group, a sec-butyl group, a t-butyl group, a cyclopropyl group, a cyclobutyl group, a cyclohexyl group, etc., can be exemplified.

The aryl group, alkyl group and cycloalkyl group represented by $R_{201}$, $R_{202}$ and $R_{203}$ may have a substituent and, e.g., an alkyl group (e.g., having from 1 to 15 carbon atoms), a cycloalkyl group (e.g., having from 3 to 15 carbon atoms), an aryl group (e.g., having from 6 to 14 carbon atoms), an alkoxyl group (e.g., having from 1 to 15 carbon atoms), a halogen atom, a hydroxyl group, and a phenylthio group are exemplified as the substituents. The preferred substituents are a straight chain or branched alkyl group having from 1 to 12 carbon atoms, a cycloalkyl group having from 3 to 12 carbon atoms, and a straight chain, branched or cyclic alkoxyl group having from 1 to 12 carbon atoms, and the more preferred substituents are an alkyl group having from 1 to 4 carbon atoms and an alkoxyl group having from 1 to 4 carbon atoms. The substituent may be substituted on any one of three of $R_{201}$ to $R_{203}$, or may be substituted on all of the three. When $R_{201}$, $R_{202}$ and $R_{203}$ each represents an aryl group, it is preferred that the substituent be substituted on the p-position of the aryl group.

Compound (ZI-2) is described below.

Compound (ZI-2) is a compound in the case where $R_{201}$, $R_{202}$ and $R_{203}$ in formula (ZI) each represents an organic group not containing an aromatic ring. The aromatic ring here also includes an aromatic ring containing a hetero atom.

The organic groups not containing an aromatic ring represented by $R_{201}$ to $R_{203}$ preferably have from 1 to 30 carbon atoms, and more preferably from 1 to 20 carbon atoms.

$R_{201}$, $R_{202}$ and $R_{203}$ each preferably represents an alkyl group, a cycloalkyl group, an allyl group, or a vinyl group, more preferably a straight chain or branched 2-oxoalkyl group, a 2-oxocycloalkyl group or an alkoxycarbonylmethyl group, and especially preferably represents a straight or branched 2-oxoalkyl group.

The alkyl group and cycloalkyl group represented by $R_{201}$ to $R_{203}$ are preferably a straight chain or branched alkyl group having from 1 to 10 carbon atoms (e.g., a methyl group, an ethyl group, a propyl group, a butyl group, a pentyl group), and a cycloalkyl group having from 3 to 10 carbon atoms (e.g., a cyclopentyl group, a cyclohexyl group, a norbonyl group). The alkyl group is more preferably a 2-oxoalkyl group or an alkoxycarbonylmethyl group. The cycloalkyl group is more preferably a 2-oxocycloalkyl group.

The 2-oxoalkyl group may be either a straight chain or branched group, and a group having >C=O on the 2-position of the above alkyl group can be exemplified as a preferred group.

The 2-oxocycloalkyl group is preferably a group having >C=O on the 2-position of the above cycloalkyl group.

As the alkoxyl group in the alkoxycarbonylmethyl group, preferably an alkoxyl group having from 1 to 5 carbon atoms (e.g., a methoxy group, an ethoxy group, a propoxy group, a butoxy group, a pentoxy group) can be exemplified.

$R_{201}$ to $R_{203}$ may further be substituted with a halogen atom, an alkoxyl group (e.g., an alkoxyl group having from 1 to 5 carbon atoms), a hydroxyl group, a cyano group, or a nitro group.

Compound (ZI-3) is a compound represented by the following formula (ZI-3), which compound has a phenacylsulfonium salt structure.

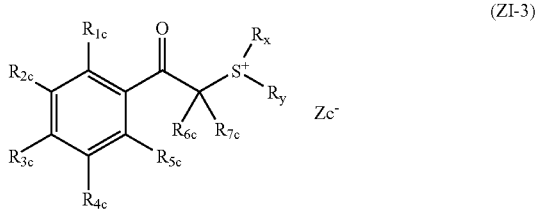

(ZI-3)

In formula (ZI-3), $R_{1c}$, $R_{2c}$, $R_{3c}$, $R_{4c}$ and $R_{5c}$ each represents a hydrogen atom, an alkyl group, a cycloalkyl group, an alkoxyl group, or a halogen atom.

$R_{6c}$ and $R_{7c}$ each represents a hydrogen atom, an alkyl group or a cycloalkyl group.

$R_x$ and $R_y$ each represents an alkyl group, a cycloalkyl group, an allyl group, or a vinyl group.

Any two or more of $R_{1c}$ to $R_{5c}$, $R_{6c}$ and $R_{7c}$, and $R_x$ and $R_y$ may be bonded to each other to form cyclic structures, respectively, and the cyclic structures may contain an oxygen atom, a sulfur atom, an ester bond, or an amido bond. As the groups formed by any two or more of $R_{1c}$ to $R_{5c}$, $R_{6c}$ and $R_{7c}$, and $R_x$ and $R_y$, a butylene group, a pentylene group, etc., can be exemplified.

$Z_c^-$ represents a non-nucleophilic anion, and the same non-nucleophilic anions as represented by $Z^-$ in formula (ZI) can be exemplified.

The alkyl groups represented by $R_{1c}$ to $R_{7c}$ may be either straight chain or branched, e.g., an alkyl group having from 1 to 20 carbon atoms, preferably a straight chain or branched alkyl group having from 1 to 12 carbon atoms (e.g., a methyl group, an ethyl group, a straight chain or branched propyl group, a straight chain or branched butyl group, a straight chain or branched pentyl group) can be exemplified. As the cycloalkyl groups represented by $R_{1c}$ to $R_{7c}$, a cycloalkyl group having from 3 to 8 carbon atoms (e.g., a cyclopentyl group and a cyclohexyl group) can be exemplified.

The alkoxyl groups represented by $R_{1c}$ to $R_{5c}$ may be any of straight chain, branched and cyclic, e.g., an alkoxyl group having from 1 to 10 carbon atoms, preferably a straight chain or branched alkoxyl group having from 1 to 5 carbon atoms (e.g., a methoxy group, an ethoxy group, a straight chain or branched propoxy group, a straight chain or branched butoxy group, a straight chain or branched pentoxy group), a cyclic alkoxyl group having from 3 to 8 carbon atoms (e.g., a cyclopentyloxy group, a cyclohexyloxy group) can be exemplified.

It is preferred that any of $R_{1c}$ to $R_{5c}$ represents a straight chain or branched alkyl group, a cycloalkyl group, or a straight chain, branched or cyclic alkoxyl group, and it is more preferred that the sum total of the carbon atoms of $R_{1c}$ to $R_{5c}$ is from 2 to 15, by which the solubility in a solvent increases and generation of particles during preservation can be restrained.

As the alkyl group and cycloalkyl group represented by $R_x$ and $R_y$, the same alkyl groups and cycloalkyl groups represented by $R_{1c}$ to $R_{7c}$ can be exemplified, and a 2-oxoalkyl group, a 2-oxocycloalkyl group and an alkoxycarbonylmethyl group are more preferred.

As the 2-oxoalkyl group and the 2-oxocycloalkyl group, groups respectively having >C=O on the 2-position of the alkyl group and the cycloalkyl group represented by $R_{1c}$ to $R_{7c}$ can be exemplified.

As the alkoxyl group of the alkoxycarbonylmethyl group, the same alkoxyl groups as those represented by $R_{1c}$ to $R_{5c}$ can be exemplified.

$R_x$ and $R_y$ each preferably represents an alkyl group or a cycloalkyl group having 4 or more carbon atoms, more preferably 6 or more carbon atoms, and still more preferably represents an alkyl group or a cycloalkyl group having 8 or more carbon atoms.

In formulae (ZII) and (ZIII), $R_{204}$, $R_{205}$, $R_{206}$ and $R_{207}$ each represents an aryl group, an alkyl group or a cycloalkyl group.

The aryl group represented by $R_{204}$ to $R_{207}$ is preferably a phenyl group or a naphthyl group, and more preferably a phenyl group. The aryl group represented by $R_{204}$ to $R_{207}$ may be an aryl group having a heterocyclic structure and having an oxygen atom, a nitrogen atom or a sulfur atom. As the aryl group having a heterocyclic structure, e.g., a pyrrole residue (a group formed by eliminating one hydrogen atom from pyrrole), a furan residue (a group formed by eliminating one hydrogen atom from furan), a thiophene residue (a group formed by eliminating one hydrogen atom from thiophene), an indole residue (a group formed by eliminating one hydrogen atom from indole), a benzofuran residue (a group formed by eliminating one hydrogen atom from benzofuran), and a benzothiophene residue (a group formed by eliminating one hydrogen atom from benzothiophene) can be exemplified.

As the alkyl group and the cycloalkyl group represented by $R_{204}$ to $R_{207}$, a straight chain or branched alkyl group having from 1 to 10 carbon atoms (e.g., a methyl group, an ethyl group, a propyl group, a butyl group, a pentyl group), and a cycloalkyl group having from 3 to 10 carbon atoms (e.g., a cyclopentyl group, a cyclohexyl group, a norbonyl group) are preferably exemplified.

The aryl group, alkyl group and cycloalkyl group represented by $R_{204}$ to $R_{207}$ may have a substituent. As the substituents that the aryl group, alkyl group and cycloalkyl group represented by $R_{204}$ to $R_{207}$ may have, e.g., an alkyl group (e.g., having from 1 to 15 carbon atoms), a cycloalkyl group (e.g., having from 3 to 15 carbon atoms), an aryl group (e.g., having from 6 to 15 carbon atoms), an alkoxyl group (e.g., having from 1 to 15 carbon atoms), a halogen atom, a hydroxyl group, and a phenylthio group can be exemplified.

$Z^-$ represents a non-nucleophilic anion, and the same non-nucleophilic anions as those represented by $Z^-$ in formula (ZI) can be exemplified.

As the compounds capable of generating an acid upon irradiation with an actinic ray or radiation that can be used in the invention, the compounds represented by the following formula (ZIV), (ZV) or (ZVI) can further be exemplified.

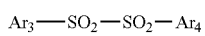
ZIV

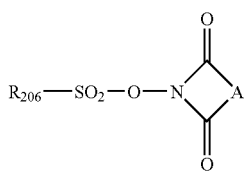
ZV

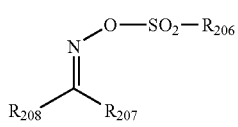
ZVI

In formulae (ZIV), (ZV) and (ZVI), $Ar_3$ and $Ar_4$ each represents an aryl group.

$R_{206}$, $R_{207}$ and $R_{208}$ each represents an alkyl group, a cycloalkyl group or an aryl group.

A represents an alkylene group, an alkenylene group or an arylene group.

Of the compounds capable of generating an acid upon irradiation with an actinic ray or radiation, more preferred compounds are the compounds represented by formulae (ZI), (ZII) and (ZIII).

Further, as the compounds capable of generating an acid upon irradiation with an actinic ray or radiation, a compound capable of generating an acid having one sulfonic acid group or imido group is preferred, a compound capable of generating a monovalent perfluoroalkanesulfonic acid, a compound capable of generating an aromatic sulfonic acid substituted with a monovalent fluorine atom or a group containing a fluorine atom, and a compound capable of generating an imidic acid substituted with a monovalent fluorine atom or a group containing a fluorine atom are more preferred, and a sulfonium salt of a fluoride-substituted alkanesulfonic acid, a fluorine-substituted benzenesulfonic acid, or a fluorine-substituted imidic acid is still more preferred. The usable acid generators are especially preferably a fluoride-substituted alkanesulfonic acid, a fluoride-substituted benzenesulfonic acid, and a fluoride-substituted imidic acid each having pKa of generated acid of −1 or less are especially preferred, by which sensitivity is improved.

Of the compounds capable of generating an acid upon irradiation with an actinic ray or radiation, especially preferred examples are shown below.

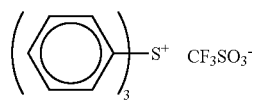
(z1)

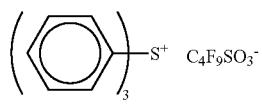
(z2)

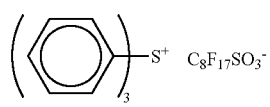
(z3)

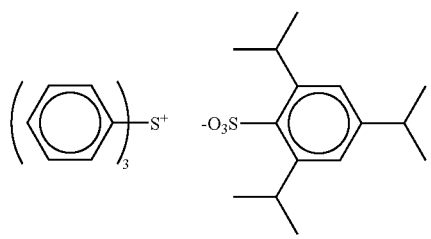
(z4)

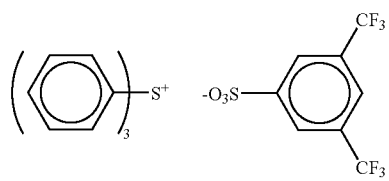
(z5)

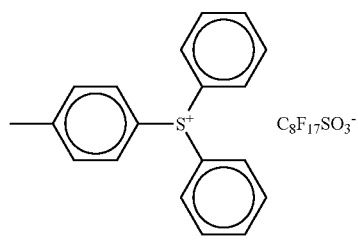
(z6)

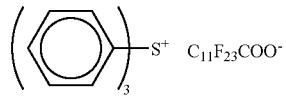
(z7)

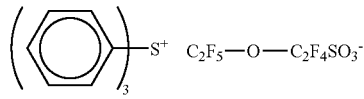
(z8)

-continued
(z9)
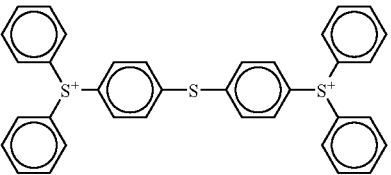
(z10)
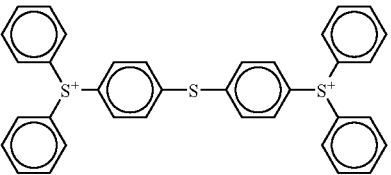
(z11)
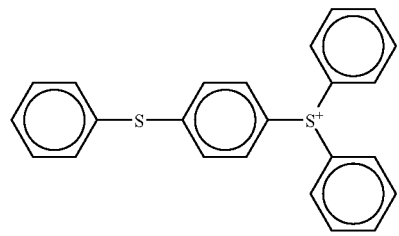
(z12)
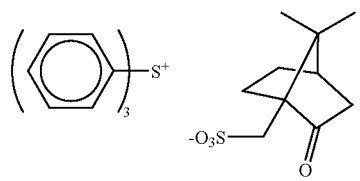
(z13)
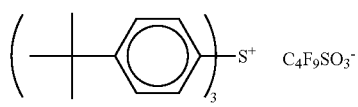
(z14)
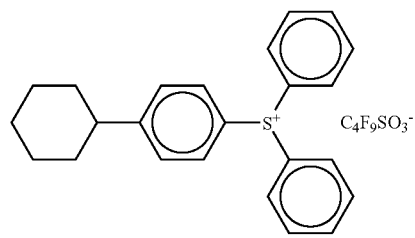
(z15)
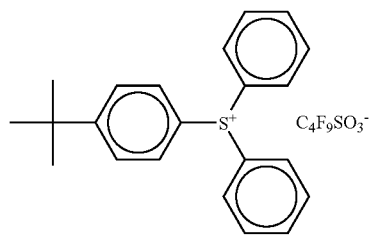
(z16)
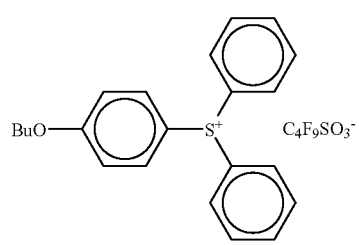
(z17)
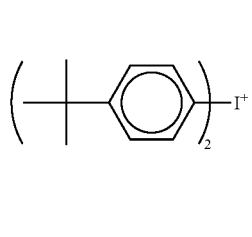
(z18)
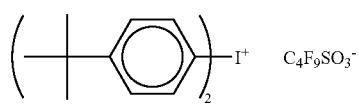
(z19)
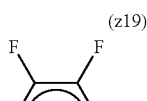
(z20)
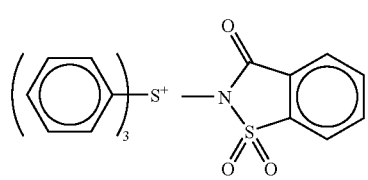
(z21)
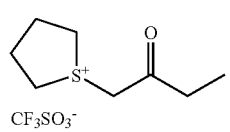
(z22)
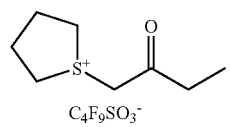
(z23)

-continued
(z24)
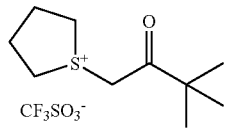
(z25)
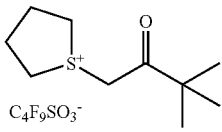
(z26)
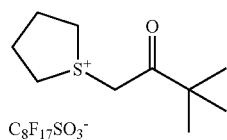
(z27)
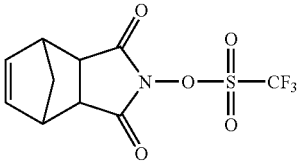
(z28)
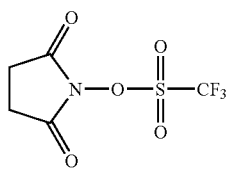
(z29)
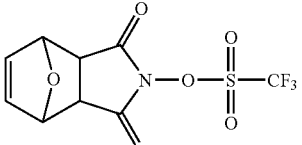
(z30)
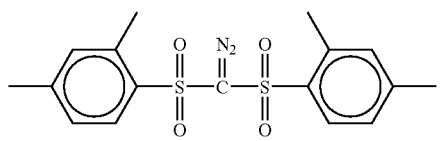
(z31)
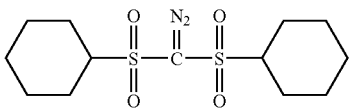
(z32)
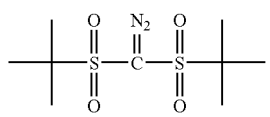
(z33)
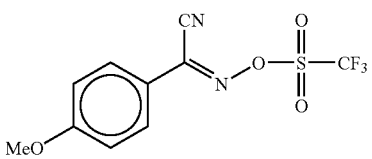
(z34)
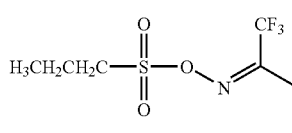
(z35)
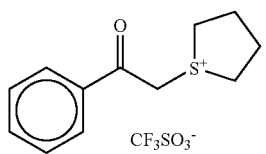
(z36)
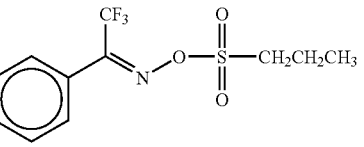
(z37)
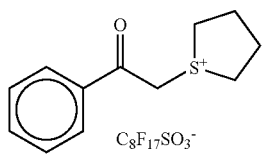
(z38)
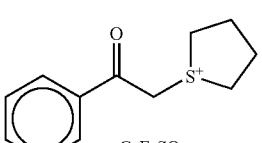
(z39)
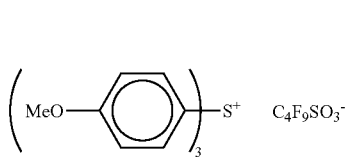
(z40)
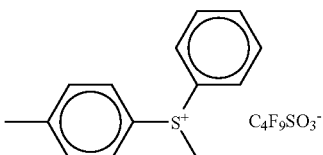
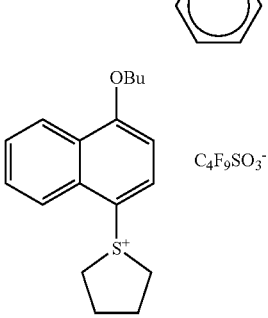

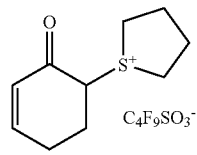
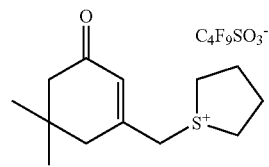
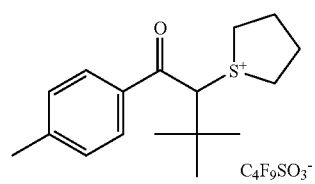
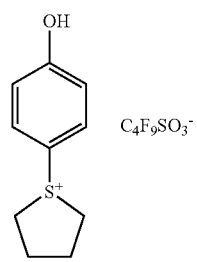
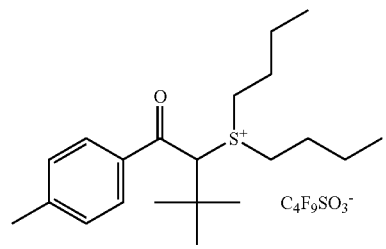
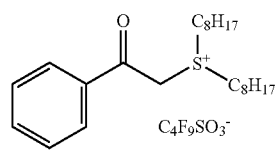
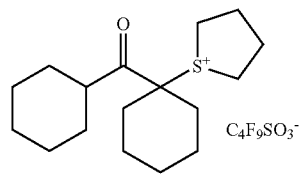
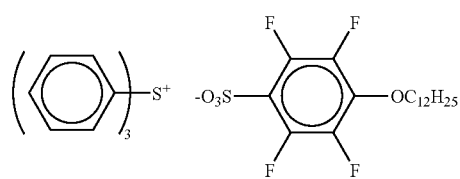
-continued
(z41) 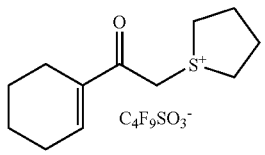 (z42)
(z43) 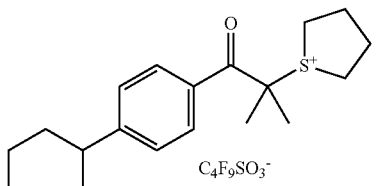 (z44)
(z45) 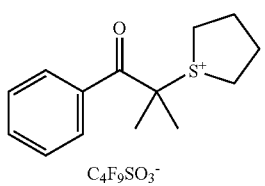 (z46)
(z47) 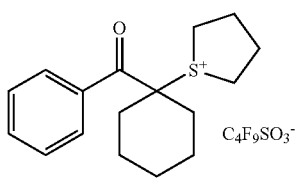 (z48)
(z49) 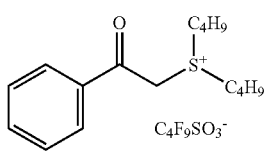 (z50)
(z51) 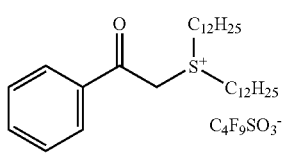 (z52)
(z53) 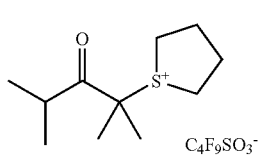 (z54)
(z55) 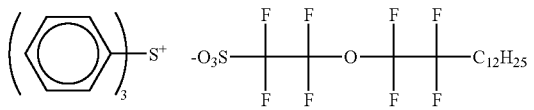 (z56)

-continued (z57) (z58) (z59) (z60) (z61) (z62) (z63) (z64) (z65)

The addition amount of acid generator (B) as a total amount is preferably from 0.1 to 10.0 mass % based on all the solids content of the photosensitive composition, more preferably from 0.5 to 5.0 mass %, and still more preferably from 1.0 to 3.0 mass %.

Resin (C) Capable of Decomposing by the Action of an Acid to Increase Solubility in an Alkali Developing Solution:

Resin capable of decomposing by the action of an acid to increase solubility in an alkali developing solution (resin (C)) for use in the positive photosensitive composition in the invention is resin having a group capable of decomposing by the action of an acid to generate an alkali-soluble group (an acid-decomposable group) on the main chain or side chain of the resin, or on both the main chain and side chain. Of these resins, resin having an acid-decomposable group on the side chain is more preferred.

A preferred acid-decomposable group is a group obtained by substituting the hydrogen atom of an alkali-soluble group such as a —COOH group or an —OH group with a group capable of desorption by the action of an acid.

A preferred acid-decomposable group in the invention is an acetal group or a tertiary ester group.

The parent resin in the case where the acid-decomposable group is bonded as the side chain is an alkali-soluble resin having an —OH group or a —COOH group on the side chain. For example, the later-described alkali-soluble resins can be exemplified.

The alkali dissolution rate of such alkali-soluble resins is preferably 170 Å/sec or more when measured with 0.261N tetramethylammonium hydroxide (TMAH) at 23° C., and especially preferably 330 Å/sec or more.

From this point of view, particularly preferred alkali-soluble resins are o-, m-, p-poly(hydroxystyrene) and copolymers thereof, hydrogenated poly(hydroxystyrene), halogen- or alkyl-substituted poly(hydroxystyrene), a partially O-alkylated or O-acylated product of poly-(hydroxystyrene), styrene-hydroxystyrene copolymers, α-methylstyrene-hydroxystyrene copolymers, alkali-soluble resins having a hydroxystyrene structural unit such as hydrogenated novolak resins, (meth)acrylic acid, and alkali-soluble resins containing a repeating unit having a carboxyl group such as norbornenecarboxylic acid.

As repeating units having a preferred acid-decomposable group, e.g., t-butoxycarbonyloxystyrene, 1-alkoxyethoxystyrene, and (meth)acrylic acid tertiary alkyl ester are exemplified, and 2-alkyl-2-adamantyl(meth)acrylate and dialkyl (1-adamantyl)methyl(meth)acrylate are more preferred.

Resin (C) for use in the invention can be obtained, as disclosed in EP 254853, JP-A-2-25850, JP-A-3-223860 and JP-A-4-251259, by reacting an alkali-soluble resin with the precursor of an acid-decomposable group, or copolymerizing an alkali-soluble resin monomer to which an acid-decomposable group is bonded with various monomers.

When the positive photosensitive composition of the invention is irradiated with KrF excimer laser beams, electron beams, X-rays, or high energy rays of wavelength of 50 nm or lower (e.g., EUV), it is preferred for resin (C) to have a hydroxystyrene repeating unit, and more preferably a copolymer of hydroxystyrene/hydroxystyrene protected with an acid-decomposable group, or hydroxystyrene/(meth)acrylic acid tertiary alkyl ester.

The specific examples of resins (C) for use in the invention are shown below, but the invention is not restricted thereto.

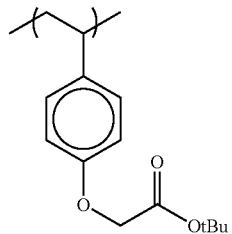

(R-1)

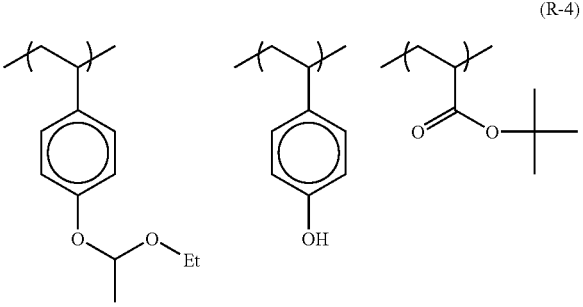

(R-2)

(R-3)

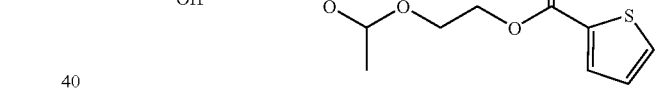

(R-4)

(R-5)

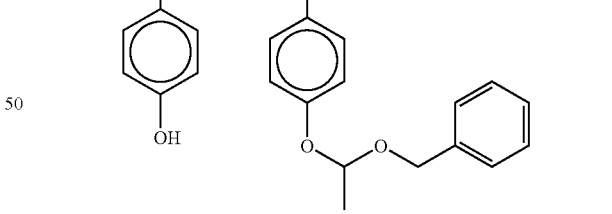

(R-6)

(R-7)

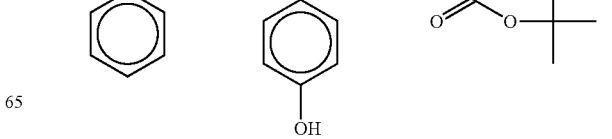

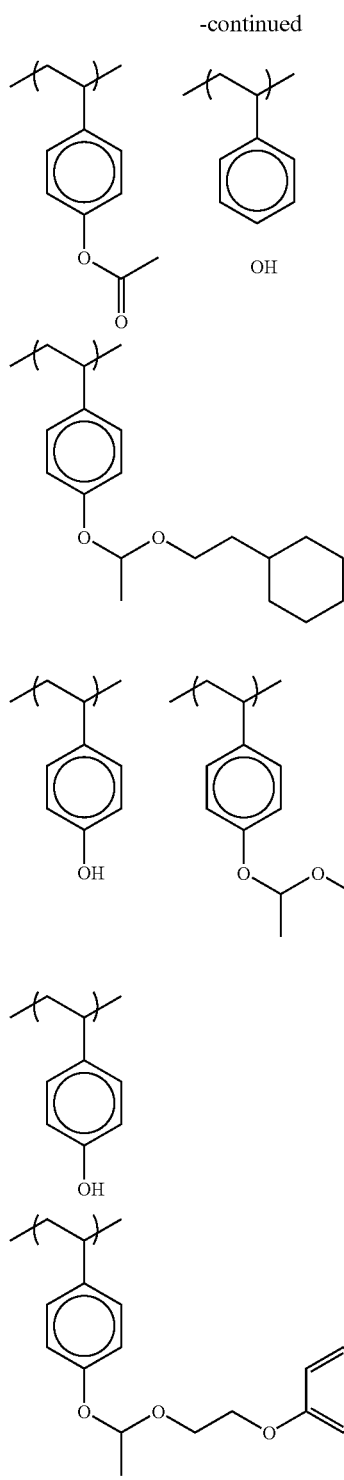
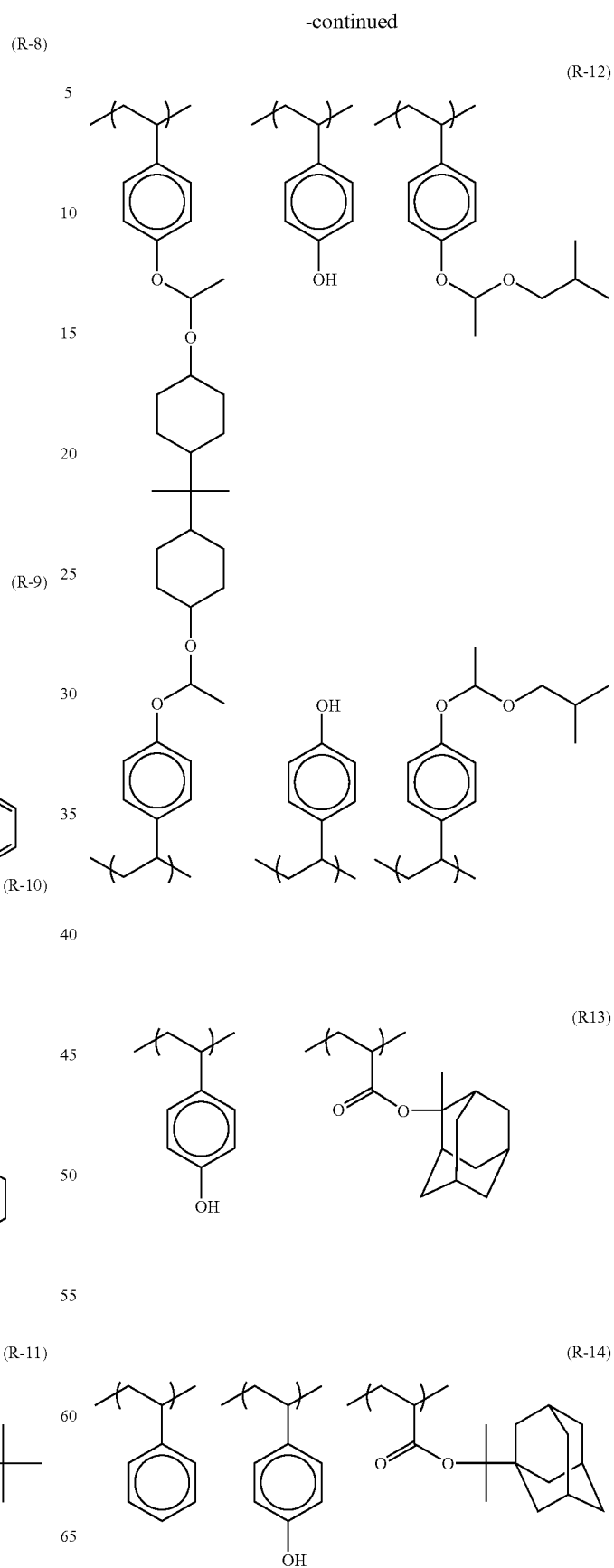

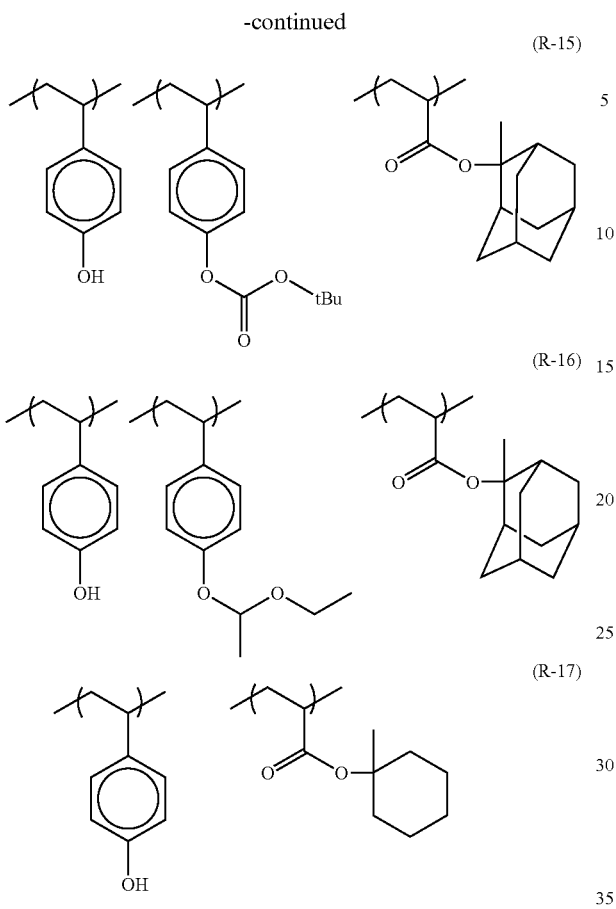

(R-15)

(R-16)

(R-17)

In the above specific examples, tBu means a t-butyl group.

The content of an acid-decomposable group is expressed by B/(B+S), taking the number of the acid-decomposable groups in the resin as (B), and the number of alkali-soluble groups not protected with acid-eliminable groups as (S). The content is preferably from 0.01 to 0.7, more preferably from 0.05 to 0.50, and still more preferably from 0.05 to 0.40.

When the positive photosensitive composition in the invention is irradiated with ArF excimer laser beams, it is preferred that resin (C) is resin having a monocyclic or polycyclic alicyclic hydrocarbon structure and capable of decomposing by the action of an acid to thereby increase the solubility in an alkali developing solution.

As the resin having a monocyclic or polycyclic alicyclic hydrocarbon structure and capable of decomposing by the action of an acid to thereby increase the solubility in an alkali developing solution (hereinafter also referred to as "alicyclic hydrocarbon acid-decomposable resin"), resin containing at least one repeating unit selected from the group consisting of a repeating unit having a partial structure containing alicyclic hydrocarbon represented by any of the following formulae (pI) to (pV), and a repeating unit represented by the following formula (II-AB) is preferred.

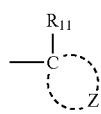

(pI)

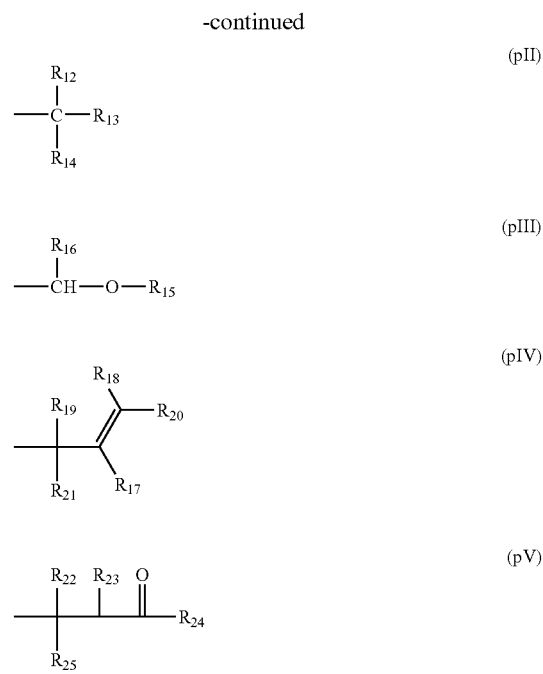

In formulae (pI) to (pV), $R_{11}$ represents a methyl group, an ethyl group, an n-propyl group, an isopropyl group, an n-butyl group, an isobutyl group, or a sec-butyl group; and Z represents an atomic group necessary to form a cycloalkyl group together with a carbon atom.

$R_{12}$, $R_{13}$, $R_{14}$, $R_{15}$ and $R_{16}$ each represents a straight chain or branched alkyl group or cycloalkyl group having from 1 to 4 carbon atoms, provided that at least one of $R_{12}$ to $R_{14}$, or either $R_{15}$ or $R_{16}$ represents a cycloalkyl group.

$R_{17}$, $R_{18}$, $R_{19}$, $R_{20}$ and $R_{21}$ each represents a hydrogen atom, a straight chain or branched alkyl group or cycloalkyl group having from 1 to 4 carbon atoms, provided that at least one of $R_{17}$ to $R_{21}$ represents a cycloalkyl group, and either $R_{19}$ or $R_{21}$ represents a straight chain or branched alkyl group or cycloalkyl group having from 1 to 4 carbon atoms.

$R_{22}$, $R_{23}$, $R_{24}$ and $R_{25}$ each represents a hydrogen atom, a straight chain or branched alkyl group or cycloalkyl group having from 1 to 4 carbon atoms, provided that at least one of $R_{22}$ to $R_{25}$ represents a cycloalkyl group, and $R_{23}$ and $R_{24}$ may by bonded to each other to form a ring.

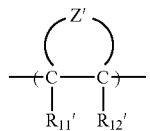

(II-AB)

In formula (II-AB), $R_{11}'$ and $R_{12}'$ each represents a hydrogen atom, a cyano group, a halogen atom, or an alkyl group.

Z' contains bonded two carbon atoms (C—C) and represents an atomic group to form an alicyclic structure.

Formula (II-AB) is more preferably represented by the following formula (II-AB1) or (II-AB2).

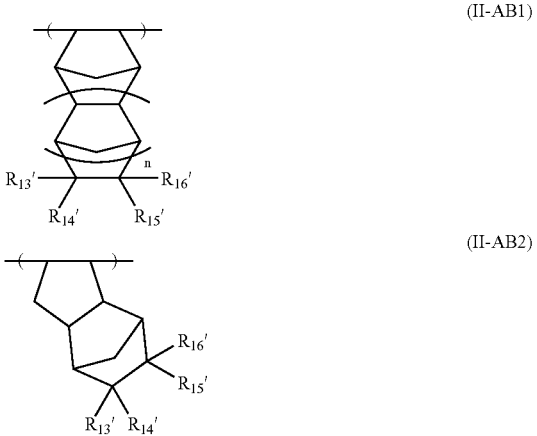

In formulae (II-AB1) and (II-AB2), $R_{13}'$, $R_{14}'$, $R_{15}'$ and $R_{16}'$ each represents a hydrogen atom, a halogen atom, a cyano group, a hydroxyl group, —COOH, —COOR$_5$, a group decomposable by the action of an acid, —C(=O)—X—A'—R$_{17}'$, an alkyl group, or a cycloalkyl group. At least two of $R_{13}'$ to $R_{16}'$ may be bonded to each other to form a ring.

$R_5$ represents an alkyl group, a cycloalkyl group, or a group having a lactone structure.

X represents an oxygen atom, a sulfur atom, —NH—, —NHSO$_2$— or —NHSO$_2$NH—.

A' represents a single bond or a divalent linking group.

$R_{17}'$ represents —COOH, —COOR$_5$, —CN, a hydroxyl group, an alkoxyl group, —CO—NH—R$_6$, —CO—NH—SO$_2$—R$_6$, or a group having a lactone structure.

$R_6$ represents an alkyl group or a cycloalkyl group.

n represents 0 or 1.

The alkyl group represented by $R_{12}$ to $R_{25}$ in formulae (pI) to (pV) is a straight chain or branched alkyl group having from 1 to 4 carbon atoms, e.g., a methyl group, an ethyl group, a propyl group, an n-butyl group, a sec-butyl group, and a t-butyl group are exemplified.

The cycloalkyl group represented by $R_{11}$ to $R_{25}$ or the cycloalkyl group formed by Z and carbon atoms may be monocyclic or polycyclic. Specifically, groups having a monocyclic, bicyclic, tricyclic or tetracyclic structure having 5 or more carbon atoms can be exemplified. The number of carbon atoms of the groups is preferably from 6 to 30, and especially preferably from 7 to 25. These cycloalkyl groups may have a substituent.

As preferred cycloalkyl groups, an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group, and a cyclododecanyl group can be exemplified. More preferred cycloalkyl groups are an adamantyl group, a norbornyl group, a cyclohexyl group, a cyclopentyl group, a tetracyclododecanyl group, and a tricyclodecanyl group.

These alkyl groups and cycloalkyl groups may further have a substituent. As further substituents of the alkyl groups and cycloalkyl groups, an alkyl group (having from 1 to 4 carbon atoms), a halogen atom, a hydroxy group, an alkoxyl group (having from 1 to 4 carbon atoms), a carboxyl group, and an alkoxycarbonyl group (having from 2 to 6 carbon atoms) can be exemplified. These alkyl group, alkoxyl group and alkoxycarbonyl group may further have a substituent. As the substituents that these alkyl group, alkoxyl group and alkoxycarbonyl group may further have, a hydroxyl group, a halogen atom and an alkoxyl group are exemplified.

The structures represented by formulae (pI) to (pV) in the resin can be used for the protection of alkali-soluble groups. As the alkali-soluble groups, various groups well known in this technical field can be exemplified.

Specifically, the structures in which the hydrogen atoms of a carboxylic acid group, a sulfonic acid group, a phenol group and a thiol group are substituted with the structure represented by any of formulae (pI) to (pV) are exemplified, and preferably the structures in which the hydrogen atoms of carboxylic acid group and a sulfonic acid group are substituted with the structure represented by any of formulae (pI) to (pV) are exemplified.

As the repeating unit having the alkali-soluble group protected with the structure represented by any of formulae (pI) to (pV), a repeating unit represented by the following formula (pA) is preferred.

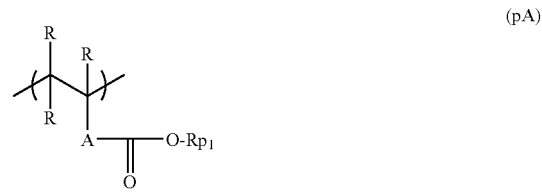

In formula (pA), R represents a hydrogen atom, a halogen atom, or a straight chain or branched alkyl group having from 1 to 4 carbon atoms, and a plurality of R's may be the same or different.

A represents a single bond, a single group or the combination of two or more groups selected from the group consisting of an alkylene group, an ether group, a thioether group, a carbonyl group, an ester group, an amido group, a sulfonamido group, a urethane group, and a urea group. A is preferably a single bond.

$R_{p1}$ represents a group represented by any of formulae (pI) to (pVI).

The repeating unit represented by (pA) is most preferably a repeating unit by 2-alkyl-2-adamantyl(meth)acrylate and dialkyl(1-adamantyl)methyl(meth)acrylate.

The specific examples of the repeating units represented by formula (pA) are shown below.

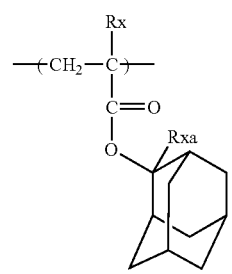

-continued
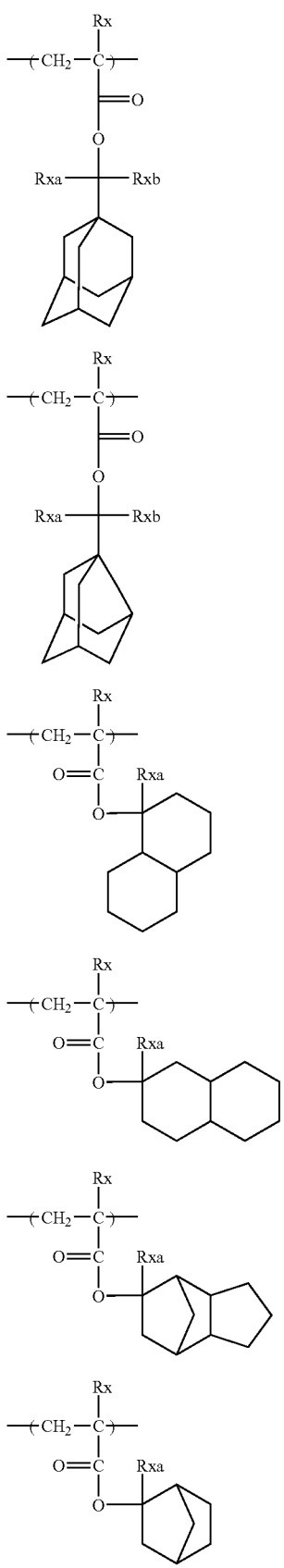
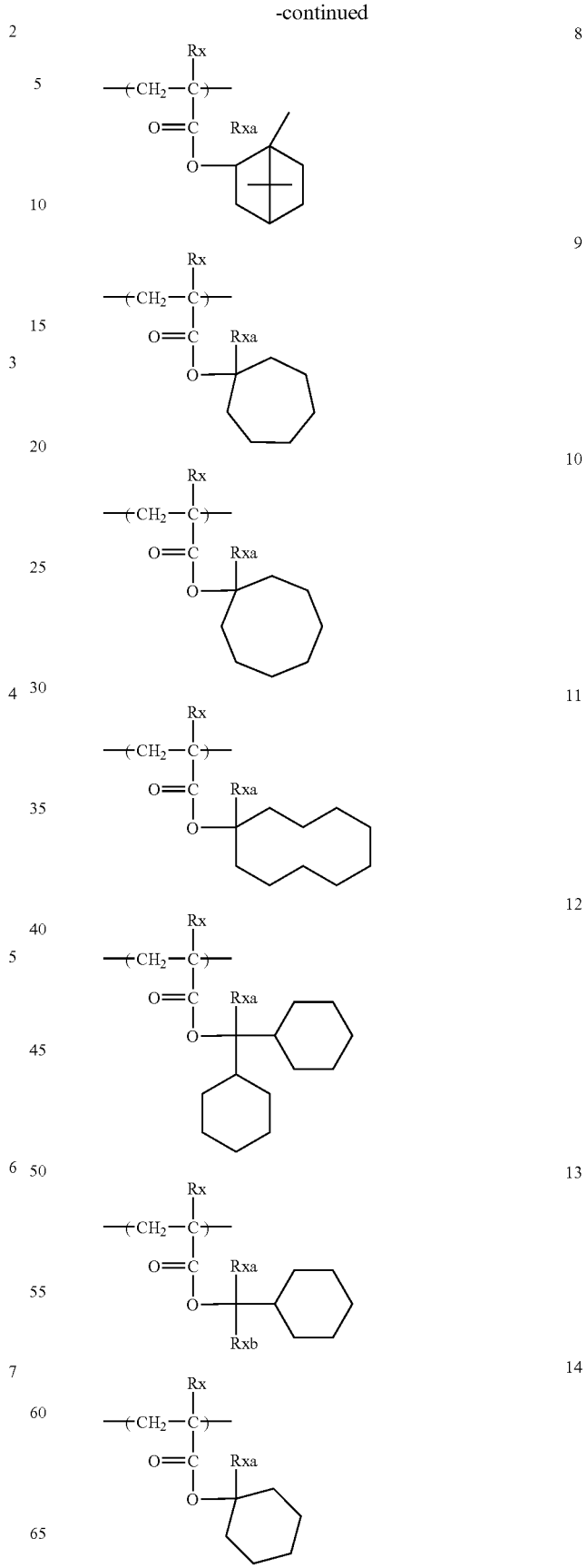

-continued

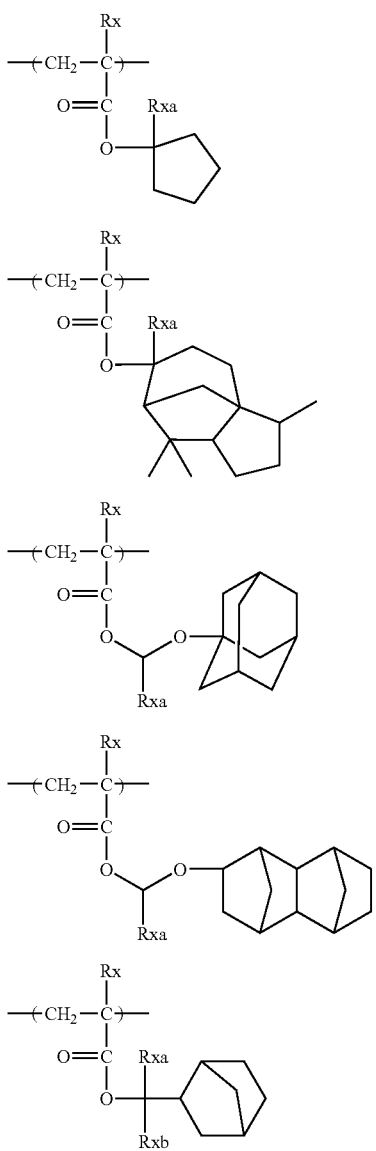

In each of the above structural formulae, Rx represents H, CH$_3$, CF$_3$ or CH$_2$OH; and Rxa and Rxb each represents an alkyl group having from 1 to 4 carbon atoms.

As the halogen atoms represented by R$_{11}$' and R$_{12}$' in formula (II-AB), a chlorine atom, a bromine atom, a fluorine atom and an iodine atom are exemplified.

As the alkyl groups represented by R$_{11}$' and R$_{12}$', straight chain or branched alkyl groups having from 1 to 10 carbon atoms are preferred, e.g., a methyl group, an ethyl group, an n-propyl group, an isopropyl group, a straight chain or branched butyl group, pentyl group, hexyl group, heptyl group, etc., are exemplified.

The atomic group represented by Z' to form an alicyclic structure is an atomic group to form a repeating unit having an alicyclic hydrocarbon structure in the resin, which may have a substituent, and an atomic group to form a repeating unit having a bridged alicyclic hydrocarbon structure is especially preferred.

As the skeleton of the alicyclic hydrocarbon to be formed, the same cycloalkyl groups as represented by R$_{12}$ to R$_{25}$ in formulae (pI) to (pVI) are exemplified.

The skeleton of the alicyclic hydrocarbon structure may have a substituent, and as the substituents, the groups represented by R$_{13}$' to R$_{16}$' in formula (II-AB1) or (II-AB2) can be exemplified.

In the alicyclic hydrocarbon-based acid-decomposable resin in the invention, a group capable of decomposing by the action of an acid can be contained in at least one repeating unit of a repeating unit having a partial structure containing alicyclic hydrocarbon represented by any of formulae (pI) to (pV), a repeating unit represented by formula (II-AB), and a repeating unit of the later-described copolymer component.

Various substituents of R$_{13}$' to R$_{16}$' in formula (II-AB1) or (II-AB2) can also be used as the substituents of the atomic group to form an alicyclic hydrocarbon structure in formula (II-AB), or atomic group Z to form a bridged alicyclic hydrocarbon structure.

The specific examples of the repeating units represented by formula (II-AB1) or (II-AB2) are shown below, but the invention is not restricted thereto.

[II-1]

[II-2]

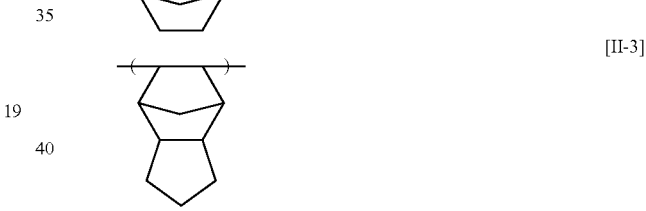

[II-3]

[II-4]

[II-5]

[II-6]

[II-7]

-continued
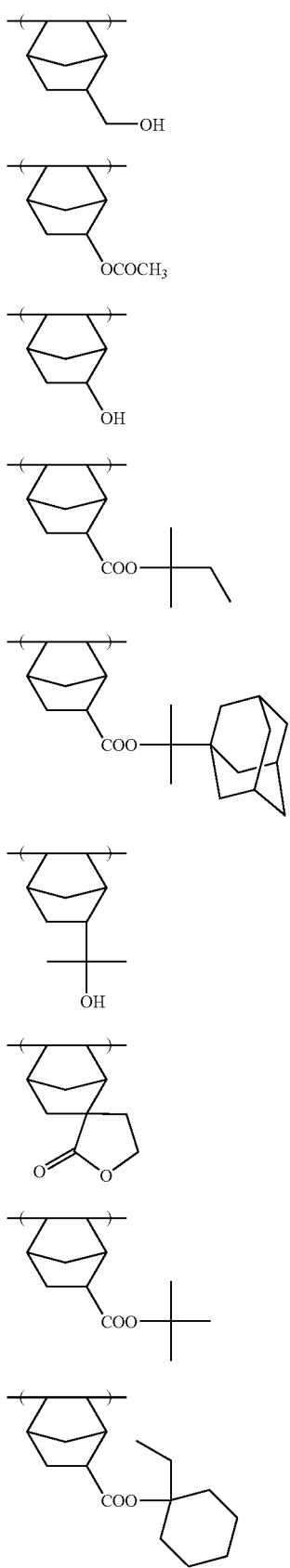
-continued
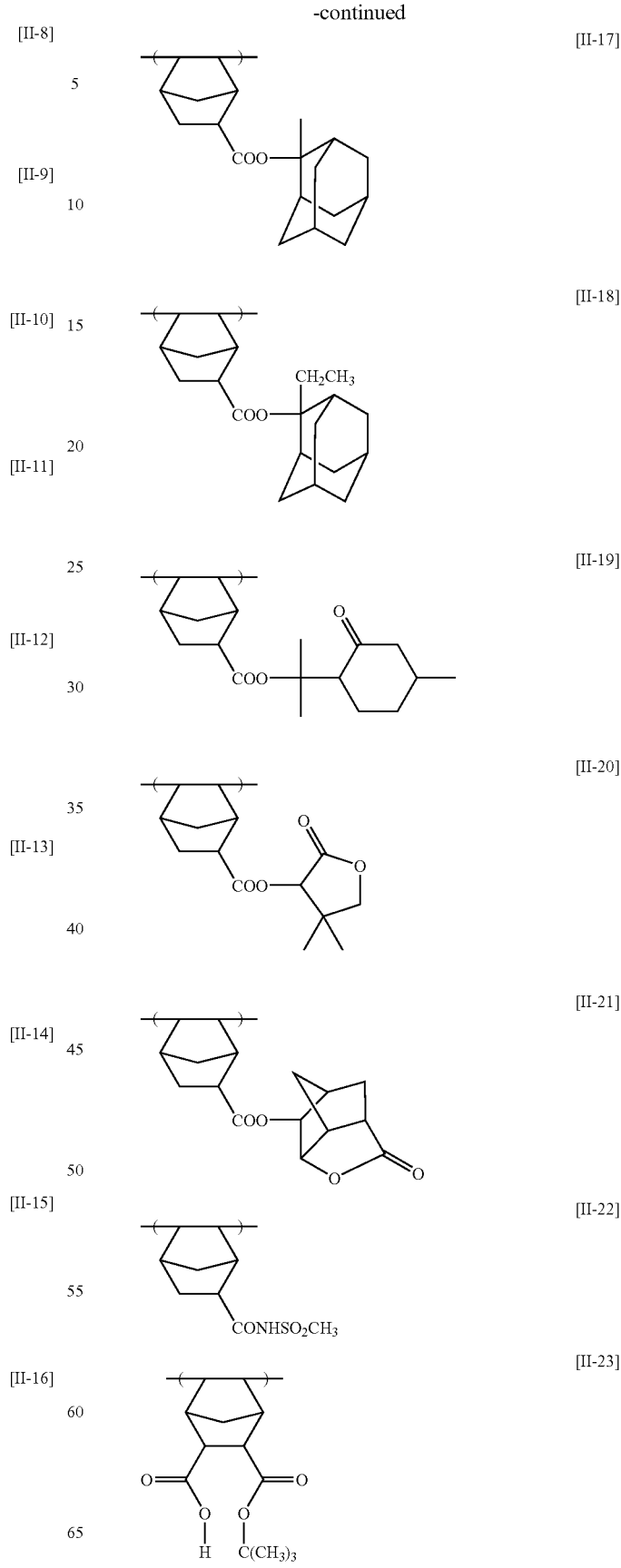

-continued

[II-24]
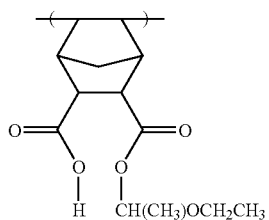

[II-25]
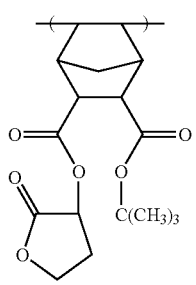

[II-26]
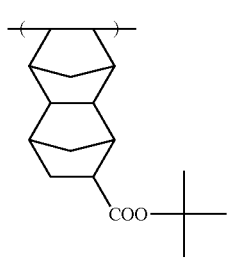

[II-27]
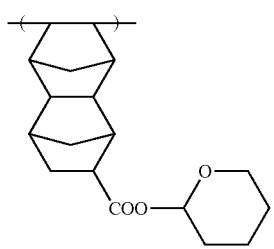

[II-28]
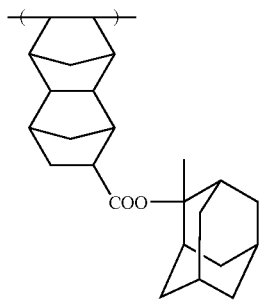

[II-29]
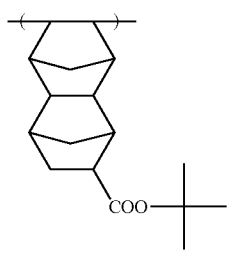

-continued

[II-30]
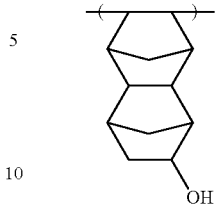

[II-31]
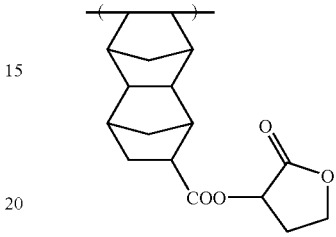

[II-32]
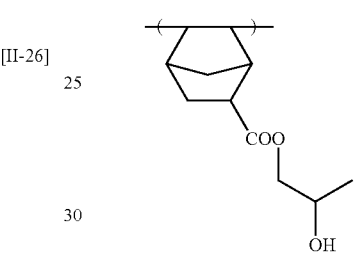

It is preferred for the alicyclic hydrocarbon-based acid-decomposable resin in the invention to have a repeating unit having a lactone group. As the lactone group, any group having a lactone structure can be used, but preferably groups having a 5- to 7-membered ring lactone structure, e.g., 5- to 7-membered ring lactone structures condensed with other ring structures in the form of forming a bicyclo structure or a spiro structure are preferred. It is more preferred for the alicyclic hydrocarbon-based acid-decomposable resin in the invention to contain a repeating unit having a group having a lactone structure represented by any of the following formulae (LC1-1) to (LC1-16). A group having a lactone structure may be directly bonded to the main chain of a repeating unit. Preferred lactone structures are (LC1-1), (LC1-4), (LC1-5), (LC1-6), (LC1-13) and (LC1-14). By the use of a specific lactone structure, line edge roughness and development defect are bettered.

LC1-1
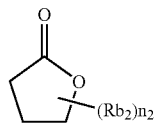

LC1-2
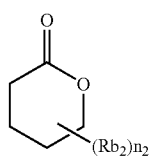

LC1-3 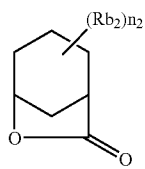

LC1-4 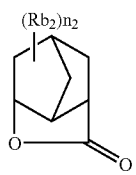

LC1-5 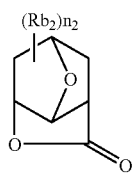

LC1-6 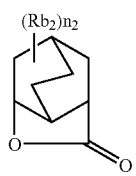

LC1-7 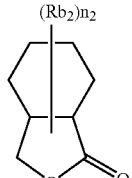

LC1-8 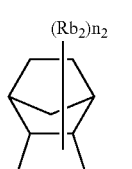

LC1-9 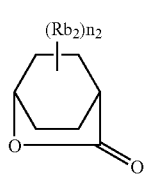

LC1-10 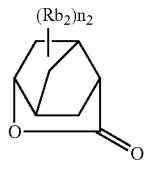

LC1-11 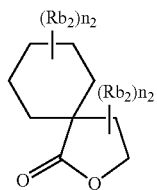

LC1-12 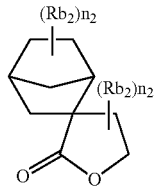

LC1-13 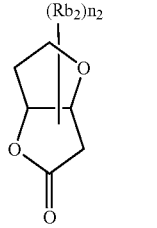

LC1-14 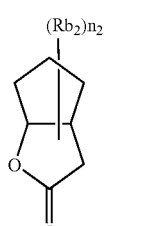

LC1-15 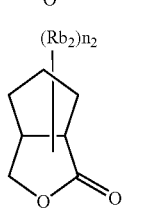

LC1-16 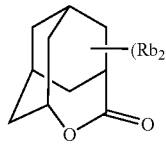

The lactone structure moiety may have or may not have a substituent ($Rb_2$). As preferred substituent ($Rb_2$), an alkyl group having from 1 to 8 carbon atoms, a cycloalkyl group having from 3 to 7 carbon atoms, an alkoxyl group having from 1 to 8 carbon atoms, an alkoxycarbonyl group having from 1 to 8 carbon atoms, a carboxyl group, a halogen atom, a hydroxyl group, a cyano group, and an acid-decomposable group are exemplified. $n_2$ represents an integer of from 0 to 4. When $n_2$ is an integer of 2 or more, a plurality of $Rb_2$ may be the same or different, and a plurality of $Rb_2$ may be bonded to each other to form a ring.

As the repeating units having a group having a lactone structure represented by any of formulae (LC1-1) to (LC1-16), a repeating unit represented by formula (II-AB1) or (II-AB2) in which at least one of $R_{13}'$ to $R_{16}'$ is a group having a lactone structure represented by any of formulae (LC1-1) to (LC1-16) (for example, $R_5$ of —$COOR_5$ is a group represented by any of formulae (LC1-1) to (LC1-16)), or a repeating unit represented by the following formula (AI) can be exemplified.

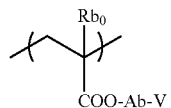

(AI)

In formula (AI), $Rb_0$ represents a hydrogen atom, a halogen atom, or an alkyl group having from 1 to 4 carbon atoms.

As the alkyl group represented by $Rb_0$, e.g., a methyl group, an ethyl group, a propyl group, an n-butyl group, a sec-butyl group, a t-butyl group and the like can be exemplified. The alkyl group represented by $Rb_0$ may have a substituent. As the preferred substituents that the alkyl group represented by $Rb_0$ may have, e.g., a hydroxyl group and a halogen atom are exemplified.

As the halogen atom represented by $Rb_0$, a fluorine atom, a chlorine atom, a bromine atom and an iodine atom can be exemplified. $Rb_0$ preferably represents a hydrogen atom or a methyl group.

Ab represents an alkylene group, a divalent linking group having a monocyclic or polycyclic alicyclic hydrocarbon structure, a single bond, an ether group, an ester group, a carbonyl group, a carboxyl group, or a divalent linking group obtained by combining these groups. Ab preferably represents a single bond or a linking group represented by —$Ab_1$—$CO_2$—.

$Ab_1$ represents a straight chain or branched alkylene group, or a monocyclic or polycyclic cycloalkylene group, and preferably a methylene group, an ethylene group, a cyclohexyl residue, an adamantyl residue, or a norbornyl residue.

V represents a group represented by any of formulae (LC1-1) to (LC1-16).

Repeating units having a lactone structure generally have optical isomers, and any optical isomer may be used. One kind of optical isomer may be used alone, or a plurality of optical isomers may be used as mixture. When one kind of optical isomer is mainly used, the optical purity (ee) of the optical isomer is preferably 90 or more, and more preferably 95 or more.

The specific examples of the repeating units having a group having a lactone structure are shown below, but the invention is not restricted to these compounds.

(In the formulae, Rx represents H, $CH_3$, $CH_2OH$ or $CF_3$.)

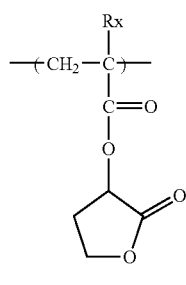 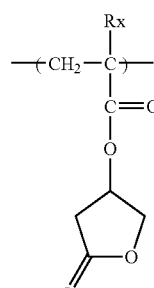 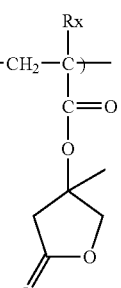

-continued

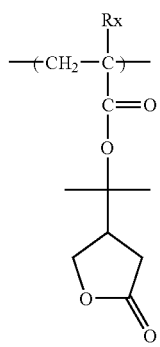 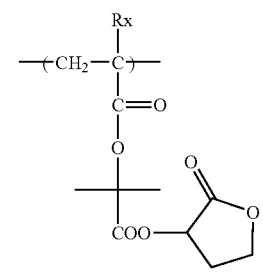

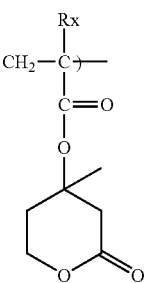 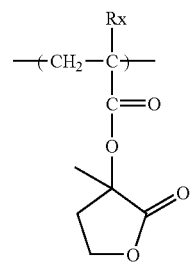 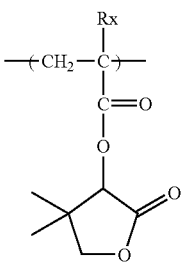

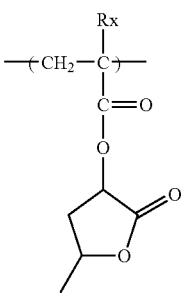 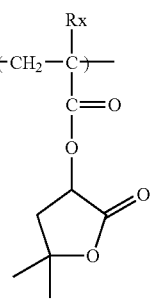 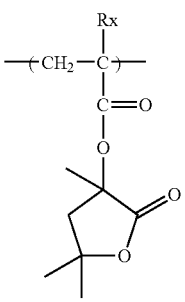

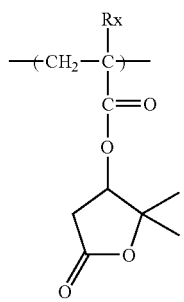 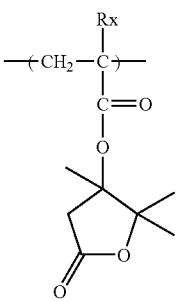

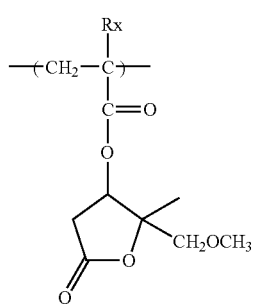 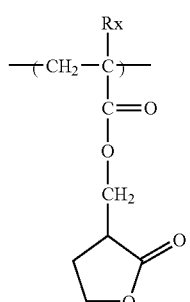

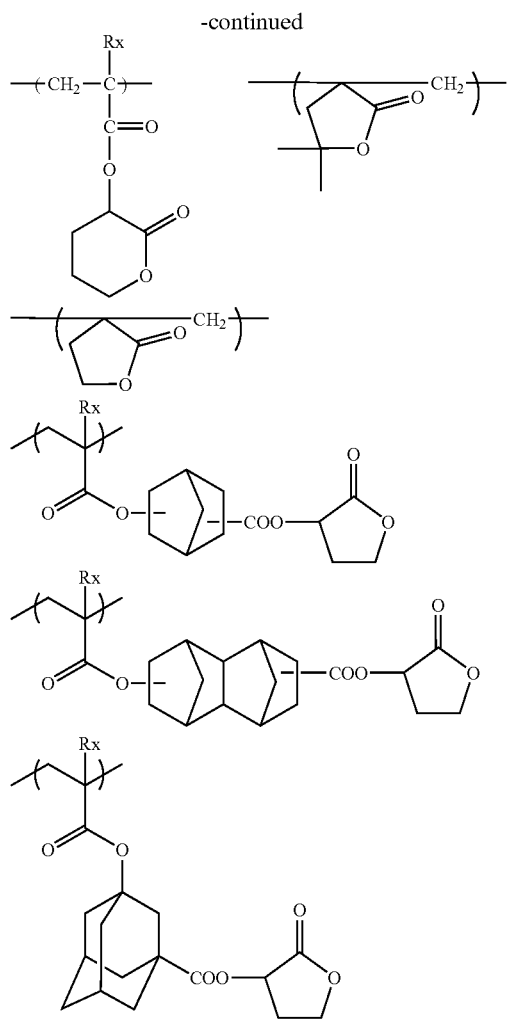
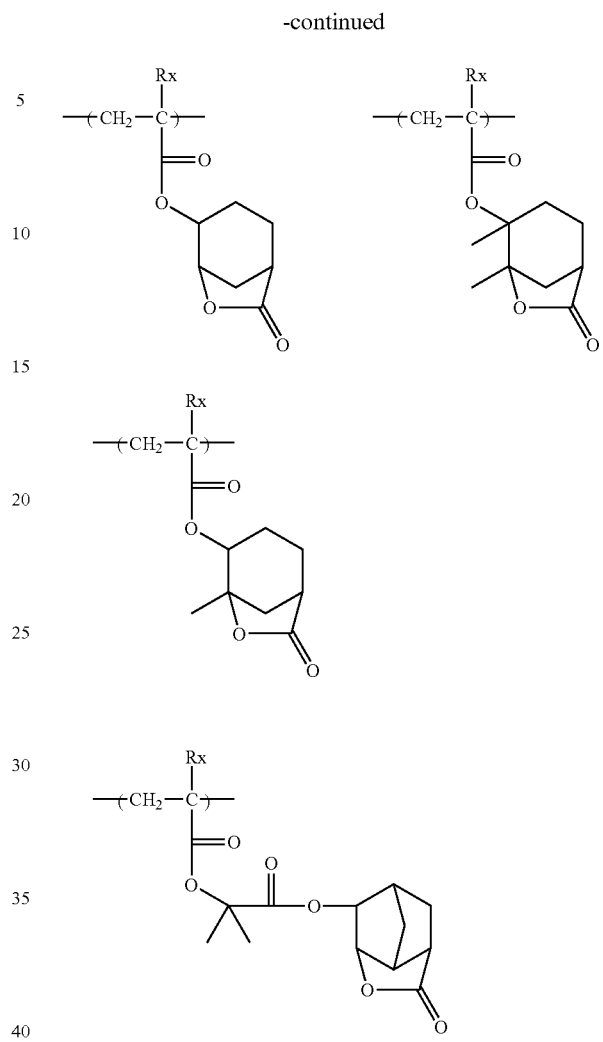
(In the formulae, Rx represents H, CH$_3$, CH$_2$OH or CF$_3$.)
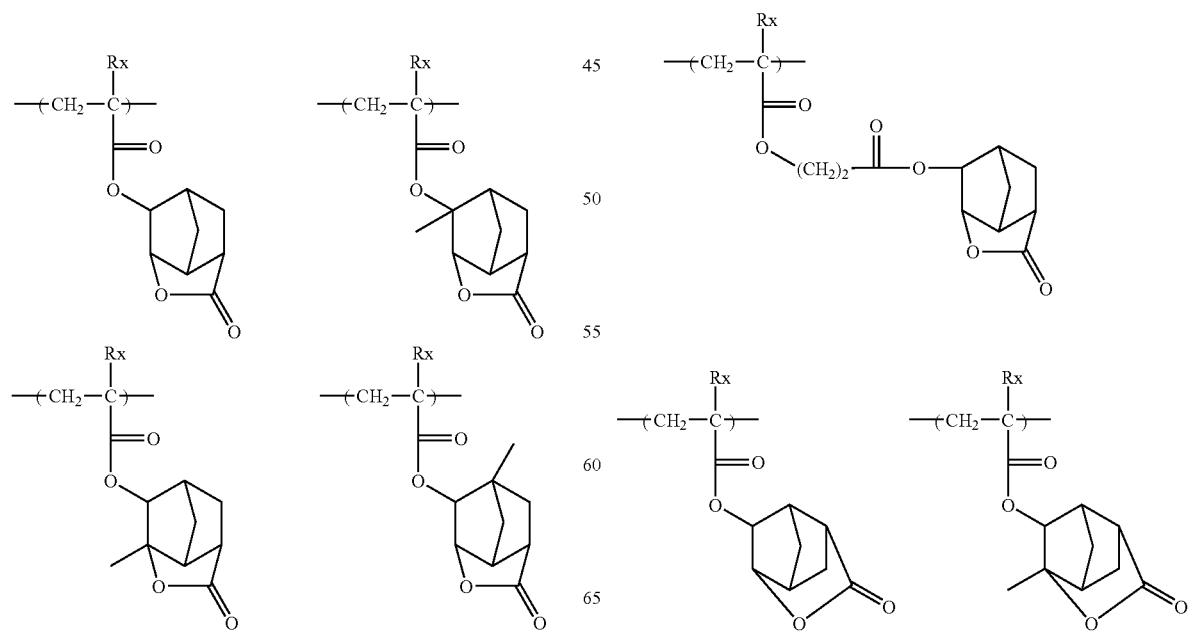

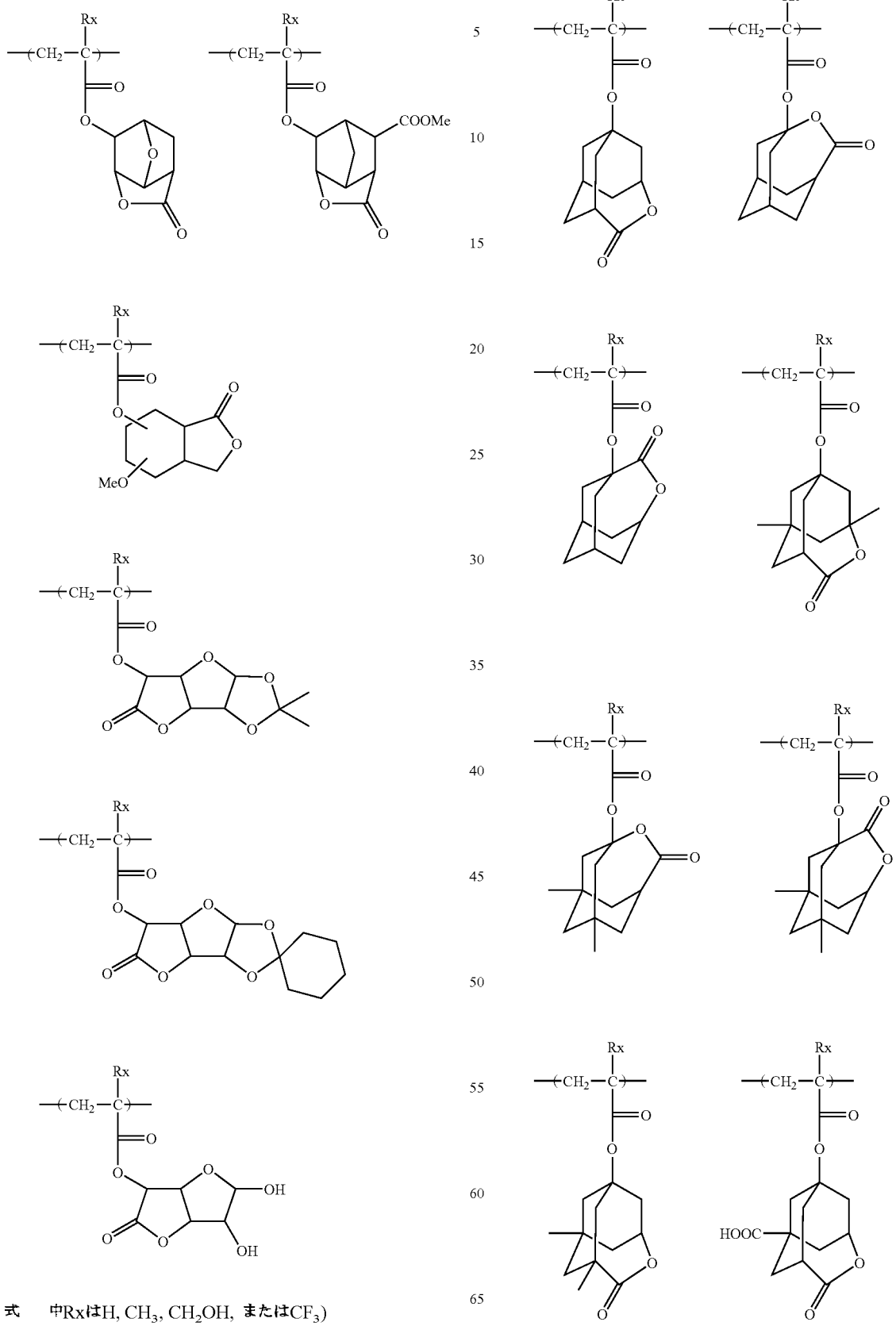
式中Rxは H, CH₃, CH₂OH, または CF₃)

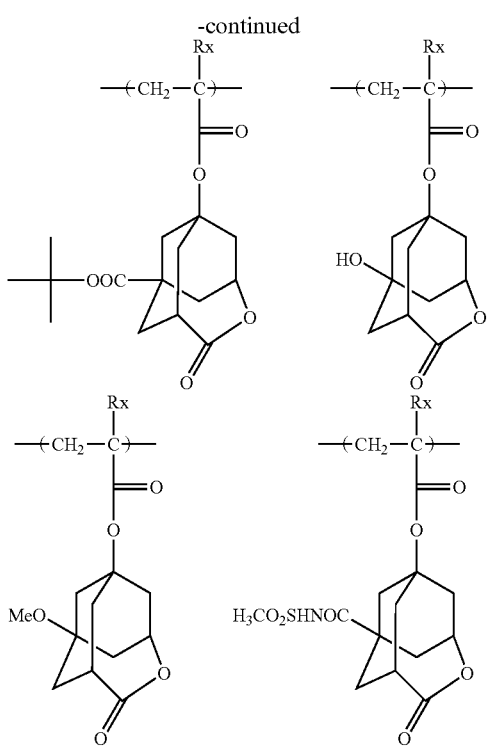

It is preferred for the alicyclic hydrocarbon-based acid-decomposable resin in the invention to have a repeating unit having an alicyclic hydrocarbon structure substituted with a polar group, by which adhesion with a substrate and affinity with a developing solution are improved. As the polar group, a hydroxyl group and a cyano group are preferred.

The hydroxyl group as the polar group forms an alcoholic hydroxyl group.

As the alicyclic hydrocarbon structure substituted with a polar group, a structure represented by the following formula (VIIa) or (VIIb) is exemplified.

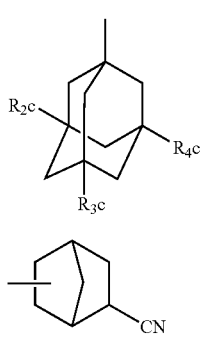

In formula (VIIa), $R_{2c}$, $R_{3c}$ and $R_{4c}$ each represents a hydrogen atom, a hydroxyl group, or a cyano group, provided that at least any one of $R_{2c}$, $R_{3c}$ and $R_{4c}$ represents a hydroxyl group or a cyano group. Preferably one or two of $R_{2c}$, $R_{3c}$ and $R_{4c}$ represent a hydroxyl group and the remainder represents a hydrogen atom, and more preferably two of $R_{2c}$, $R_{3c}$ and $R_{4c}$ represent a hydroxyl group and the remainder represents a hydrogen atom.

The group represented by formula (VIIa) is preferably dihydroxy or monohydroxy, and more preferably dihydroxy.

As the repeating unit having the group represented by formula (VIIa) or (VIIb), a repeating unit represented by formula (II-AB1) or (II-AB2) in which at least any one of $R_{13}'$ to $R_{16}'$ is a group having a structure represented by formula (VIIa) or (VIIb) (for example, $R_5$ of —COOR$_5$ is a group represented by formula (VIIa) or (VIIb)), or a repeating unit represented by the following formula (AIIa) or (AIIb) can be exemplified.

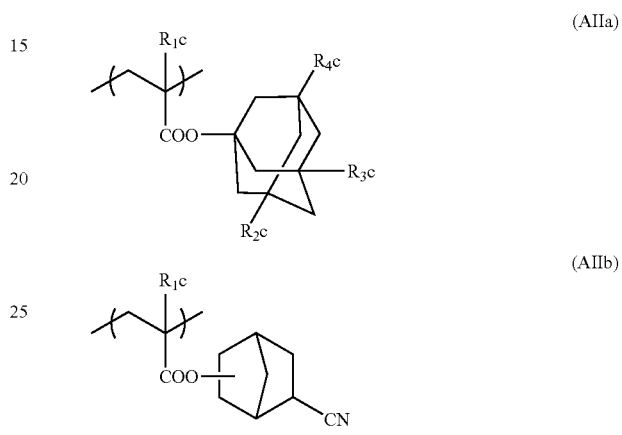

In formulae (AIIa) and (AIIb), $R_{1c}$ represents a hydrogen atom, a methyl group, a trifluoromethyl group, or a hydroxymethyl group.

$R_{2c}$, $R_{3c}$ and $R_{4c}$ each has the same meaning as $R_{2c}$, $R_{3c}$ and $R_{4c}$ in formula (VIIa).

The specific examples of the repeating units having an alicyclic hydrocarbon structure substituted with a polar group represented by formulae (AIIa) or (AIIb) are shown below, but the invention is not restricted thereto.

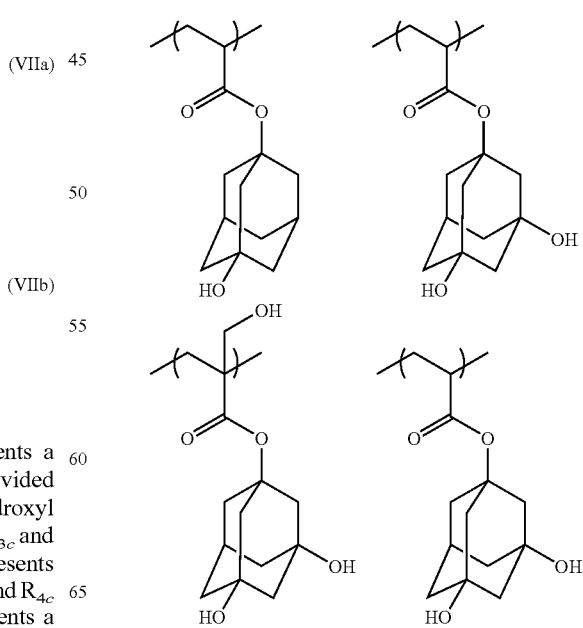

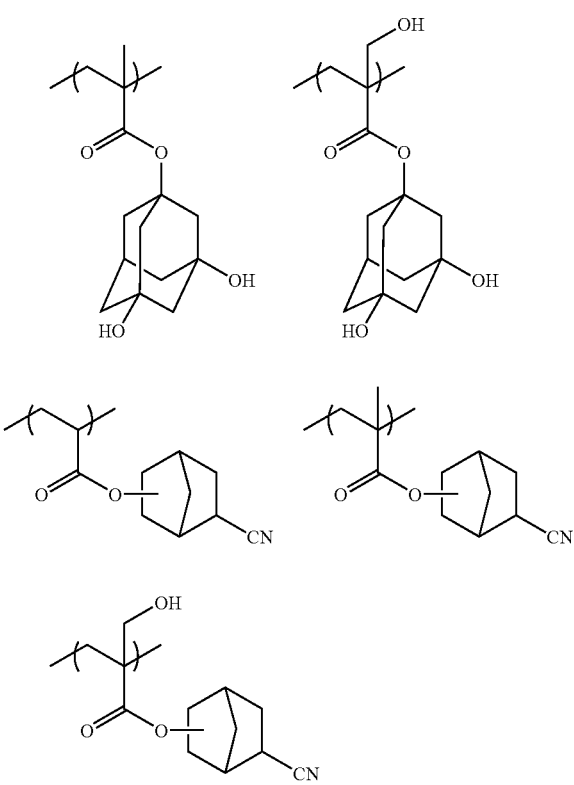

The alicyclic hydrocarbon-based acid-decomposable resin in the invention may have a repeating unit represented by the following formula (VIII).

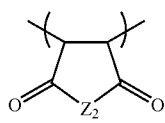
(VIII)

In formula (VIII), $Z_2$ represents —O— or —N($R_{41}$)—. $R_{41}$ represents a hydrogen atom, a hydroxyl group, an alkyl group, or —OSO$_2$—$R_{42}$. $R_{42}$ represents an alkyl group, a cycloalkyl group, or a camphor residue. The alkyl group represented by $R_{41}$ and $R_{42}$ may be substituted with a halogen atom (preferably a fluorine atom) and the like.

As the specific examples of the repeating units represented by formula (VIII), the following compounds are exemplified, but the invention is not restricted thereto.

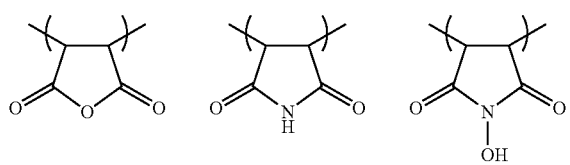

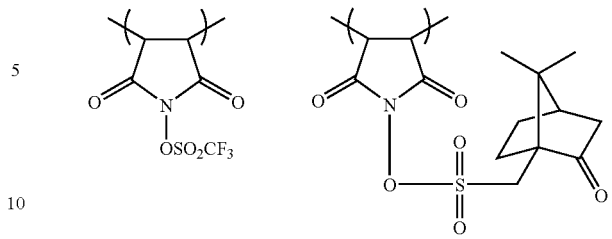

It is preferred for the alicyclic hydrocarbon-based acid-decomposable resin in the invention to have a repeating unit having an alkali-soluble group, and it is more preferred to have a repeating unit having a carboxyl group, by which the resolution in the use for contact hole is enhanced. As the repeating units having a carboxyl group, both a repeating unit having a carboxyl group directly bonded to the main chain of resin such as a repeating unit by acrylic acid or methacrylic acid, and a repeating unit having a carboxyl group bonded to the main chain of resin via a linking group are preferred, and the linking group may have a monocyclic or polycyclic hydrocarbon structure. The repeating unit by acrylic acid or methacrylic acid is most preferred.

The alicyclic hydrocarbon-based acid-decomposable resin in the invention may have a repeating unit having one to three groups represented by the following formula (F1), by which line edge roughness property is improved.

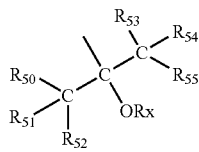
(F1)

In formula (F1), $R_{50}$, $R_{51}$, $R_{52}$, $R_{53}$, $R_{54}$ and $R_{55}$ each represents a hydrogen atom, a fluorine atom, or an alkyl group, provided that at least any one of $R_{50}$ to $R_{55}$ represents a fluorine atom, or an alkyl group in which at least one hydrogen atom is substituted with a fluorine atom.

Rx represents a hydrogen atom or an organic group (preferably an acid-decomposable protective group, an alkyl group, a cycloalkyl group, an acyl group, or an alkoxycarbonyl group).

The alkyl group represented by $R_{50}$ to $R_{55}$ may be substituted with a halogen atom, e.g., a fluorine atom, or a cyano group, and preferably an alkyl group having from 1 to 3 carbon atoms, e.g., a methyl group and a trifluoromethyl group can be exemplified.

It is preferred that all of $R_{50}$ to $R_{55}$ represent a fluorine atom.

As the organic group represented by Rx, an acid-decomposable protective group, and an alkyl group, a cycloalkyl group, an acyl group, an alkylcarbonyl group, an alkoxycarbonyl group, an alkoxycarbonylmethyl group, an alkoxymethyl group, and a 1-alkoxyethyl group, each of which may have a substituent, are preferred.

The repeating unit having the group represented by formula (F1) is preferably a repeating unit represented by the following formula (F2).

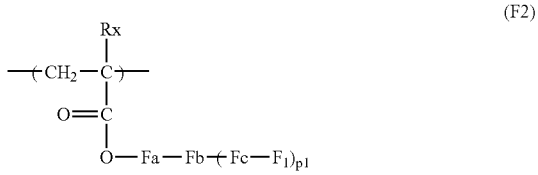

In formula (F2), Rx represents a hydrogen atom, a halogen atom, or an alkyl group having from 1 to 4 carbon atoms. As preferred substituents that the alkyl group represented by Rx may have, a hydroxyl group and a halogen atom are exemplified.

Fa represents a single bond or a straight chain or branched alkylene group, and preferably a single bond.

Fb represents a monocyclic or polycyclic hydrocarbon group.

Fc represents a single bond or a straight chain or branched alkylene group, and preferably a single bond or a methylene group.

$F_1$ represents a group represented by formula (F1).

$P_1$ represents from 1 to 3.

As the cyclic hydrocarbon group represented by Fb, a cyclopentyl group, a cyclohexyl group, or a norbornyl group is preferred.

The specific examples of the repeating units having the structure represented by formula (F1) are shown below.

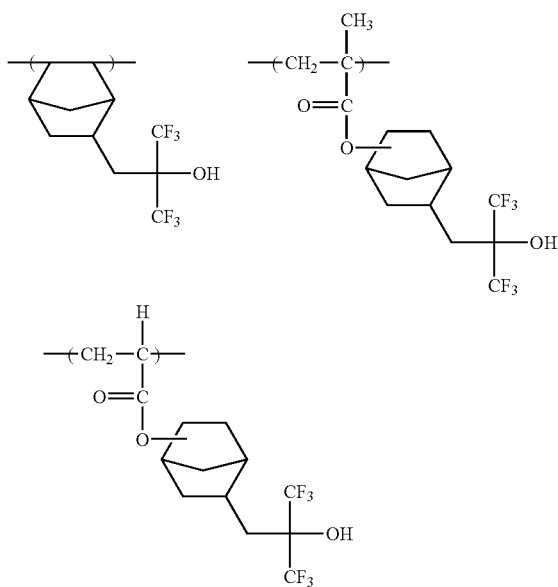

The alicyclic hydrocarbon-based acid-decomposable resin in the invention can contain various kinds of repeating structural units, besides the above repeating structural units, for the purpose of the adjustments of dry etching resistance, aptitude for standard developing solutions, adhesion to a substrate, resist profile, and further, general requisite performances of resists, e.g., resolution, heat resistance and sensitivity.

As these repeating structural units, the repeating structural units corresponding to the monomers shown below can be exemplified, but the invention is not restricted thereto.

By containing such various repeating structural units, fine adjustment of performances required of the alicyclic hydrocarbon-based acid-decomposable resin, in particular the following performances, becomes possible, that is, (1) Solubility in a coating solvent, (2) A film-forming property (a glass transition point), (3) Alkali developability, (4) Decrease of layer thickness (hydrophobic/hydrophilic properties, selection of an alkali-soluble group), (5) Adhesion of an unexposed area to a substrate, and (6) Dry etching resistance.

The examples of such monomers include compounds having one addition polymerizable unsaturated bond selected from acrylic esters, methacrylic esters, acrylamides, methacryl-amides, allyl compounds, vinyl ethers, vinyl esters, etc.

In addition to the aforementioned compounds, addition polymerizable unsaturated compounds copolymerizable with the monomers corresponding to the above various repeating structural units may be used for copolymerization.

In the alicyclic hydrocarbon-based acid-decomposable resin, the molar ratio of the content of each repeating structural unit is arbitrarily set to adjust dry etching resistance, aptitude for standard developing solutions of a resist, adhesion to a substrate, and resist profile, in addition, general requisite performances of a resist, e.g., resolution, heat resistance and sensitivity.

As preferred embodiments of the alicyclic hydrocarbon-based acid-decomposable resin in the invention, the following resins are exemplified.

(1) Resin containing a repeating unit having a partial structure containing the alicyclic hydrocarbon represented by any of formulae (pI) to (pV) (a side chain type), preferably resin containing a repeating unit by (meth)acrylate having the structure of any of formulae (pI) to (pV), (2) Resin containing a repeating unit represented by formula (II-AB) (a main chain type); however, the following is further exemplified as embodiment (2), (3) Resin containing a repeating unit represented by formula (II-AB), a maleic anhydride derivative structure and a (meth) acrylate structure (a hybrid type).

In the alicyclic hydrocarbon-based acid-decomposable resin, the content of a repeating unit having an acid-decomposable group is preferably from 10 to 60 mol % in all the repeating structural units, more preferably from 20 to 50 mol %, and still more preferably from 25 to 40 mol %.

In the alicyclic hydrocarbon-based acid-decomposable resin, the content of a repeating unit having a partial structure containing the alicyclic hydrocarbon represented by any of formulae (pI) to (pV) is preferably from 25 to 70 mol % in all the repeating structural units, more preferably from 35 to 65 mol %, and still more preferably from 40 to 60 mol %.

In the alicyclic hydrocarbon-based acid-decomposable resin, the content of a repeating unit represented by formula (II-AB) is preferably from 10 to 60 mol % in the total repeating structural units, more preferably from 15 to 55 mol %, and still more preferably from 20 to 50 mol %.

The content of the repeating unit having a lactone group is preferably from 10 to 70 mol % in all the repeating structural units, more preferably from 20 to 60 mol %, and still more preferably from 25 to 60 mol %.

The content of the repeating unit having the alicyclic hydrocarbon structure substituted with a polar group is preferably from 1 to 40 mol % in all the repeating structural units, more preferably from 5 to 30 mol %, and still more preferably from 5 to 20 mol %.

The content of the repeating structural units on the basis of the monomers of further copolymerization components in the resin can also be optionally set according to the desired resist performances, and the content is preferably 99 mol % or less to the sum total of the mol number of the repeating structural units having a partial structure containing the alicyclic hydrocarbon represented by any of formulae (PI) to (pV) and the repeating units represented by formula (II-AB), more preferably 90 mol % or less, and still more preferably 80 mol % or less.

When the composition in the invention is used for ArF exposure, it is preferred that the resin does not have an aromatic group from the aspect of the transparency to ArF rays.

The alicyclic hydrocarbon-based acid-decomposable resin for use in the invention is preferably such that all the repeating units consist of (meth)acrylate repeating units. In this case, any of the following cases can be used, that is, a case where all the repeating units consist of methacrylate, a case where all the repeating units consist of acrylate, and a case where the repeating units consist of mixture of methacrylate and acrylate, but it is preferred that acrylate repeating units account for 50 mol % or less of all the repeating units.

More preferred resins are terpolymers comprising from 25 to 50% of the repeating unit having a partial structure containing the alicyclic hydrocarbon represented by any of formulae (pI) to (pV), from 25 to 50 mol % of the repeating unit having the lactone structure, and from 5 to 30% of the repeating unit having the alicyclic hydrocarbon structure substituted with a polar group, and tetrapolymers further containing from 5 to 20% of the repeating units having a carboxyl group or the structure represented by formula (F1).

The alicyclic hydrocarbon-based acid-decomposable resins for use in the invention can be synthesized according to ordinary methods (e.g., radical polymerization). For instance, as ordinary methods, a batch polymerization method of dissolving a monomer and an initiator in a solvent and heating the solution to perform polymerization, and a dropping polymerization method of adding a solution of a monomer and an initiator to a heated solvent over 1 to 10 hours by dropping are exemplified, and dropping polymerization is preferred. As reaction solvents, ethers, e.g., tetrahydrofuran, 1,4-dioxane, and diisopropyl ether, ketones, e.g., methyl ethyl ketone and methyl isobutyl ketone, an ester solvent, e.g., ethyl acetate, amide solvents, e.g., dimethylformamide and dimethyacetamide, and the later-described solvents capable of dissolving the composition of the invention, e.g., propylene glycol monomethyl ether acetate, propylene glycol monomethyl ether, and cyclohexanone are exemplified. It is more preferred to use the same solvent in polymerization as the solvent used in the photosensitive composition in the invention, by which the generation of particles during preservation can be restrained.

It is preferred to perform polymerization reaction in the atmosphere of inert gas such as nitrogen or argon. Polymerization is initiated with commercially available radical initiators (e.g., azo initiators, peroxide and the like). As the radical initiators, azo initiators are preferred, and azo initiators having an ester group, a cyano group, or a carboxyl group are preferred. As preferred initiators, azobisisobutyronitrile, azobisdimethylvalero-nitrile, dimethyl-2,2'-azibis(2-methylpropionate) and the like are exemplified. Initiators are added additionally or dividedly, if desired, and after termination of the reaction, the reaction product is put into a solvent and an objective polymer is recovered as powder or a solid state. The reaction concentration is from 5 to 50 mass %, and preferably from 10 to 30 mass %. The reaction temperature is generally from 10 to 150° C., preferably from 30 to 120° C., and more preferably from 50 to 100° C.

When the photosensitive composition according to the invention is used in the upper layer resist of a multilayer resist, it is preferred that resin (C) should have a silicon atom.

As resins having a silicon atom and capable of decomposing by the action of an acid to thereby increase the solubility in an alkali developing solution, resins having a silicon atom at least on one side of the main chain and the side chain can be used. As resins having a siloxane structure on the side chain of resins, copolymers of, e.g., an olefin monomer having a silicon atom on the side chain, and a (meth)acrylic acid monomer having maleic anhydride and an acid decomposable group on the side chain.

As resins having a silicon atom, resins having a trialkylsilyl structure, and a monocyclic or polycyclic siloxane structure are preferred, resins having repeating units having the structures represented by any of the following formulae (SS-1) to (SS-4) are more preferred, and resins having (meth)acrylic ester repeating units having the structures represented by any of formulae (SS-1) to (SS-4), vinyl repeating units, and allyl repeating units are still more preferred.

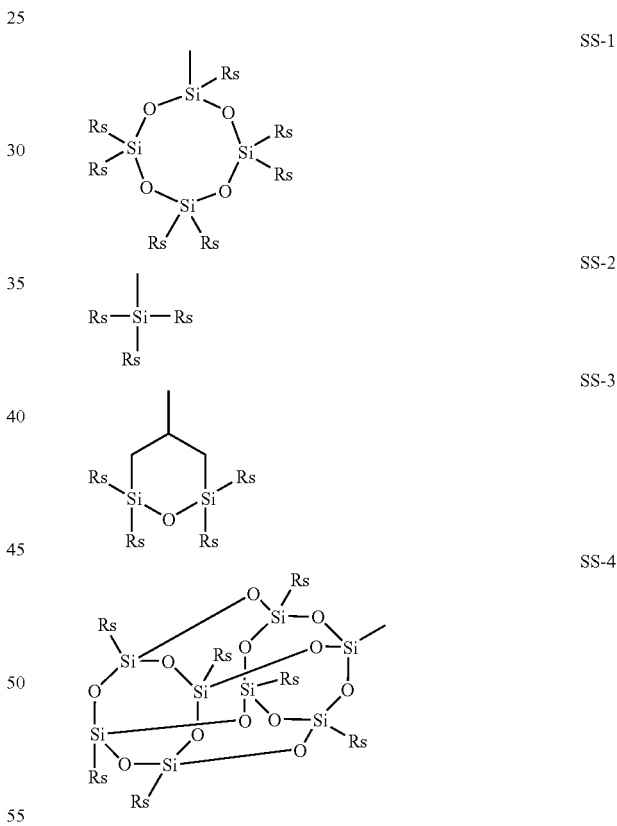

In formulae (SS-1) to (SS-4), Rs represents an alkyl group having from 1 to 5 carbon atoms, preferably a methyl group or an ethyl group.

It is preferred that resins having silicon atoms have two or more kinds of different repeating units having silicon atoms, resins having both (Sa) repeating unit having from 1 to 4 silicon atoms and (Sb) repeating unit having from 5 to 10 silicon atoms are more preferred, and resins having at least one repeating unit having a structure represented by any of formulae (SS-1) to (SS-3) and a repeating unit having a structure represented by formula (SS-4) are still more preferred.

When the positive photosensitive composition of the invention is irradiated with $F_2$ excimer laser beams, the resin of component (C) is preferably a resin having a structure wherein the main chain and/or side chain of the polymer skeleton are substituted with fluorine atoms and capable of decomposing by the action of an acid to increase the solubility in an alkali developing solution (hereinafter also referred to as "a fluorine-based acid-decomposable resin), the resin is more preferably a resin having a hydroxyl group the 1-position of which is substituted with a fluorine atom or a fluoroalkyl group, or having a group obtained by protecting a hydroxyl group, the 1-position of which is substituted with a fluorine atom or a fluoroalkyl group, with an acid-decomposable group. The especially preferred resin is a resin having a hexafluoro-2-propanol structure, or a resin having a structure that the hydroxyl group of hexafluoro-2-propanol is protected with an acid-decomposable group. By the introduction of fluorine atoms, the transparency to the far ultraviolet rays, in particular to $F_2$ ray (157 nm), can be improved.

As the fluorine-based acid-decomposable resin, resins having at least one repeating unit represented by any of the following formulae (FA) to (FG) are preferably exemplified.

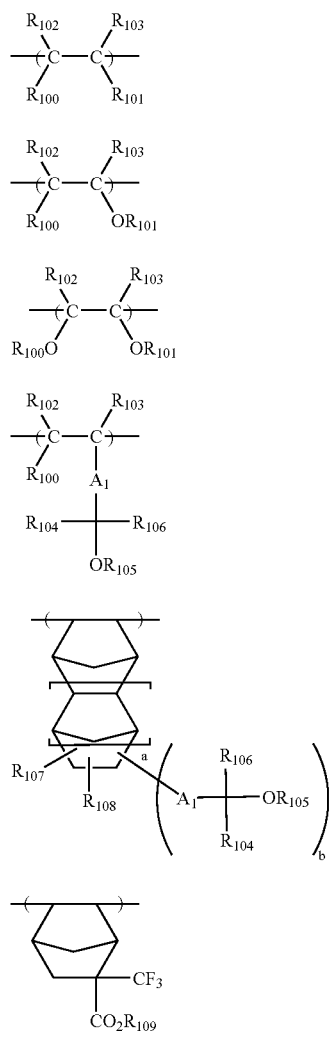

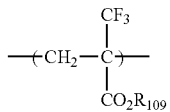

In the above formulae, $R_{100}$, $R_{101}$, $R_{102}$ and $R_{103}$ each represents a hydrogen atom, a fluorine atom, an alkyl group, or an aryl group.

$R_{104}$ and $R_{106}$ each represents a hydrogen atom, a fluorine atom, or an alkyl group, and at least one of $R_{104}$ and $R_{106}$ represents a fluorine atom or a fluoroalkyl group. Preferably both $R_{104}$ and $R_{106}$ represent a trifluoromethyl group.

$R_{105}$ represents a hydrogen atom, an alkyl group, a cycloalkyl group, an acyl group, an alkoxycarbonyl group, or a group decomposable by the action of an acid.

$A_1$ represents a single bond, a divalent linking group, e.g., an alkylene group, a cycloalkylene group, an alkenylene group, an arylene group, —OCO—, —COO—, —CON($R_{24}$)—, or a linking group containing a plurality of these groups. $R_{24}$ represents a hydrogen atom or an alkyl group.

$R_{107}$ and $R_{108}$ each represents a hydrogen atom, a halogen atom, an alkyl group, an alkoxyl group, an alkoxycarbonyl group, or a group decomposable by the action of an acid.

$R_{109}$ represents a hydrogen atom, an alkyl group, a cycloalkyl group, or a group decomposable by the action of an acid.

b represents 0, 1 or 2.

Further, $R_{100}$ and $R_{101}$ in formulae (FA) and (FC) may form a ring via an alkylene group (having from 1 to 5 carbon atoms) that may be substituted with a fluorine atom.

The repeating units represented by any of formulae (FA) to (FG) have at least 1, preferably 3 or more, fluorine atoms per one repeating unit.

In formulae (FA) to (FG), the alkyl group is, e.g., an alkyl group having from 1 to 8 carbon atoms, specifically, a methyl group, an ethyl group, a propyl group, an n-butyl group, a sec-butyl group, a hexyl group, a 2-ethylhexyl group, and an octyl group are preferably exemplified.

The cycloalkyl group may be monocyclic or polycyclic. As the monocyclic cycloalkyl groups, cycloalkyl groups having from 3 to 8 carbon atoms, e.g., a cyclopropyl group, a cyclopentyl group, a cyclohexyl group, a cycloheptyl group, and a cyclooctyl group are preferably exemplified. As the polycyclic groups, cycloalkyl groups having from 6 to 20 carbon atoms, e.g., an adamantyl group, a norbornyl group, an isoboronyl group, a camphanyl group, a dicyclopentyl group, an α-pinel group, a tricyclodecanyl group, a tetracyclododecyl group, and an androstanyl group are preferably exemplified. However, the carbon atoms in the monocyclic or polycyclic cycloalkyl groups may be substituted with a hetero atom such as an oxygen atom, etc.

The fluoroalkyl group is, e.g., a fluoroalkyl group having from 1 to 12 carbon atoms, and specifically a trifluoromethyl group, a perfluoroethyl group, a perfluoropropyl group, a perfluorobutyl group, a perfluorohexyl group, a perfluorooctyl group, a perfluorooctylethyl group, and a perfluorododecyl group are preferably exemplified.

The aryl group is, e.g., an aryl group having from 6 to 15 carbon atoms, and specifically a phenyl group, a tolyl group, a dimethylphenyl group, a 2,4,6-trimethylphenyl group, a naphthyl group, an anthryl group, and a 9,10-dimethoxyanthryl group are preferably exemplified.

The alkoxyl group is, e.g., an alkoxyl group having from 1 to 8 carbon atoms, and specifically a methoxy group, an ethoxy group, an n-propoxy group, an isopropoxy group, a butoxy group, a pentoxy group, an allyloxy group, and an octoxy group are preferably exemplified.

The acyl group is, e.g., an acyl group having from 1 to 10 carbon atoms, and specifically a formyl group, an acetyl group, a propanoyl group, a butanoyl group, a pivaloyl group, an octanoyl group, and a benzoyl group are preferably exemplified.

As the alkoxycarbonyl group, an i-propoxycarbonyl group, a t-butoxycarbonyl group, a t-amyloxycarbonyl group, and a 1-methyl-1-cyclohexyloxycarbonyl group are exemplified, preferably a secondary, and more preferably a tertiary alkoxycarbonyl group are exemplified.

As the halogen atom, e.g., a fluorine atom, a chlorine atom, a bromine atom and an iodine atom are exemplified.

As the alkylene group, preferably an alkylene group having from 1 to 8 carbon atoms, e.g., a methylene group, an ethylene group, a propylene group, a butylene group, a hexylene group, and an octylene group are exemplified.

As the alkenylene group, preferably an alkenylene group having from 2 to 6 carbon atoms, e.g., an ethenylene group, a propenylene group and a butenylene group are exemplified.

As the cycloalkylene group, preferably a cycloalkylene group having from 5 to 8 carbon atoms, e.g., a cyclopentylene group and a cyclohexylene group are exemplified.

As the arylene group, preferably an arylene group having from 6 to 15 carbon atoms, e.g., a phenylene group, a tolylene group and a naphthylene group are exemplified.

These groups may have a substituent, and the examples of the substituents include groups having active hydrogen, e.g., an alkyl group, a cycloalkyl group, an aryl group, an amino group, an amido group, a ureido group, a urethane group, a hydroxyl group, and a carboxyl group; a halogen atom (e.g., a fluorine atom, a chlorine atom, a bromine atom, an iodine atom), an alkoxyl group (e.g., a methoxy group, an ethoxy group, a propoxy group, a butoxy group), a thioether group, an acyl group (e.g., an acetyl group, a propanoyl group, a benzoyl group), an acyloxy group (e.g., an acetoxy group, a propanoyloxy group, a benzoyloxy group), an alkoxycarbonyl group (e.g., a methoxycarbonyl group, an ethoxycarbonyl group, a propoxycarbonyl group), a cyano group, and a nitro group are exemplified.

Here, as the alkyl, cycloalkyl and aryl groups, those described above are exemplified, but the alkyl group may further be substituted with a fluorine atom or a cycloalkyl group.

As the groups capable of decomposing by the action of an acid to increase the solubility in an alkali developing solution contained in the fluorine-based acid-decomposable resins, e.g., —O—C($R_{36}$)($R_{37}$)($R_{38}$), —O—C($R_{36}$)($R_{37}$)(O$R_{39}$), —O—COO—C($R_{36}$)($R_{37}$)($R_{38}$), —O—C($R_{01}$)($R_{02}$)COO—C($R_{36}$)($R_{37}$)($R_{38}$), —COO—C($R_{36}$)($R_{37}$)($R_{38}$), and —COO—C($R_{36}$)($R_{37}$)(O$R_{39}$) are exemplified.

$R_{36}$, $R_{37}$, $R_{38}$ and $R_{39}$ each represents an alkyl group, a cycloalkyl group, an aryl group, an aralkyl group, or an alkenyl group; $R_{01}$ and $R_{02}$ each represents a hydrogen atom, an alkyl group, a cycloalkyl group, an alkenyl group (e.g., a vinyl group, an allyl group, a butenyl group, a cyclohexenyl group), an aralkyl group (e.g., a benzyl group, a phenethyl group, a naphthylmethyl group), or an aryl group.

The preferred specific examples of the groups include ether groups or ester groups of tertiary alkyl groups such as a t-butyl group, a t-amyl group, a 1-alkyl-1-cyclohexyl group, a 2-alkyl-2-adamantyl group, a 2-adamantyl-2-propyl group, and a 2-(4-methylcyclohexyl)-2-propyl group; acetal groups or acetal ester groups such as a 1-alkoxy-1-ethoxy group and a tetrahydropyranyl group; a t-alkylcarbonate group and a t-alkylcarbonylmethoxy group.

The specific examples of the repeating structural units represented by formulae (FA) to (FG) are shown below, but the invention is not restricted thereto.

(F-1)

(F-2)

(F-3)

(F-4)

(F-5)

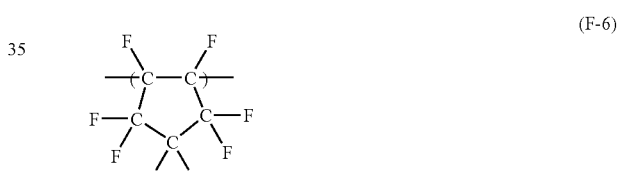
(F-6)

(F-7)

(F-8)

(F-9)

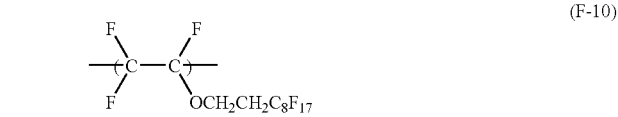
(F-10)

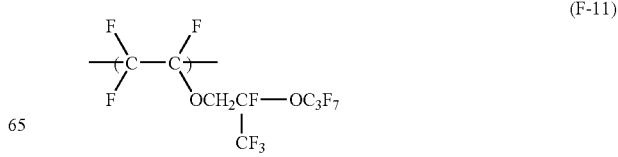
(F-11)

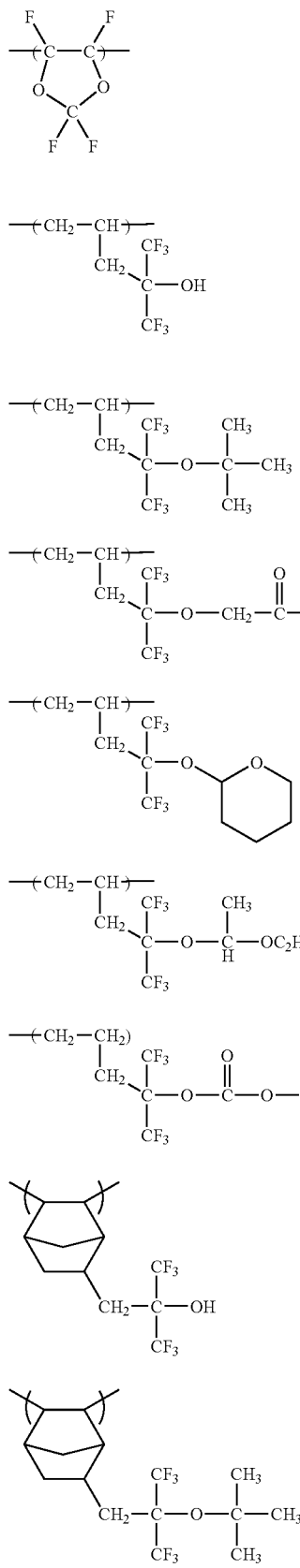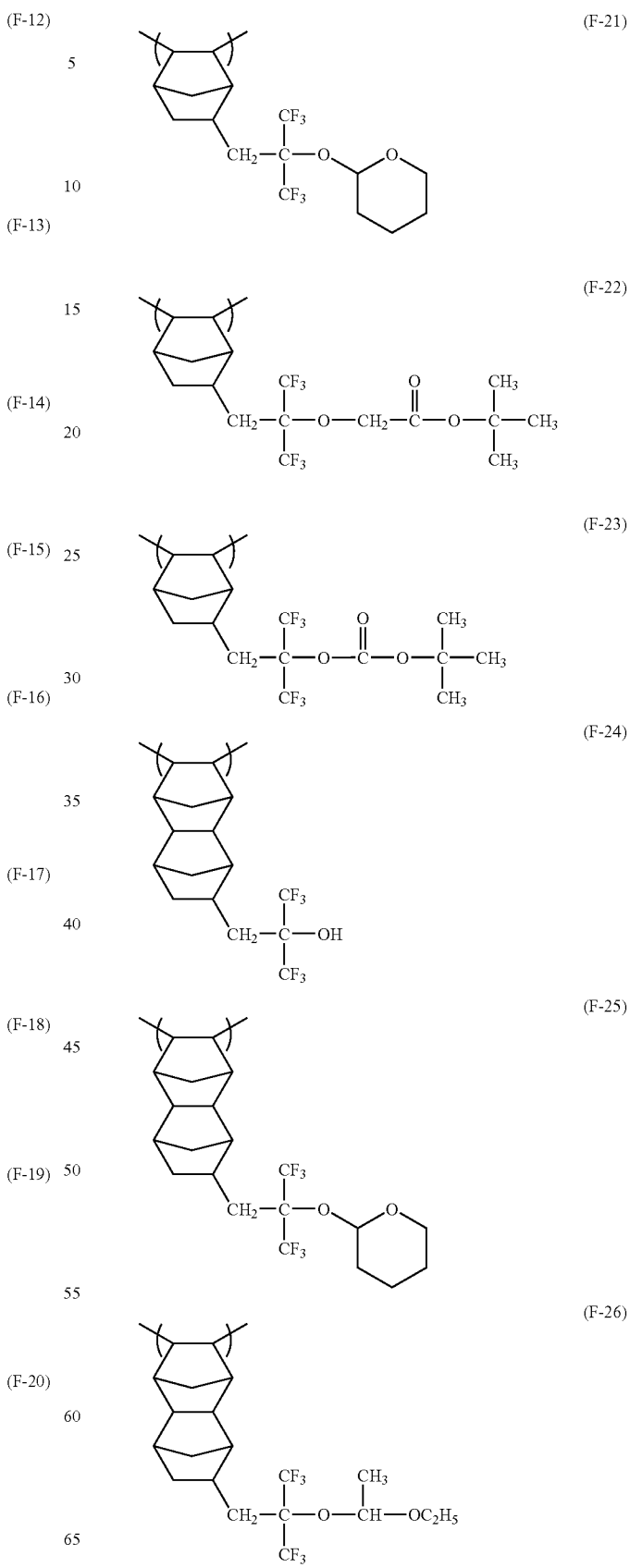

-continued
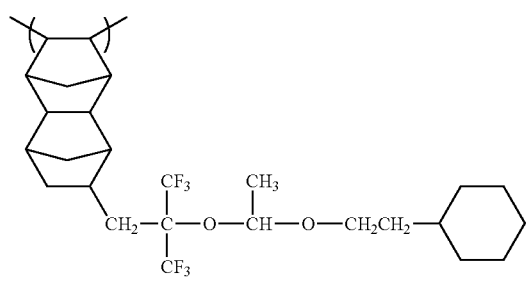
(F-27)
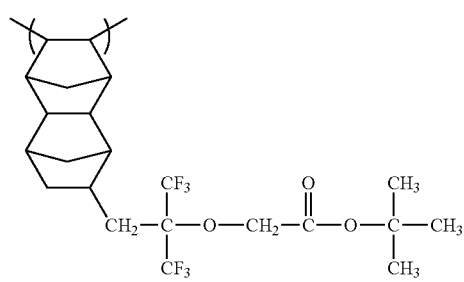
(F-28)
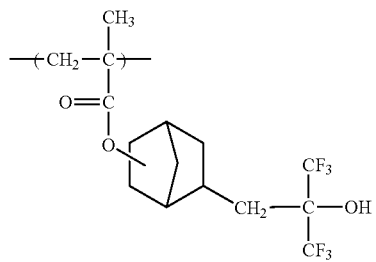
(F-29)
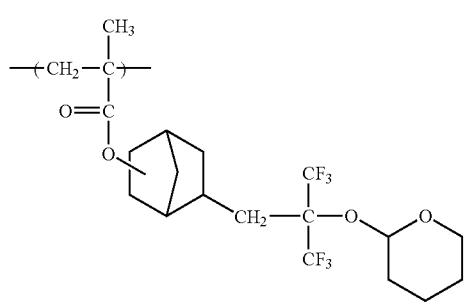
(F-30)
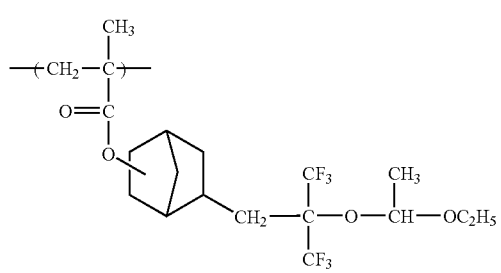
(F-31)
-continued
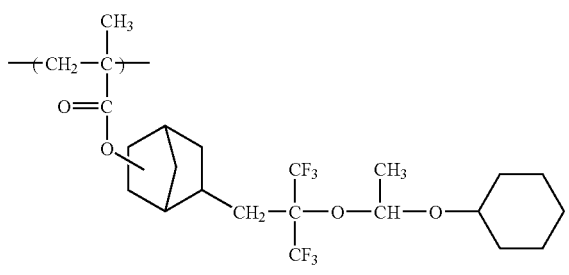
(F-32)
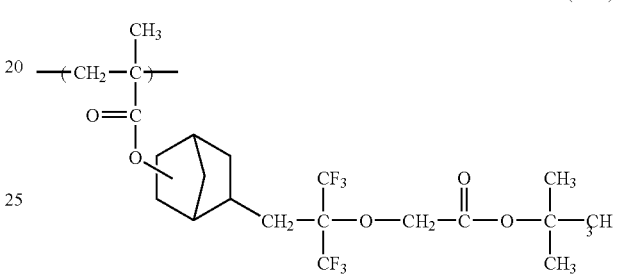
(F-33)
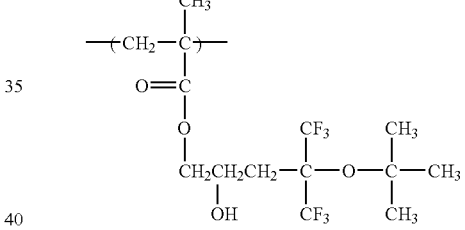
(F-34)
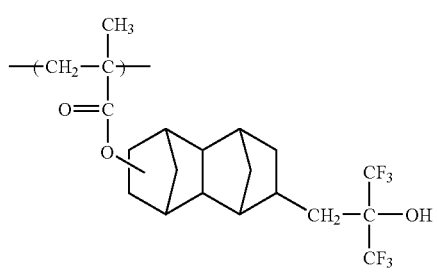
(F-35)
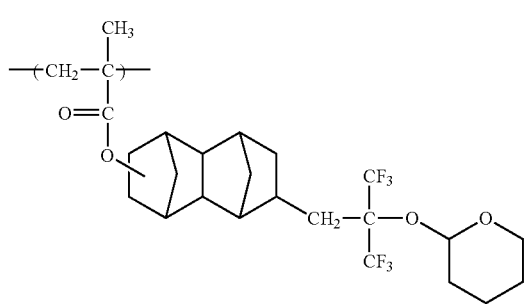
(F-36)

-continued
(F-37)
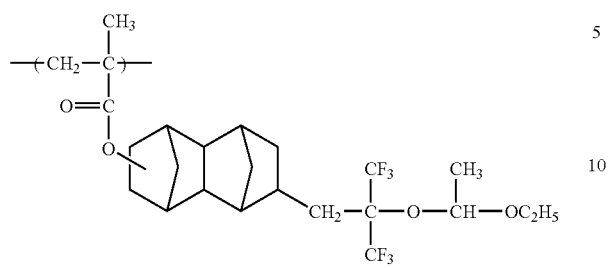
(F-38)
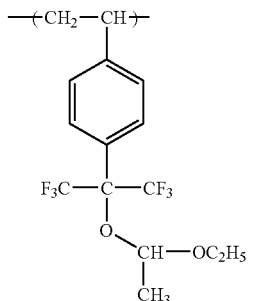
(F-39)
(F-40)
(F-41)
-continued
(F-42)
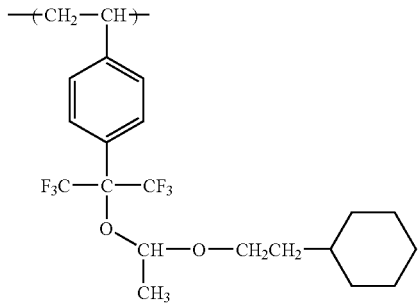
(F-43)
(F-44)
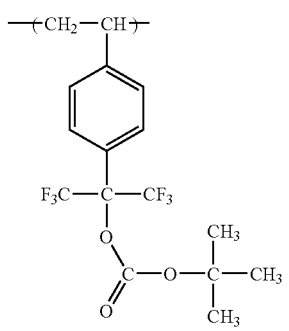
(F-45)
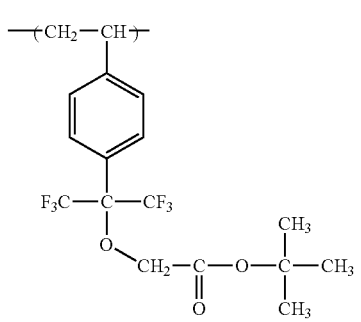
(F-46)
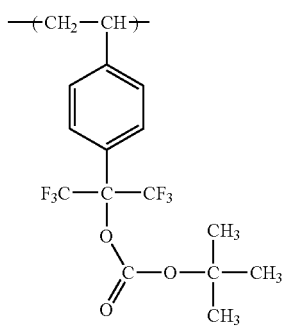

-continued
(F-47) 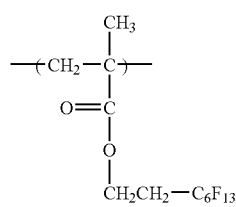
(F-48) 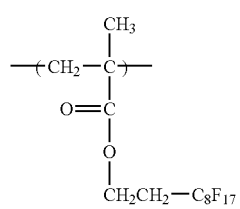
(F-49) 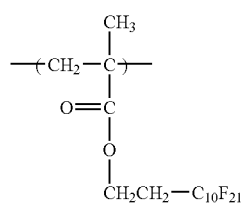
(F-50) 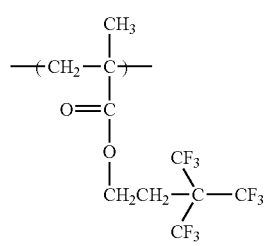
(F-51) 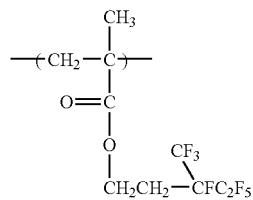
(F-52) 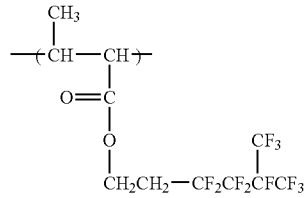
(F-53) 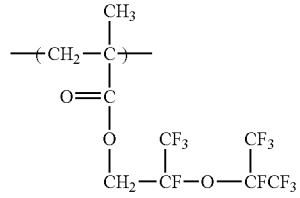
-continued
(F-54) 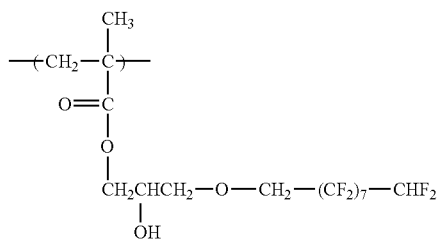
(F-55) 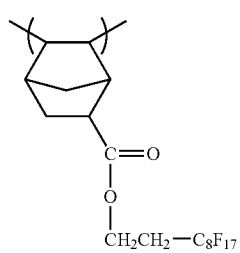
(F-56) 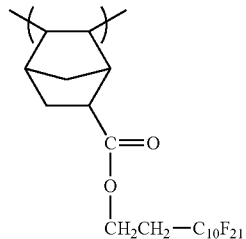
(F-57) 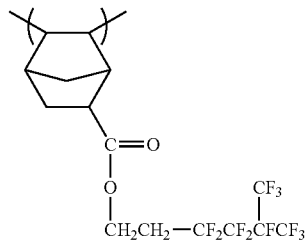
(F-58) 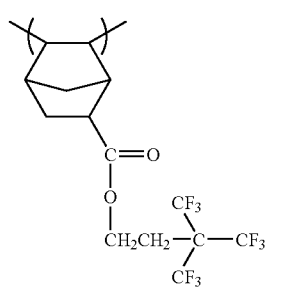
(F-59) 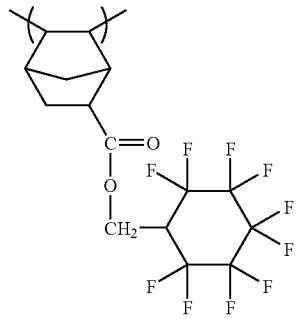

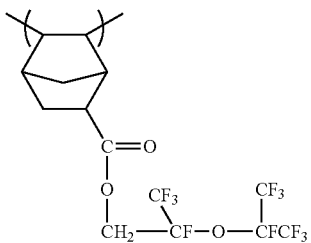
(F-60)

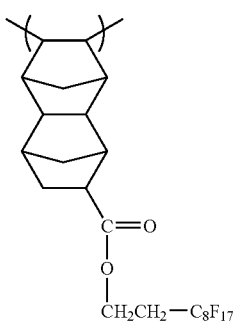
(F-61)

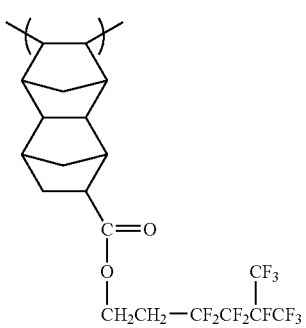
(F-62)

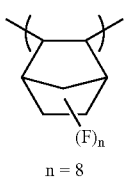
n = 8
(F-63)

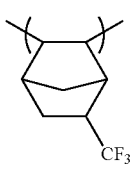
(F-64)

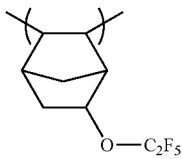
(F-65)

The total content of the repeating units represented by formulae (FA) to (FG) is preferably from 10 to 80 mol % to all the repeating units constituting the resin, more preferably from 30 to 70 mol %, and still more preferably from 35 to 65 mol %.

For the purpose of further improving the performances of the resist of the invention, the fluorine-based acid-decomposable resins may further be copolymerized with other polymerizable monomers in addition to the above repeating structural units.

As the copolymerizable monomers that can be used, compounds having one addition polymerizable unsaturated bond selected from acrylic esters, acrylamides, methacrylic esters, methacrylamides, allyl compounds, vinyl ethers, vinyl esters, styrens, and crotonic esters other than those described above are exemplified.

From the points of improving dry etching resistance, adjusting alkali solubility, and improving adhesion with substrates, it is preferred that these fluorine-based acid-decomposable resins contain other repeating units as the copolymerization components besides the above repeating units having fluorine atoms. Preferred other repeating units are as follows.

1) The repeating units having an alicyclic hydrocarbon structure represented by any of formulae (pI) to (pVI) and formula (II-AB). Specifically the above exemplified repeating units 1 to 23 and repeating units [II-1] to [II-32] shown above. Of the repeating units 1 to 23, those in which Rx represents CF$_3$ are referred.

2) The repeating units having the lactone structure represented by formula (Lc) and any of formulae (V-1) to (V-5). Specifically the above-exemplified repeating units, in particular, the above-exemplified repeating units represented by formula (Lc) and any of formulae (V-1) to (V-4).

3) The repeating units derived from vinyl compounds having maleic anhydride, vinyl ether or a cyano group represented by the following formula (XV), (XVI) or (XVII). Specifically repeating units (C-1) to (C-15) shown below are exemplified. These other repeating units may or may not contain a fluorine atom.

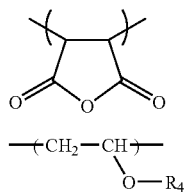
(XV)

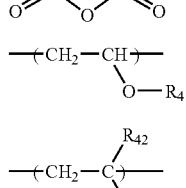
(XVI)

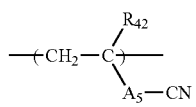
(XVII)

In the above formulae, $R_{41}$ represents an alkyl group, a cycloalkyl group, an aralkyl group, or an aryl group, and the alkyl group represented by $R_{41}$ may be substituted with an aryl group.

$R_{42}$ represents a hydrogen atom, a halogen atom, a cyano group, or an alkyl group.

$A_5$ represents a single bond, a divalent alkylene group, alkenylene group, cycloalkylene group, or arylene group, or —O—CO—$R_{22}$—, —CO—O—$R_{23}$—, or —CO—N($R_{24}$)—$R_{25}$—.

$R_{22}$, $R_{23}$ and $R_{25}$, which may be the same or different, each represents a single bond, or a divalent alkylene group, alkenylene group, cycloalkylene group or arylene group which may have an ether group, an ester group, an amido group, a urethane group or a ureido group.

$R_{24}$ represents a hydrogen atom, an alkyl group, a cycloalkyl group, an aralkyl group, or an aryl group.

Here, as the examples of the substituents, the same groups as the substituents in formulae (FA) to (FG) can be exemplified.

The specific examples of the repeating structural units represented by formula (XV), (XVI) or (XVII) are shown below, but the invention is not restricted thereto.

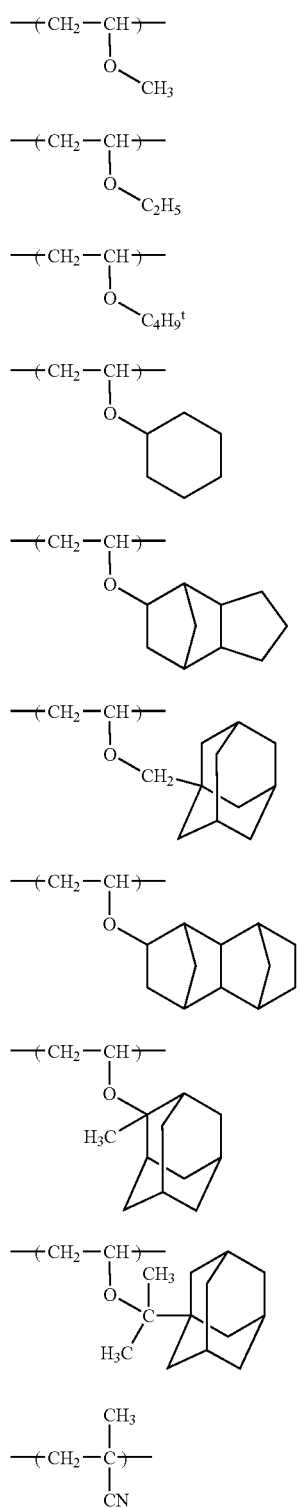

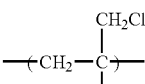

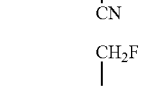

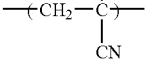

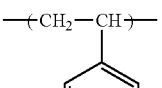

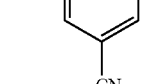

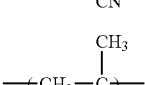

The total amount of the repeating units represented by formula (XV), (XVI) or (XVII) and other repeating units is preferably from 0 to 70 mol % to all the repeating units constituting the resin, more preferably from 10 to 60 mol %, and still more preferably from 20 to 50 mol %.

The fluorine-based acid-decomposable resins may contain an acid-decomposable group in any repeating unit.

The content of a repeating unit having an acid decomposable group is preferably from 10 to 70 mol % to all the repeating units, more preferably from 20 to 60 mol %, and still more preferably from 30 to 60 mol %.

The fluorine-based acid-decomposable resins can be synthesized by radical polymerization in almost the similar same manner to the synthesis of alicyclic hydrocarbon-based acid-decomposable resins.

The weight average molecular weight of the resin of component (C) is preferably from 2,000 to 200,000 as the polystyrene equivalent value by the GPC method. By making the weight average molecular weight 2,000 or more, heat resistance and dry etching resistance can be improved, and by making the weight average molecular weight 200,000 or less, developing property can be improved, and film-forming property can be heightened, since the viscosity becomes low. The weight average molecular weight is more preferably from 5,000 to 50,000, and still more preferably from 7,000 to 30,000. By the adjustment of the molecular weight, it is possible to reconcile the heat resistance, resolution, development failure and the like of the composition. The degree of dispersion (Mw/Mn) of the resin of component (C) is preferably from 1.0 to 3.0, more preferably from 1.2 to 2.5, and still more preferably from 1.2 to 1.6. By the adjustment of the degree of dispersion to a proper range, the performance of line edge roughness can be increased.

In the positive photosensitive composition in the invention, the proportion of the resin of component (C) in accordance with the invention in the composition as a whole is preferably from 40 to 99.9 mass % in all the solids content, more preferably from 50 to 99 mass %, and still more preferably from 80 to 96 mass %.

Resin (D) Soluble in an Alkali Developing Solution:

The photosensitive composition in the invention can contain resin (D) soluble in an alkali developing solution (hereinafter also referred to as "component (D)" or "alkali-soluble resin").

The alkali dissolution rate of alkali-soluble resins is preferably 20 Å/sec or more when measured with 0.261 N tetramethylammonium hydroxide (TMAH) at 23° C., and especially preferably 200 Å/sec or more.

As alkali-soluble resins for use in the invention, e.g., novolak resins, hydrogenated novolak resins, acetone-pyrogallol resins, o-polyhydroxystyrene, m-polyhydroxy-styrene, p-polyhydroxystyrene, hydrogenated polyhydroxy-styrene, halogen- or alkyl-substituted polyhydroxystyrene, hydroxystyrene-N-substituted maleimide copolymers, o/p- and m/p-hydroxystyrene copolymers, partially O-alkylated products of the hydroxyl group of polyhydroxystyrene (e.g., from 5 to 30 mol % O-methylated, O-(1-methoxy)ethylated, O-(1-ethoxy)ethylated, O-2-tetrahydropyranylated, and O-(t-butoxycarbonyl)methylated products), and partially O-acylated products (e.g., from 5 to 30 mol % o-acetylated, and O-(t-butoxy)carbonylated products), styrene-maleic anhydride copolymers, styrene-hydroxystyrene copolymers, α-methylstyrene-hydroxystyrene copolymers, carboxyl group-containing methacrylic resins and derivatives thereof, and polyvinyl alcohol derivatives can be exemplified, but the invention is not limited to these resins.

Particularly preferred alkali-soluble resins are novolak resins, o-polyhydroxystyrene, m-polyhydroxystyrene p-polyhydroxystyrene, copolymers of them, alkyl-substituted polyhydroxystyrene, partially O-alkylated or O-acylated products of polyhydroxystyrene, styrene-hydroxystyrene copolymers, and α-methylstyrene-hydroxystyrene copolymers.

The novolak resins can be obtained by addition condensation to aldehydes with prescribed monomers as main components in the presence of an acid catalyst.

The weight average molecular weight of alkali-soluble resins is 2,000 or more, preferably from 5,000 to 200,000, and more preferably from 5,000 to 100,000.

Here, the weight average molecular weight is defined as the polystyrene equivalent value by gel permeation chromatography.

These alkali-soluble resins (D) in the invention may be used in combination of two kinds or more.

The use amount of alkali-soluble resins is from 40 to 97 mass % based on the solids content of the photosensitive composition at large, and preferably from 60 to 90 mass %.

Dissolution-Inhibiting Compound Capable of Decomposing by the Action of an Acid to Increase Solubility in an Alkali Developing Solution Having a Molecular Weight of 3,000 or Less:

The compound is hereinafter also referred to as merely "dissolution-inhibiting compound".

As the dissolution-inhibiting compound capable of decomposing by the action of an acid to thereby increase the solubility in an alkali developing solution having a molecular weight of 3,000 or less, alicyclic or aliphatic compounds containing an acid-decomposable group, such as cholic acid derivatives containing an acid-decomposable group as described in *Proceeding of SPIE*, 2724, 355 (1996) are preferred so as not to reduce the transmission of lights of 220 nm or less. As the acid-decomposable groups and alicyclic structures, the same as those described above in the alicyclic hydrocarbon-based acid-decomposable resin are exemplified.

When the photosensitive composition of the invention is subjected to exposure with a KrF excimer laser or irradiated with electron beams, it is preferred for the photosensitive composition to contain a phenolic compound having a structure obtained by substituting the phenolic hydroxyl group of the phenolic compound with an acid-decomposable group. As the phenolic compounds, compounds having from 1 to 9 phenolic skeletons are preferred, and compounds having from 2 to 6 phenolic skeletons are more preferred.

The molecular weight of the dissolution-inhibiting compound in the invention is 3,000 or less, preferably from 300 to 3,000, and more preferably from 500 to 2,500.

The addition amount of the dissolution-inhibiting compound is preferably from 3 to 50 mass % based on the solids content of the photosensitive composition, and more preferably from 5 to 40 mass %.

The specific examples of the dissolution-inhibiting compounds are shown below, but the invention is not restricted to these compounds.

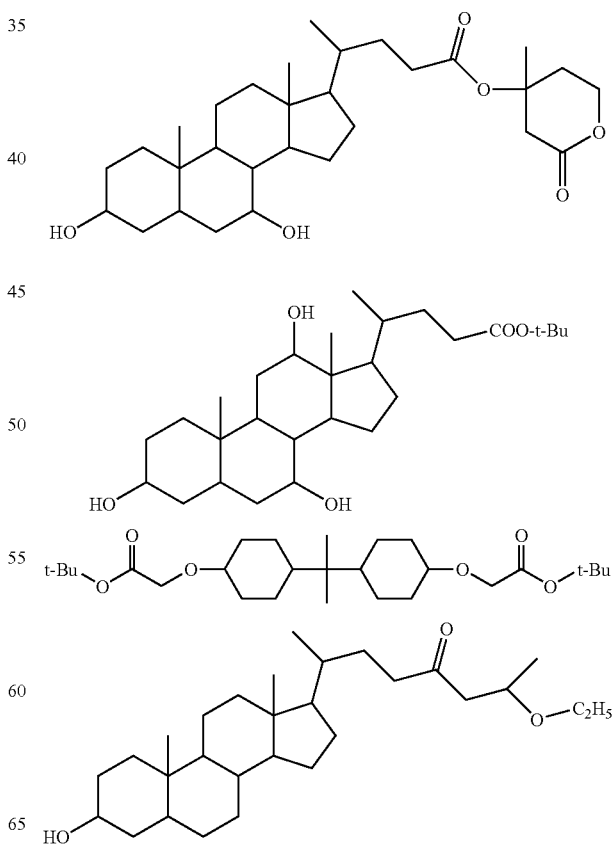

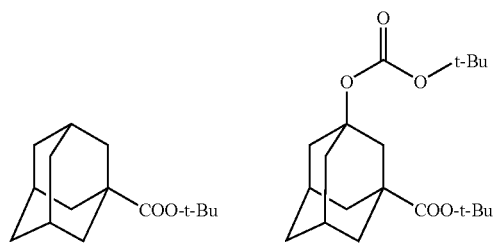
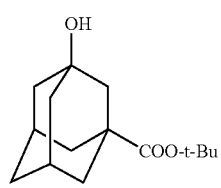

Acid Crosslinking Agent (E) Capable of Crosslinking with the Alkali-Soluble Resin by the Action of an Acid:

Hereinafter also referred to as "component (E)" or "a crosslinking agent".

A crosslinking agent is used in the negative photosensitive composition of the invention.

Every compound capable of crosslinking the resins soluble in an alkali developing solution by the action of an acid can be used as crosslinking agents, but the following (1) to (3) are preferably used.

(1) A hydroxymethyl material, an alkoxymethyl material and an acyloxymethyl material of phenol derivatives, (2) Compounds having an N-hydroxymethyl group, an N-alkoxy-methyl group, or an N-acyloxymethyl group, and (3) Compounds having an epoxy group.

The alkoxymethyl group preferably has 6 or less carbon atoms, and the acyloxymethyl group preferably has 6 or less carbon atoms.

Of these crosslinking agents, particularly preferred compounds are shown below.

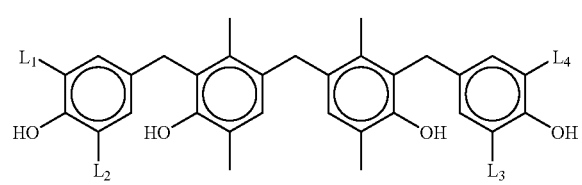
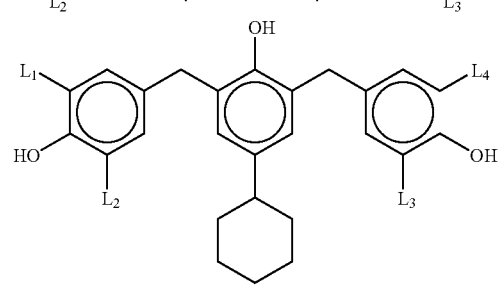
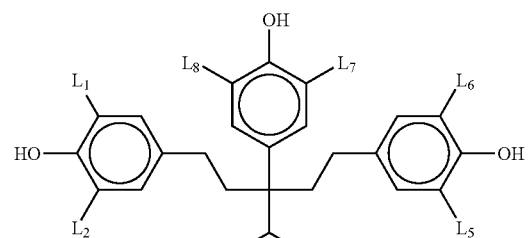
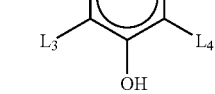
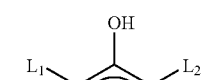
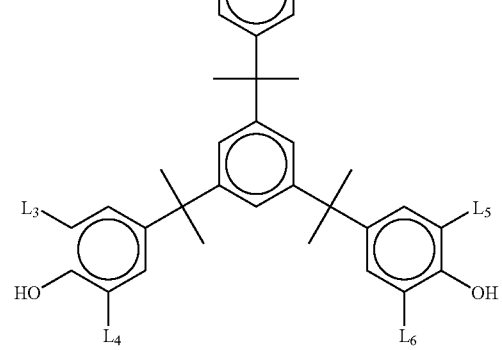
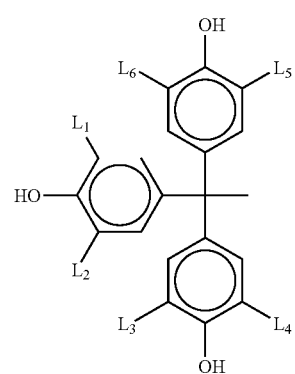
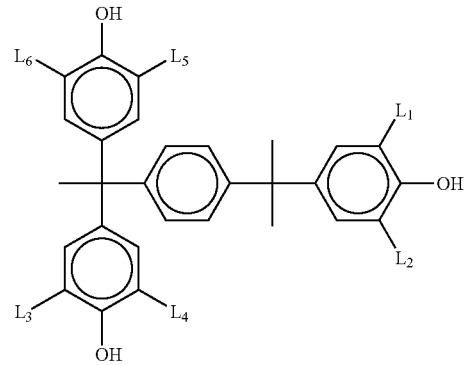

-continued

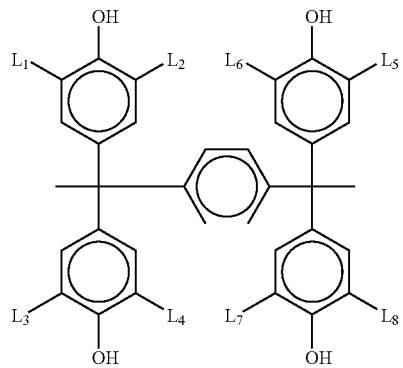

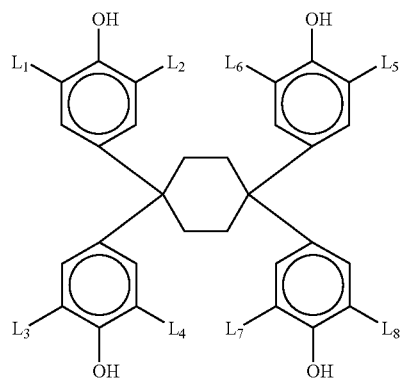

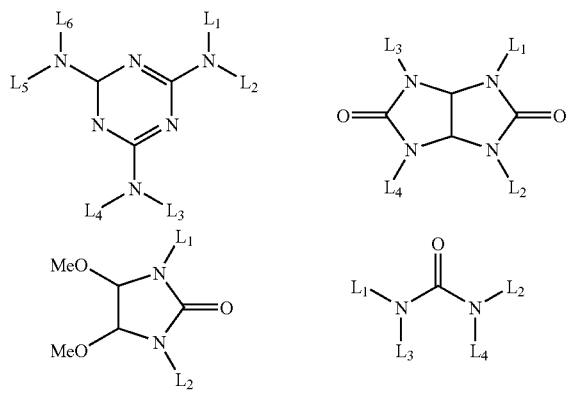

In the above formulae, $L_1$ to $L_8$, which may be the same or different, each represents a hydrogen atom, a hydroxymethyl group, a methoxymethyl group, an ethoxymethyl group, or an alkyl group having from 1 to 6 carbon atoms.

Crosslinking agents are used generally in proportion of from 3 to 70 mass % in the solids content of the photosensitive composition, and preferably from 5 to 50 mass %.

Basic Compound (F):

For decreasing the fluctuation of performances due to aging during the period of time from exposure to heating, it is preferred for the photosensitive composition of the invention to contain a basic compound.

As the preferred structures of basic compounds, the structures represented by any of the following formulae (A) to (E) can be exemplified.

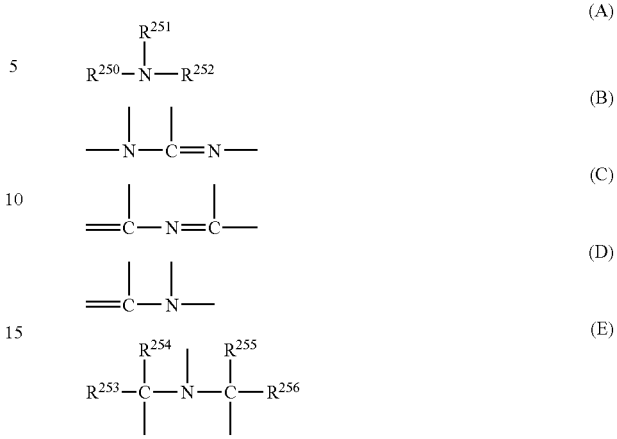

In formula (A), $R^{250}$, $R^{251}$ and $R^{252}$ each represents a hydrogen atom, an alkyl group having from 1 to 20 carbon atoms, a cycloalkyl group having from 3 to 20 carbon atoms, or an aryl group having from 6 to 20 carbon atoms, and $R^{250}$ and $R^{251}$ may be bonded to each other to form a ring. These groups may have a substituent, and as the alkyl group and cycloalkyl group having a substituent, an aminoalkyl group having from 1 to 20 carbon atoms or an aminocycloalkyl group having from 3 to 20 carbon atoms, a hydroxyalkyl group having from 1 to 20 carbon atoms or a hydroxycycloalkyl group having from 3 to 20 carbon atoms are preferred.

These groups may contain an oxygen atom, a sulfur atom or a nitrogen atom in the alkyl chain.

In formula (E), $R^{253}$, $R^{254}$, $R^{255}$ and $R^{256}$ each represents an alkyl group having from 1 to 6 carbon atoms, or a cycloalkyl group having from 3 to 6 carbon atoms.

As the preferred examples of basic compounds, guanidine, aminopyrrolidine, pyrazole, pyrazoline, piperazine, aminomorpholine, aminoalkylmorpholine, and piperidine can be exemplified, and these compounds may have a substituent. As more preferred basic compounds, compounds having an imidazole structure, a diazabicyclo structure, an onium hydroxide structure, an onium carboxylate structure, a trialkylamine structure, an aniline structure, or a pyridine structure, alkylamine derivatives having a hydroxyl group and/or an ether bond; and aniline derivatives having a hydroxyl group and/or an ether bond can be exemplified.

As the compounds having an imidazole structure, imidazole, 2,4,5-triphenylimidazole, and benzimidazole can be exemplified. As the compounds having a diazabicyclo structure, 1,4-diazabicyclo[2.2.2]octane, 1,5-diazabicyclo[4.3.0]nona-5-ene, and 1,8-diazabicyclo[5.4.0]undeca-7-ene can be exemplified. As the compounds having an onium hydroxide structure, triarylsulfonium hydroxide, phenacylsulfonium hydroxide, sulfonium hydroxide having a 2-oxoalkyl group, specifically triphenylsulfonium hydroxide, tris(t-butyl-phenyl)sulfonium hydroxide, bis(t-butylphenyl)iodonium hydroxide, phenacylthiophenium hydroxide, and 2-oxopropyl-thiophenium hydroxide can be exemplified. The compounds having an onium carboxylate structure are compounds having an onium hydroxide structure in which the anionic part is carboxylated, e.g., acetate, adamantane-1-carboxylate, and perfluoroalkyl carboxylate are exemplified. As the compounds having a trialkylamine structure, tri(n-butyl)amine and tri(n-octyl)amine can be exemplified. As the aniline compounds, 2,6-diisopropylaniline and N,N-dimethylaniline can be exemplified. As the alkylamine derivatives having a hydroxyl group and/or an ether bond, ethanolamine, diethanol-amine, triethanolamine, and tris(methoxyethoxyethyl)amine can be exemplified. As the aniline derivatives having a hydroxyl group and/or an ether bond, N,N-bis(hydroxyethyl)-aniline can be exemplified.

These basic compounds are used alone or in combination of two or more. However, when the use amount of component (A) is 0.05 mass % or more, a basic compound may not be used. When a basic compound is used, the use amount is generally from 0.001 to 10 mass % based on the solids content of the photosensitive composition, and preferably from 0.01 to 5 mass %. For securing a sufficient addition effect, the addition amount is preferably 0.001 mass % or more, and in view of sensitivity and the developing property of a non-exposed area, the addition amount is preferably 10 mass % or less.

Fluorine and/or Silicon Surfactant (G):

It is preferred for the photosensitive composition in the invention to further contain a surfactant, either one, or two or more, of fluorine and/or silicon surfactants (a fluorine surfactant, a silicon surfactant, a surfactant containing both a fluorine atom and a silicon atom).

By containing a surfactant, it becomes possible for the photosensitive composition in the invention to provide a resist pattern excellent in sensitivity and resolution, and low in defects in adhesion and development in using an exposure light source of 250 nm or lower, in particular, 220 nm or lower.

These fluorine and/or silicon surfactants are disclosed, e.g., in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862, U.S. Pat. Nos. 5,405,720, 5,360,692, 5,529,881, 5,296,330, 5,436,098, 5,576,143, 5,294,511 and 5,824,451. The commercially available surfactants shown below can also be used as they are.

As the commercially available fluorine or silicon surfactants usable in the invention, e.g., Eftop EF301 and EF303 (manufactured by Shin-Akita Kasei Co., Ltd.), Fluorad FC 430 and 431 (manufactured by Sumitomo 3M Limited), Megafac F171, F173, F176, F189, and $R^{08}$ (manufactured by Dainippon Ink and Chemicals Inc.), Sarfron S-382, SC 101, 102, 103, 104, 105 and 106 (manufactured by ASAHI GLASS CO., LTD.), Troy Sol S-366 (manufactured by Troy Chemical Co., Ltd.) are exemplified. In addition, polysiloxane polymer KP-341 (manufactured by Shin-Etsu Chemical Co., Ltd.) can also be used as a silicon surfactant.

In addition to these known surfactants as exemplified above, a surfactant using a polymer having a fluoro-aliphatic group derived from a fluoro-aliphatic compound manufactured by a telomerization method (also called a telomer method) or an oligomerization method (also called an oligomer method) can be used. The fluoro-aliphatic compound can be synthesized by the method disclosed in JP-A-2002-90991.

As the polymers having a fluoro-aliphatic group, copolymers of monomers having a fluoro-aliphatic group and (poly(oxyalkylene))acrylate and/or (poly(oxyalkylene))methacrylate are preferred, and they may be irregularly distributed or block copolymerized. As the poly(oxyalkylene) groups, a poly(oxyethylene) group, a poly(oxypropylene) group, a poly(oxybutylene) group and the like are exemplified. Further, the polymers may be units having alkylenes different in chain length in the same chain length, such as a block combination of poly(oxyethylene and oxypropylene and oxyethylene), and a block combination of poly(oxyethylene and oxypropylene). In addition, a copolymer of a monomer having a fluoro-aliphatic group and poly(oxyalkylene)acrylate (or methacrylate) may be not only a bipolymer but also a terpolymer or higher polymers obtained by copolymerization of a monomer having different two or more kinds of fluoro-aliphatic groups and different two or more kinds of poly(oxyalkylene) acrylates (or methacrylates) at the same time.

For example, as commercially available surfactants, Megafac F178, F-470, F-473, F-475, F-476 and F-472 (manufactured by Dainippon Ink and Chemicals Inc.) can be exemplified. Further, a copolymer of acrylate (or methacrylate) having a $C_6F_{13}$ group and (poly(oxyalkylene)) acrylate (or methacrylate), a copolymer of acrylate (or methacrylate) having a $C_6F_{13}$ group, (poly(oxyethylene)) acrylate (or methacrylate), and (poly-(oxypropylene)) acrylate (or methacrylate), a copolymer of acrylate (or methacrylate) having a $C_8F_{17}$ group and (poly-(oxyalkylene)) acrylate (or methacrylate), and a copolymer of acrylate (or methacrylate) having a $C_8F_{17}$ group, (poly(oxy-ethylene)) acrylate (or methacrylate), and poly(oxypropylene)acrylate (or methacrylate) are exemplified.

The use amount of fluorine and/or silicon surfactant is preferably from 0.0001 to 2 mass % to all the amount of the photosensitive composition (excluding solvents), and more preferably from 0.001 to 1 mass %.

Solvent (H):

The above components of the photosensitive composition of the invention are dissolved in a prescribed organic solvent and used.

As the organic solvents usable in the invention, for example, ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, and tetrahydrofuran are exemplified.

Solvents containing at least propylene glycol monoalkyl ether carboxylate are preferably used in the invention.

As the propylene glycol monoalkyl ether carboxylate, e.g., propylene glycol monomethyl ether acetate, propylene glycol monomethyl ether propionate, propylene glycol monoethyl ether acetate and the like can be exemplified.

It is preferred that propylene glycol monoalkyl ether carboxylate solvent is used alone, or as mixed solvents with other solvents. As the solvents to be mixed (solvents used in combination), propylene glycol monoalkyl ether, alkyl lactate, alkyl alkoxypropionate, lactone compounds, cyclic ketones and the like can be exemplified.

As the propylene glycol monoalkyl ether, e.g., propylene glycol monomethyl ether, propylene glycol monoethyl ether, etc., can be exemplified.

As the alkyl lactate, e.g., methyl lactate, ethyl lactate, etc., can be exemplified.

As the alkyl alkoxypropionate, e.g., methyl methoxy-propionate, ethyl methoxypropionate, methyl ethoxypropionate, ethyl ethoxypropionate, etc., can be exemplified.

As the lactone compounds, e.g., γ-butyrolactone, etc., can be exemplified.

As the cyclic ketone solvents, e.g., cyclopentanone, 3-methyl-2-cyclopentanone, cyclohexanone, 2-methylcyclo-hexanone, 2,6-dimethylcyclohexanone, cycloheptanone, cyclooctanone, isophorone, etc., can be exemplified, and cyclohexanone and cycloheptanone are preferred.

As an especially preferred solvent to be used in combination, propylene glycol monoalkyl ether can be exemplified.

By using propylene glycol monoalkyl ether as the solvent used in combination, substrate adhesion, developing property DOF and the like are improved.

The ratio of the propylene glycol monoalkyl ether carboxylate and the above solvents used in combination (in mass ratio) is preferably from 10/90 to 95/5, more preferably from 20/80 to 80/20, and still more preferably from 30/70 to 70/30.

From the viewpoint of heightening uniform film thickness and resistance to development failure, high boiling point solvents having a boiling point of 200° C. or higher, e.g., ethylene carbonate, propylene carbonate, etc., may be mixed.

The addition amount of these high boiling point solvents is generally from 0.1 to 15 mass % in all the solvents, preferably from 0.5 to 10 mass %, and more preferably from 1 to 5 mass %.

In the invention, a photosensitive composition having solids content concentration of generally from 3 to 25 mass %, preferably from 5 to 22 mass %, and more preferably from 5 to 15 mass % is prepared with a single solvent, preferably two or more solvents.

Other Additives (I):

If necessary, dyes, plasticizers, surfactants other than the above component (G), photosensitizers, and compounds for expediting the dissolution of composition in a developing solution may further be added to the photosensitive composition in the present invention.

The compounds for expediting dissolution in a developing solution that can be used in the invention are low molecular weight compounds having two or more phenolic OH groups, or one or more carboxyl groups, and a molecular weight of 1,000 or less. When a carboxyl group is contained, alicyclic or aliphatic compounds are preferred.

The preferred addition amount of these dissolution accelerating compounds is preferably from 2 to 50 mass % based on the resin of component (C) or the resin of component (D), and more preferably from 5 to 30 mass %. The amount is preferably 50 mass % or less in the point of restraint of development residue and prevention of pattern deformation in development.

These phenolic compounds having a molecular weight of 1,000 or less can be easily synthesized with referring to the methods disclosed, e.g., in JP-A-4-122938, JP-A-2-28531, U.S. Pat. No. 4,916,210, and EP 219294.

As the specific examples of the alicyclic or aliphatic compounds having a carboxyl group, carboxylic acid derivatives having a steroid structure, e.g., cholic acid, deoxycholic acid, and lithocholic acid, adamantanecarboxylic acid derivatives, adamantanedicarboxylic acid, cyclohexanecarboxylic acid, and cyclohexanedicarboxylic acid are exemplified, but the invention is not restricted to these compounds.

In the invention, surfactants other than fluorine and/or silicon surfactants (G) can also be used. Specifically, nonionic surfactants, such as polyoxyethylene alkyl ethers, polyoxyethylene alkyl allyl ether, polyoxyethylene-polyoxypropylene block copolymers, sorbitan fatty acid esters, and polyoxyethylene sorbitan fatty acid esters can be exemplified.

These surfactants may be used alone, or some surfactants can be used in combination.

Pattern Forming Method (J):

The photosensitive composition in the invention is used by dissolving the above components in a prescribed organic solvent, preferably a mixed solvent as described above, and coating the resulting solution on a prescribed support as described below.

For example, the photosensitive composition is coated on a substrate such as the one used in the manufacture of precision integrated circuit element (e.g., silicon/silicon dioxide coating) by an appropriate coating method with a spinner or a coater, and dried, to thereby form a photosensitive film. Incidentally, it is also possible to coat a known antireflection film.

The photosensitive film is irradiated with an actinic ray or radiation through a prescribed mask, preferably subjected to baking (heating), and then development. Thus, a good pattern can be obtained.

At the time of irradiation with an actinic ray or radiation, exposure (immersion exposure) may be performed by filling a liquid having higher refractive index than that of air between a photosensitive film and a lens, by which resolution can be raised.

As actinic rays or radiation, infrared rays, visible rays, ultraviolet rays, far ultraviolet rays, X-rays and electron beams can be exemplified, and preferably far ultraviolet rays of the wavelengths of 250 nm or less, and more preferably 220 nm or less. Specifically, a KrF excimer laser (248 nm), an ArF excimer laser (193 nm), an $F_2$ excimer laser (157 nm), X-rays and electron beams are exemplified, and an ArF excimer laser, an $F_2$ excimer laser, EUV (13 nm), and electron beams are preferred.

Immersion Exposure:

When the photosensitive composition in the invention is subjected to immersion exposure, it is preferred that the photosensitive composition is used in a thickness of from 30 to 250 nm in view of the improvement of resolution, and more preferably a thickness of from 30 to 100 nm. Such a desired thickness can be realized by setting the concentration of solids content in the photosensitive composition in a proper range and giving appropriate viscosity to thereby improve the coating property and film forming property.

The concentration of all the solids content in the photosensitive composition is preferably from 1 to 10 mass %, more preferably from 1 to 8 mass %, and still more preferably from 1.0 to 6.0 mass %.

When the photosensitive composition in the invention is subjected to immersion exposure, the photosensitive composition is used by dissolving the above components in a prescribed organic solvent, preferably in a mixed solvent as described above, and coating the resulting solution on a prescribed support as follows.

That is, the photosensitive composition is coated on a substrate such as the one used in the manufacture of precision integrated circuit elements (e.g., silicon/silicon dioxide coating) by an appropriate coating method with a spinner or a coater in an arbitrary thickness (generally from 30 to 500 nm). After coating, if necessary, a resist film is washed with the immersion liquid. The washing time is generally from 5 seconds to 5 minutes.

Subsequently, the coated photosensitive composition is dried by spin or bake to form a photosensitive film (hereinafter also referred to as a resist film), and the resulting resist film is subjected to exposure for pattern formation through a mask via an immersion liquid (immersion exposure). For example, exposure is performed in a state of filling an immersion liquid between the resist film and an optical lens. The exposure dose can be optionally set, but is generally from 1 to 100 mJ/cm². After exposure, if necessary, the resist film is washed with the immersion liquid. The washing time is generally from 5 seconds to 5 minutes. Subsequently, the resist film is preferably subjected to spin or/and bake, development and rinsing, whereby a good pattern can be obtained. It is preferred to perform bake, and the temperature of bake is generally from 30 to 300° C. The time from exposure to bake process is preferably shorter from the viewpoint of PED.

The exposure rays here are far ultraviolet rays of the wavelengths of preferably 250 nm or less, and more preferably 220 nm or less. Specifically, a KrF excimer laser (248 nm), an ArF excimer laser (193 nm), an $F_2$ excimer laser (157 nm), and X-rays are exemplified.

Incidentally, the variation of performances at the time when a resist is subjected to immersion exposure is thought to be resulting from the contact of the resist surface with an immersion liquid.

An immersion liquid for use in immersion exposure is described below.

An immersion liquid for use in immersion exposure is preferably a liquid having a temperature coefficient of refractive index as small as possible so as to be transparent to the exposure wavelength and to hold the distortion of an optical image reflected on the resist at the minimum. In particular, when the exposure light source is an ArF excimer laser (wavelength: 193 nm), it is preferred to use water as the immersion liquid for easiness of availability and capable of handling easily, in addition to the above points.

It is also possible to use a medium having a refractive index of 1.5 or more for capable of improving the refractive index. The medium may be an aqueous solution or an organic solvent.

When water is used as the immersion liquid, to reduce the surface tension of water and to increase the surface activity, a trace amount of additive (a liquid) that does not dissolve the resist layer on a wafer and has a negligible influence on the optical coating of the underside of a lens element may be added. As such additives, aliphatic alcohols having a refractive index almost equal to the refractive index of water are preferred, and specifically methyl alcohol, ethyl alcohol and isopropyl alcohol are exemplified. By adding an alcohol having a refractive index almost equal to that of water, even if the alcohol component in water is evaporated and the concentration of the content is changed, the refractive index variation of the liquid as a whole can be made extremely small. On the other hand, when impurities opaque to the light of 193 nm or substances largely different from water in a refractive index are mixed, these substances bring about the distortion of an optical image reflected on the resist. Accordingly the water to be used is preferably distilled water. Further, pure water filtered through an ion exchange filter may be used.

The electric resistance of water is preferably 18.3 MΩ·cm or higher, and TOC (total organic material concentration) is preferably 20 ppb or lower, and it is preferred that water has been subjected to deaeration treatment.

It is also possible to heighten lithographic performance by increasing the refractive index of an immersion liquid. From such a point of view, additives capable of increasing the refractive index may be added to water, or heavy water ($D_2O$) may be used in place of water.

A film hardly soluble in an immersion liquid (hereinafter also referred to as "topcoat") may be provided between a resist film manufactured by the photosensitive composition of the invention and an immersion liquid so as not to bring the resist film into direct contact with the immersion liquid. The necessary functions required of the topcoat are the aptitude for coating on the upper layer of a resist, the transparency to radiation, in particular the transparency to the ray of 193 nm, and the insolubility in an immersion liquid. It is preferred that the topcoat is not mixed with a resist and can be coated uniformly on a resist upper layer.

From the viewpoint of the transparency to 193 nm, a polymer not containing an aromatic group is preferred as the topcoat. Specifically, hydrocarbon polymers, acrylic ester polymers, polymethacrylic acid, polyacrylic acid, polyvinyl ether, silicon-containing polymers, and fluorine-containing polymers are exemplified.

When the topcoat is peeled off, a developing solution may be used, or a remover may be used separately. As the remover, a solvent low in penetration into a resist is preferred. In view of capable of performing a peeling process at the same time with the development process of a resist, it is preferred that the topcoat can be peeled off by an alkali developing solution. From the viewpoint of performing peeling with an alkali developing solution, the topcoat is preferably acidic, but from the viewpoint of non-intermixture with the resist, it may be neutral or alkaline.

Resolution increases when there is no difference in the refractive indexes between the topcoat and the immersion liquid. In the case where the exposure light source is an ArF excimer laser (wavelength: 193 nm), it is preferred to use water as the immersion liquid. Accordingly, the refractive index of the topcoat for ArF immersion exposure is preferably nearer the refractive index of water (1.44). Further, from the viewpoint of transparency and refractive index, the thickness of the topcoat is preferably thinner.

When an organic solvent is used as the immersion liquid, the topcoat is preferably water-soluble.

In a development process, an alkali developing solution is used as follows. As the alkali developing solution of a resist composition, alkaline aqueous solutions of inorganic alkalis, e.g., sodium hydroxide, potassium hydroxide, sodium carbonate, sodium silicate, sodium metasilicate, aqueous ammonia, etc., primary amines, e.g., ethylamine, n-propylamine, etc., secondary amines, e.g., diethylamine, di-n-butylamine, etc., tertiary amines, e.g., triethylamine, methyldiethylamine, etc., alcohol amines, e.g., dimethyl-ethanolamine, triethanolamine, etc., quaternary ammonium salts, e.g., tetramethylammonium hydroxide, tetraethyl-ammonium hydroxide, etc., and cyclic amines, e.g., pyrrole, piperidine, etc., can be used.

An appropriate amount of alcohols and surfactants may be added to the above alkali developing solutions.

The alkali concentration of an alkali developing solution is generally from 0.1 to 20 mass %.

The pH of an alkali developing solution is generally from 10.0 to 15.0.

EXAMPLE

The invention will be described in further detail with reference to examples, but the invention is by no means limited thereto.

(1) Synthesis of dibenzothiophene-S-oxide

Dibenzothiophene (20.0 g) is suspended in 80.0 ml of trifluoroacetic acid at room temperature. To the suspension is slowly dropped 12.4 ml of 30% (w/v) aqueous hydrogen peroxide while cooling with ice so as to maintain the reaction temperature around 60° C. After completion of dropping, the reaction solution is stirred at room temperature for 30 minutes. After the reaction, the reaction solution is added to 1,000 ml of water to precipitate crystals. The crystals are recovered by filtration and washed with water. The obtained crystals are recrystallized with acetonitrile to obtain 19.2 g of dibenzothiophene-S-oxide.

¹H-NMR (400 MHz, CDCl₃) δ7.51 (t, 2H), 7.59 (t, 2H), 7.81 (d, 2H), 8.00 (d, 2H)

(2) Synthesis of 5-(4-methylphenyl)dibenzothiophenium acetate (A2)

While cooling with ice, 10.0 g of dibenzothiophene-S-oxide synthesized in the above step (1) is added to 30 g of diphosphorus pentoxide/methanesulfonic acid (9/1), and 10 ml of toluene is further added thereto. The reaction solution is stirred at room temperature for 6 hours, and then poured into ice water. The obtained aqueous solution is filtered, and 23 g of potassium iodide is added thereto. The crystals precipitated are recovered by filtration to obtain 9.1 g of 5-(4-methylphenyl)dibenzothiophenium iodide. The obtained 9.1 g of 5-(4-methylphenyl)dibenzothiophenium iodide is dissolved in 200 ml of methanol, and 10 ml of acetic acid is added to the reaction solution. After stirring the reaction solution at room temperature for 30 minutes, 3.9 g of silver acetate is further added thereto, and the reaction solution is further stirred at room temperature for 1 hour. After filtering the reaction solution, the mother liquor is distilled off under reduced pressure. The crystals obtained are dissolved in chloroform, and washed with water three times. After distilling off the chloroform under reduced pressure, the reaction product is recrystallized with ethyl acetate, whereby 6.2 g of 5-(4-methylphenyl)dibenzothiophenium acetate is obtained.

¹H-NMR (400 MHz, CDCl₃) δ 2.20 (s, 3H), 2.38 (s, 3H), 7.29 (d, 2H), 7.55 (d, 2H), 7.64 (t, 2H), 7.83 (t, 2H), 8.17 (d, 2H), 8.19 (d, 2H)

(3) Synthesis of 5-[4-(2-hydroxyethyl)phenyl]dibenzo-thiophenium acetate (A9)

While cooling with ice, 10.0 g of dibenzothiophene-S-oxide synthesized in the above step (1) is added to 30 g of diphosphorus pentoxide/methanesulfonic acid (9/1), and 10 ml of 2-phenylethyl acetate is further added thereto. The reaction solution is stirred at room temperature for 6 hours, and then poured into ice water. The obtained aqueous solution is filtered, and 23 g of potassium iodide is added. The crystals precipitated are recovered by filtration to obtain 11.1 g of 5-[4-(2-acetoxyethyl)phenyl]dibenzothiophenium iodide. The obtained 11.1 g of 5-[4-(2-acetoxyethyl)phenyl]-dibenzothiophenium iodide is dissolved in 200 ml of methanol, and 10.7 g of a 20% aqueous solution of tetramethylammonium hydroxide is added to the reaction solution. After stirring the reaction solution at room temperature for 2 hours, 10 ml of acetic acid is added and the reaction solution is further stirred at room temperature for 30 minutes. Further, 3.9 g of silver acetate is added to the reaction solution and stirred at room temperature for 1 hour. After filtering the reaction solution, the mother liquor is distilled off under reduced pressure. The crystals obtained are dissolved in chloroform, and washed with water three times. After distilling off the chloroform under reduced pressure, the reaction product is recrystallized with ethyl acetate/acetonitrile (10/1), whereby 6.6 g of 5-[4-(2-hydroxyethyl)phenyl]dibenzo-thiophenium acetate is obtained.

¹H-NMR (400 MHz, CDCl₃) δ 2.20 (s, 3H), 2.78 (t, 2H), 3.71 (t, 2H), 7.29 (d, 2H), 7.51 (t, 2H), 7.64 (d, 2H), 7.76 (t, 2H), 8.14 (d, 2H), 8.22 (d, 2H)

Resin (C):

The structure, molecular weight and degree of molecular weight dispersion of each resin (C) used in Examples are shown below. The number on the right hand of each repeating unit is a molar ratio, and the rest is the same as above.

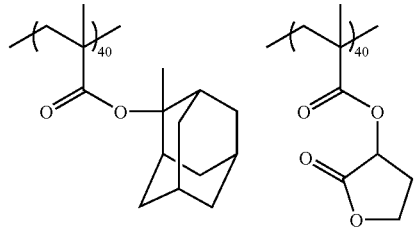

(RA-1)

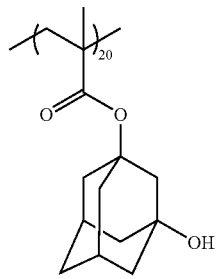

Mw = 10700
Mw/Mn = 1.81

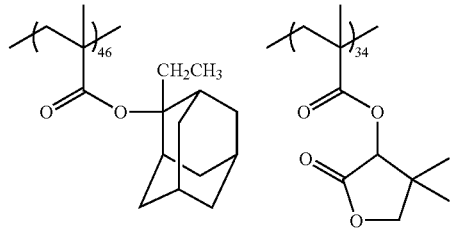

(RA-2)

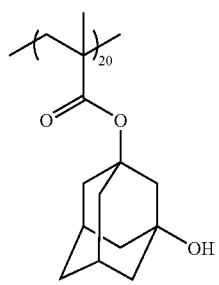

Mw = 9400
Mw/Mn = 1.78

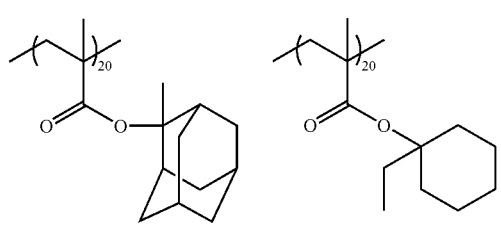

(RA-3)

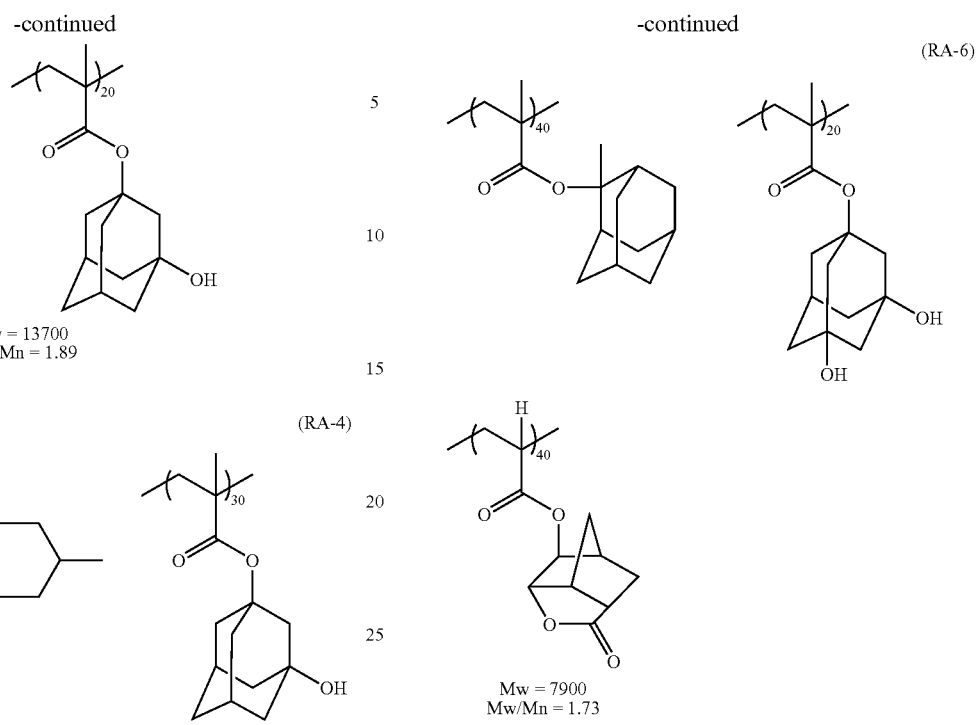
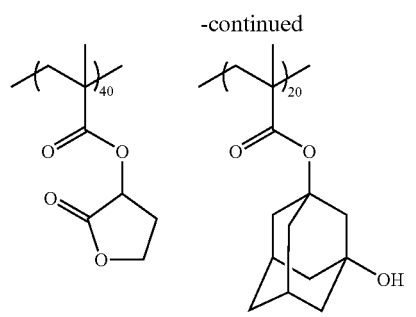
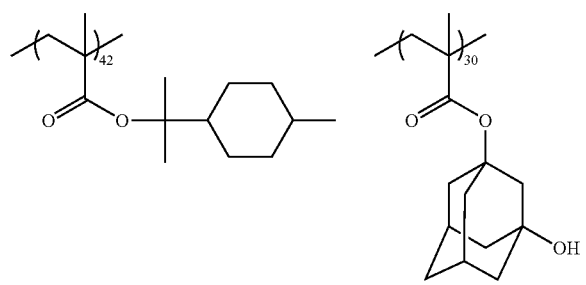
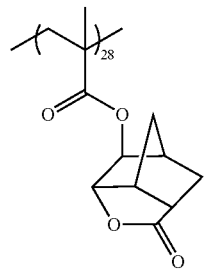
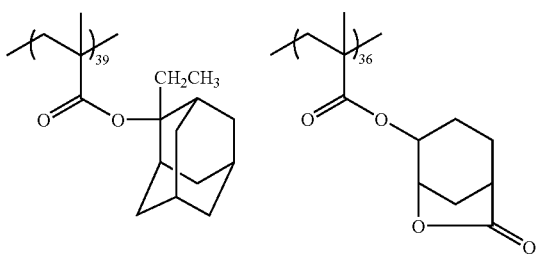
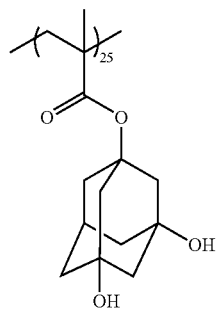

-continued
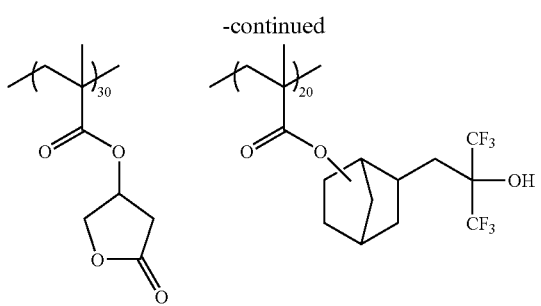
Mw = 15600
Mw/Mn = 2.03
(RA-9)
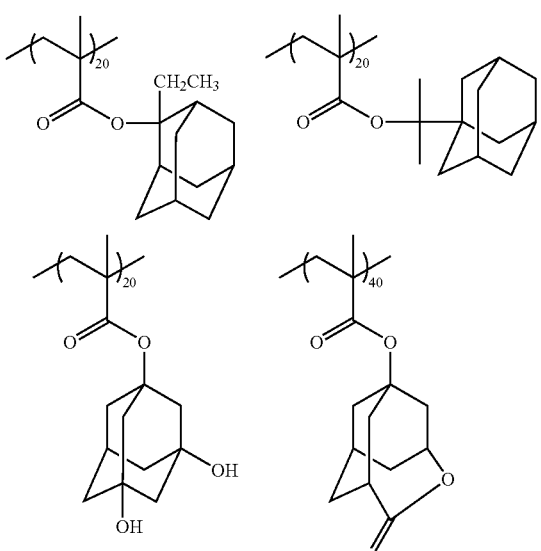
Mw = 9800
Mw/Mn = 1.86
(RA-10)
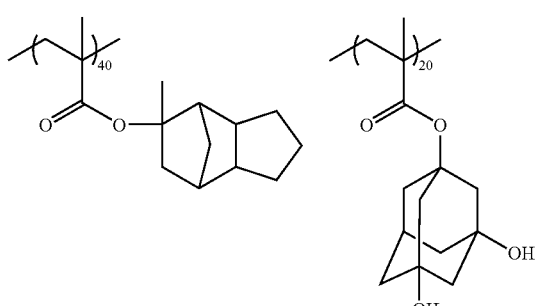
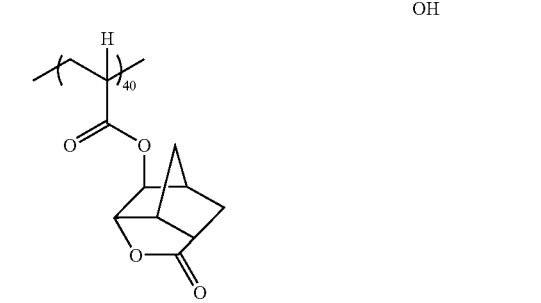
Mw = 18300
Mw/Mn = 2.10
-continued
(RA-11)
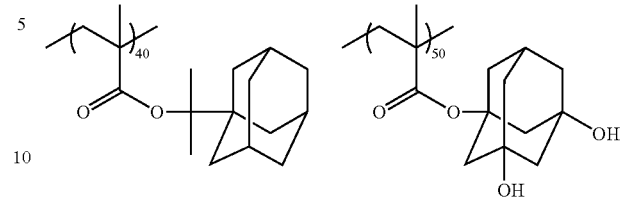
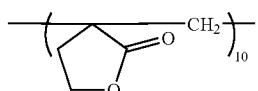
Mw = 6900
Mw/Mn = 1.71
(RA-12)
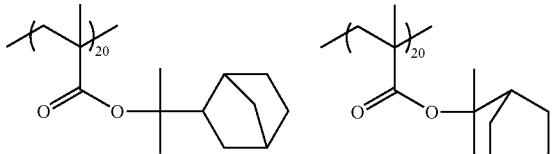
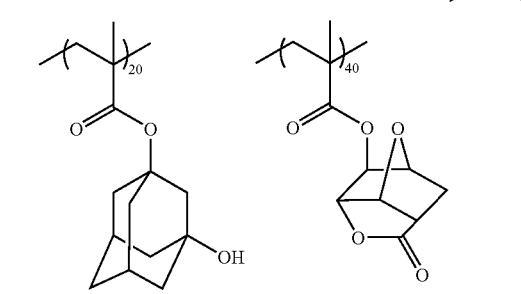
Mw = 8300
Mw/Mn = 1.81
(RA-13)
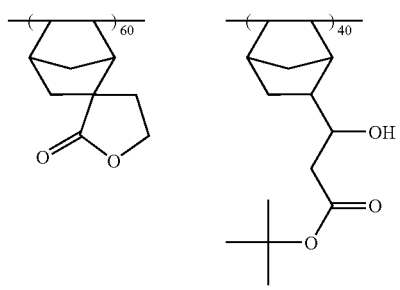
Mw = 9600
Mw/Mn = 1.81
(RA-14)
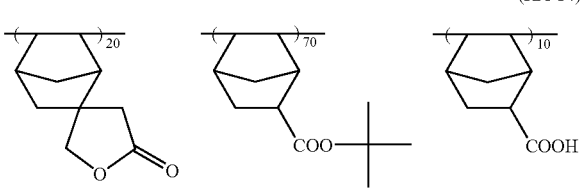
Mw = 5800
Mw/Mn = 1.69

-continued (RA-15)

Mw = 4700
Mw/Mn = 1.70

(RA-16)

Mw = 8900
Mw/Mn = 1.81

(RA-17)

Mw = 13900
Mw/Mn = 1.98

(RA-18)

-continued

Mw = 12700
Mw/Mn = 1.99

(RA-19)

Mw = 9300
Mw/Mn = 1.81

(RA-20)

Mw = 7600
Mw/Mn = 1.76

-continued
(RA-21)
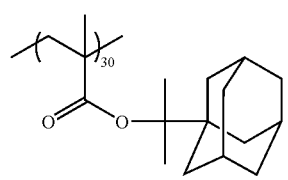 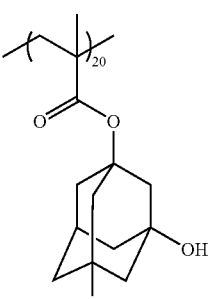
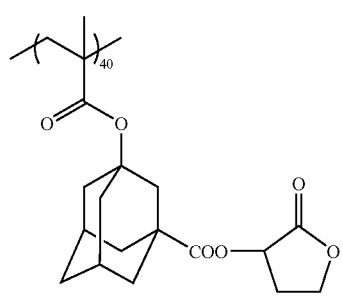 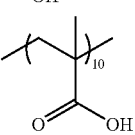
Mw = 12700
Mw/Mn = 1.86
(RA-22)
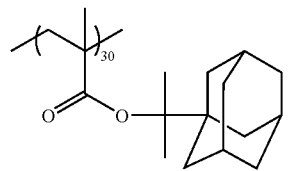 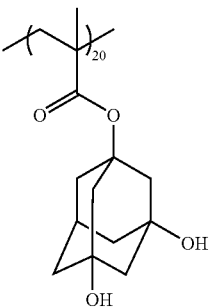
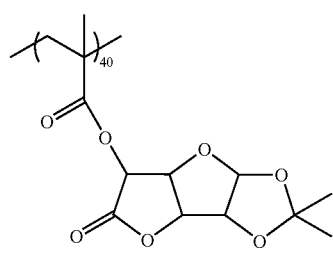 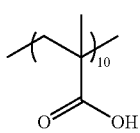
Mw = 8200
Mw/Mn = 1.75
(RA-23)
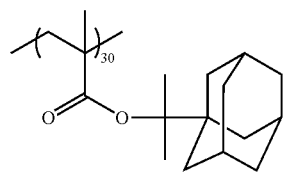 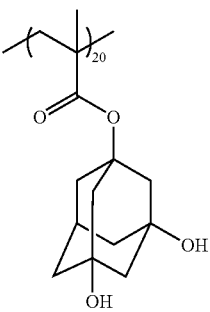
-continued
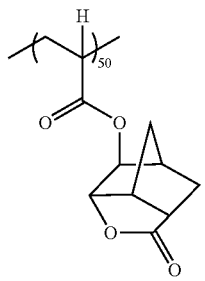
Mw = 8500
Mw/Mn = 1.77
(RA-24)
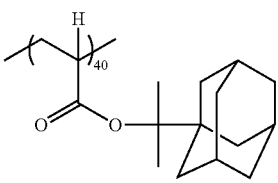 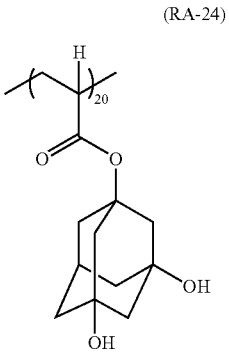
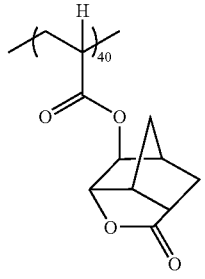
Mw = 18900
Mw/Mn = 2.13
(RA-25)
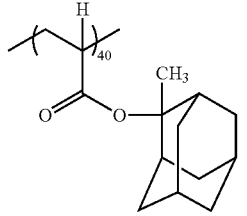
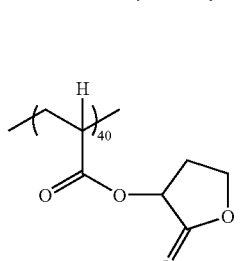
Mw = 20800
Mw/Mn = 2.25

Examples 1 to 8 and Comparative Example 1

Preparation of Resist

A solution having the concentration of solids content of 12 mass % is prepared by dissolving the components in the solvents respectively shown in Table 1, and a positive resist solution is prepared by filtrating the above-prepared solution through a polytetrafluoroethylene filter or a polyethylene filter having a pore size of 0.1 μm. The thus prepared positive resist solution is evaluated according to the following methods. The results of evaluations are shown in Table 1.

Evaluation of Resist:

gradient of the straight line part of the sensitivity curve. The greater the γ value, the better is the dissolution contrast.

Line Edge Roughness (LER):

In regard to 50 μm in the machine direction of the line pattern of 150 nm in the dose showing the above sensitivity, the distance from the intrinsic base line of the edge is measured at arbitrary 30 points with a scanning electron microscope (S-9220, manufactured by Hitachi, Ltd.), and the standard deviation is found, from which 3σ is computed.

Pattern Profile:

Taking the dose required to reproduce the mask pattern of line and space of line width of 150 nm as the optimal dose, a pattern profile at the optimal dose is observed with a scanning electron microscope (SEM).

TABLE 1

ArF Positive Resist

| Ex. No. | Compound A (g) | Acid Generator (g) | Resin (10 g) | Basic Compound (g) | Surfactant (0.002 g) | Solvent (mass ratio) | Sensitivity (mJ/cm$^2$) | γ Value | LER (nm) |
|---|---|---|---|---|---|---|---|---|---|
| Ex. 1 | A2 (0.20) | z2 (0.3) | RA-20 | — | W-1 | A1/B1 (60/40) | 26.3 | 5.1 | 5.3 |
| Ex. 2 | A7 (0.15) | z5 (0.3) | RA-23 | — | W-2 | A2/B2 (60/40) | 24.3 | 5.3 | 5.4 |
| Ex. 3 | A9 (0.05) | z11/z42 (0.4/0.05) | RA-9 | — | W-1 | A3/B1 (80/20) | 23.9 | 5.2 | 5.6 |
| Ex. 4 | A21 (0.10) | z12 (0.2) | RA-24 | — | W-3 | A4/B1 (50/50) | 22.8 | 5.5 | 5.0 |
| Ex. 5 | A27 (0.30) | z13/z26 (0.4/0.05) | RA-25 | — | W-1 | A1/B1 (60/40) | 21.5 | 5.6 | 4.9 |
| Ex. 6 | A28 (0.04) | z19/z13 (0.3/0.2) | RA-8 | C-1 (0.02) | W-3 | A2/B2 (60/40) | 20.6 | 5.9 | 4.6 |
| Ex. 7 | A39 (0.10) | z31/z5 (0.3/0.1) | RA-2 | C-3 (0.03) | W-1 | A1/B1 (60/40) | 20.3 | 6.0 | 4.8 |
| Ex. 8 | A57 (0.15) | z36/z32 (0.3/0.05) | RA-23 | — | W-4 | A1/B2 (70/30) | 20.0 | 6.2 | 4.9 |
| Comp. Ex. 1 | A'-1 (0.20) | Z2 (0.3) | RA-20 | — | W-1 | A1/B1 (60/40) | 31.0 | 3.3 | 8.5 |

An antireflection film DUV-42 (manufactured by Brewer Science) is uniformly coated on a silicon substrate having been subjected to hexamethyldisilazane treatment in a thickness of 600 Å by a spin coater, and is dried on a hot plate at 100° C. for 90 seconds, and then by heating at 190° C. for 240 seconds. After that, each positive resist solution is coated thereon by a spin coater and dried at 120° C. for 90 seconds to form a resist film having a thickness of 0.25 μm.

The resist film is subjected to exposure through a mask with an ArF excimer laser stepper (NA: 0.6, manufactured by ISI Co.), and heated on a hot plate at 120° C. for 90 seconds just after exposure. Further, the resist film is developed with a 2.38 mass % tetramethylammonium hydroxide aqueous solution at 23° C. for 60 seconds, is rinsed with pure water for 30 seconds, and then dried to form a line pattern.

Sensitivity and Resolution (γ Value):

The resist film is subjected to areal exposure with varying the exposure dose 0.5 by 0.5 mJ within the range of exposure dose of from 10 to 40 mJ/cm$^2$, and further to baking at 110° C. for 90 seconds. After that, a dissolution rate of the resist film at each exposure dose is measured with a 2.38 mass % tetramethylammonium hydroxide (TMAH) aqueous solution to obtain a sensitivity curve.

In the sensitivity curve, the exposure dose at the time when the dissolution rate of the resist is saturated is taken as sensitivity, and dissolution contrast (γ value) is computed from the The abbreviations of the components are as follows.

Acid Generators:

Acid generators are as shown above.

Acid generator (A'-1) used in Comparative Examples is a compound shown below.

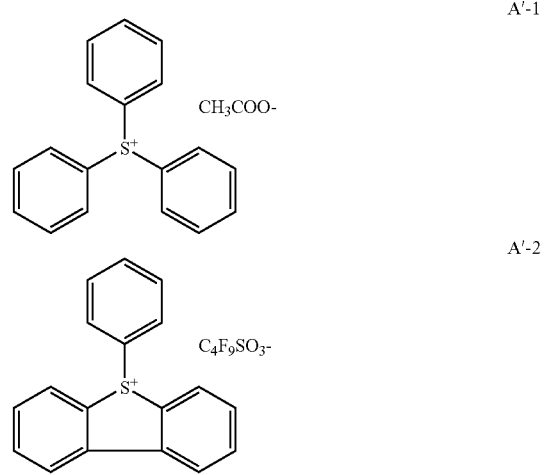

A'-1

A'-2

Basic Compounds:

C-1: 2,4,5-Triphenylimidazole

C-2: Triphenylsulfonium acetate

C-3: N-Hydroxyethylpiperidine

Surfactants:

W-1: Megafac F176 (fluorine surfactant, manufactured by Dainippon Ink and Chemicals Inc.)

W-2: Megafac R08 (fluorine/silicon surfactant, manufactured by Dainippon Ink and Chemicals Inc.)

W-3: Polysiloxane polymer KP-341 (silicon surfactant, manufactured by Shin-Etsu Chemical Co., Ltd.)

W-4: Troy Sol S-366 (manufactured by Troy Chemical Co., Ltd.)

Solvents:

A1: Propylene glycol monomethyl ether acetate

A2: 2-Heptanone

A3: Cyclohexanone

A4: γ-Butyrolactone

B1: Propylene glycol monomethyl ether

B2: Ethyl lactate

From the results shown in Table 1, it is apparent that the photosensitive compositions in the invention are excellent in sensitivity, γ value and pattern profile in ArF exposure.

Evaluation of Immersion Exposure:

Preparation of Resist:

A solution having the concentration of solids content of 8 mass % is prepared by dissolving each of the components in Examples 1 to 8 in the solvents respectively shown in Table 1, and each positive resist solution is prepared by filtrating the above solution through a polyethylene filter having a pore size of 0.1 μm. The positive resist solution prepared is evaluated according to the following method.

Evaluation of Resolution:

An organic antireflection film ARC29A (manufactured by Nissan Chemical Industries, Ltd.) is coated on a silicon wafer, and the coating is baked at 205° C. for 60 seconds to thereby form an antireflection film having a thickness of 78 nm. The above-prepared positive resist solution is coated on the antireflection film and baked at 120° C. for 60 seconds to form a resist film having a thickness of 150 nm. The obtained wafer is subjected to two-beam interference exposure with pure water as the immersion liquid (wet exposure). In the two-beam interference exposure (wet exposure), as shown in the drawing, wafer 10 having the antireflection film and the resist film is subjected to exposure via prism 8 and immersion liquid 9 (pure water) with laser 1, diaphragm 2, shutter 3, three reflection mirrors 4, 5 and 6, and condenser lens 7. The wavelength of laser 1 is 193 nm, and prism 8 is used for forming line and space pattern of 65 nm. Immediately after exposure, the wafer is baked at 120° C. for 60 seconds, and then developed with a 2.38 mass % of tetramethylammonium hydroxide aqueous solution for 60 seconds, rinsed with pure water, and dried by spinning to obtain a resist pattern. It is confirmed that line and space of 65 nm is resolved from the observation of the obtained resist pattern with a scanning electron microscope S-9260 (manufactured by Hitachi, Ltd.).

The compositions in Examples 1 to 8 show good image forming performance even in the exposure method via an immersion liquid.

Examples 9 to 14 and Comparative Example 2

(1) Formation of Lower Resist Layer

FHi-028DD resist (resist for i-ray, manufactured by Fuji Film Olin Co., Ltd.) is coated on a 6 inch silicon wafer with a spin coater Mark 8 (manufactured by Tokyo Electron Limited) and baked at 90° C. for 90 seconds, whereby a uniform film having a thickness of 0.55 μm is obtained.

The obtained film is further baked at 200° C. for 3 minutes to thereby form a lower resist layer having a thickness of 0.40 μm.

(2) Formation of Upper Resist Layer

A solution having the concentration of solids content of 11 mass % is prepared by dissolving the components in the solvents respectively shown in Table 2 below. The resulting solution is filtrated through a membrane filter having a pore size of 0.1 μm to prepare a composition for an upper resist layer.

The upper resist layer composition is coated on the lower resist layer in the same manner as in the lower layer, and heated at 130° C. for 90 seconds, whereby an upper resist layer having a thickness of 0.20 μm is formed.

Resins (SI-1) to (SI-5) in Table 2 are as follows.

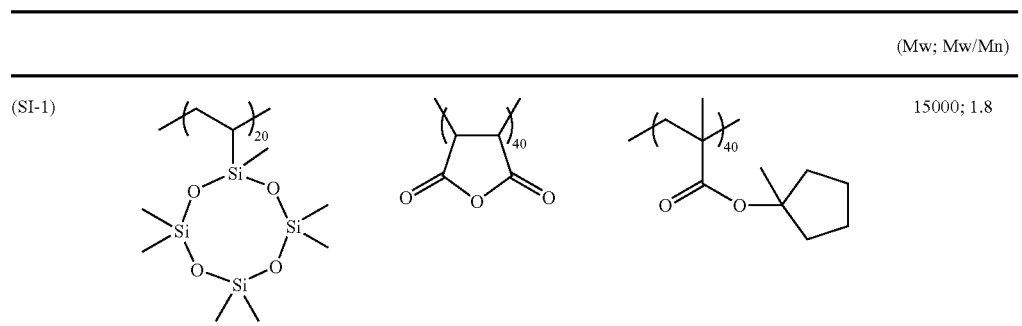

-continued

| | | (Mw; Mw/Mn) |
|---|---|---|
| (SI-2) | 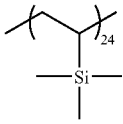 | 14500; 1.7 |
| (SI-3) | 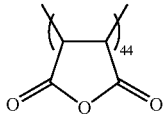 | 9600; 1.9 |
| (SI-4) | 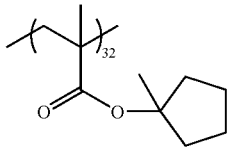 | 8900; 2.0 |
| (SI-5) | 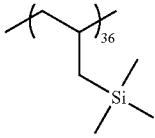 | 10800; 2.0 |

(3) Evaluation of Resist

The thus-obtained wafer is subjected to exposure with ArF Excimer Stepper 9300 (manufactured by ISI Co.) attached with a resolution mask with varying the exposure dose. Subsequently, after heating at 120° C. for 90 seconds, the wafer is developed with a 2.38 mass % tetrahydroammonium hydroxide developing solution for 60 seconds, rinsed with distilled water and dried to form an upper layer pattern. The resist is evaluated in the same manner as in Example 1 (ArF positive exposure).

The results obtained are shown in Table 2.

TABLE 2

Si Positive Resist

| Ex. No. | Compound A (g) | Acid Generator (g) | Resin (10 g) | Basic Compound (g) | Surfactant (0.002 g) | Solvent (mass ratio) | Sensitivity (mJ/cm$^2$) | γ Value | LER (nm) |
|---|---|---|---|---|---|---|---|---|---|
| Ex. 9 | A2 (0.20) | z2 (0.3) | SI-1 | — | W-1 | A1/A3 (60/40) | 25.6 | 5.0 | 6.8 |
| Ex. 10 | A9 (0.10) | z9/z12 (0.2/0.1) | SI-1 | — | W-1 | A2/A3 (70/30) | 24.6 | 5.2 | 6.5 |
| Ex. 11 | A25 (0.10) | z12/z25 (0.3/0.05) | SI-2 | — | W-2 | A1/A2 (60/40) | 23.3 | 5.3 | 6.6 |
| Ex. 12 | A30 (0.22) | z16/z46 (0.4/0.1) | SI-3 | — | W-3 | A1/A4 (80/20) | 24.0 | 5.2 | 6.3 |
| Ex. 13 | A36 (0.15) | z23 (0.3/0.2) | SI-4 | C-1 (0.02) | W-2 | A2/A4 (60/40) | 23.2 | 5.4 | 5.9 |
| Ex. 14 | A66 (0.10) | z28/z46 (0.3/0.1) | SI-5 | — | W-1 | A2/A3 (70/30) | 22.3 | 5.6 | 5.5 |
| Comp. Ex. 2 | A'-1 (0.20) | z1 (0.3) | SI-1 | — | W-1 | A1/A3 (60/40) | 33.3 | 3.6 | 11.3 |

From the results shown in Table 2, it is apparent that the photosensitive compositions in the invention have also excellent performances when used as two-layered resists.

Examples 15 to 20 and Comparative Example 3

Preparation of Resist

A positive resist solution having the concentration of solids content of 14 mass % is prepared by dissolving the components in the solvents respectively shown in Table 3 below, and filtrating the solution through a polytetrafluoroethylene filter having a pore size of 0.1 μm.

Evaluation of Resist:

The prepared positive resist solution is uniformly coated on a silicone substrate having been subjected to hexamethyldisilazane treatment by a spin coater, and dried by heating on a hot plate at 120° C. for 90 seconds to form a resist film having a thickness of 0.4 μm.

The resist film is subjected to pattern exposure through a mask for line and space with a KrF excimer laser stepper (NA: 0.63), and heated on a hot plate at 110° C. for 90 seconds just after exposure. Further, the resist film is developed with a 2.38 mass % tetramethylammonium hydroxide aqueous solution at 23° C. for 60 seconds, rinsed with pure water for 30 seconds, and then dried to form a line pattern.

Sensitivity and Resolution (γ Value):

The resist film is subjected to areal exposure with varying the exposure dose 0.5 by 0.5 mJ within the range of exposure dose of from 10 to 40 mJ/cm$^2$, and further to baking at 110° C. for 90 seconds. After that, a dissolution rate of the resist film at each dose is measured with a 2.38 mass % tetramethylammonium hydroxide (TMAH) aqueous solution to obtain a sensitivity curve.

In the sensitivity curve, the exposure dose at the time when the dissolution rate of the resist is saturated is taken as sensitivity, and dissolution contrast (γ value) is computed from the gradient of the straight line part of the sensitivity curve. The greater the γ value, the better is the dissolution contrast.

Line Edge Roughness (LER):

In regard to 50 μm in the machine direction of the line pattern of 180 nm in the irradiation dose showing the above sensitivity, the distance from the intrinsic base line of the edge is measured at arbitrary 30 points with a scanning electron microscope (S-9220, manufactured by Hitachi, Ltd.), and the standard deviation is found, from which 3σ is computed.

Pattern Profile:

Taking the exposure dose required to reproduce the mask pattern of line and space of line width of 180 nm as the optimal dose, a pattern profile at the optimal dose is observed with a scanning electron microscope (SEM).

The results obtained are shown in Table 3 below.

TABLE 3

KrF Positive Resist

| Ex. No. | Compound A (g) | Acid Generator (g) | Resin (10 g) | Basic Compound (g) | Surfactant (0.002 g) | Solvent (mass ratio) | Sensitivity (mJ/cm$^2$) | γ Value | LER (nm) |
|---|---|---|---|---|---|---|---|---|---|
| Ex. 15 | A3 (0.20) | z1 (0.3) | R-2 | — | W-1 | A1/B1 (60/40) | 20.5 | 5.5 | 5.6 |
| Ex. 16 | A9 (0.10) | z4/z5 (0.3/0.1) | R-7 | — | W-2 | A1/B1 (80/20) | 18.0 | 5.8 | 5.4 |
| Ex. 17 | A18 (0.20) | z10/z26 (0.2/0.05) | R-8 | — | W-1 | A2/B2 (70/30) | 18.5 | 5.6 | 5.1 |
| Ex. 18 | A24 (0.30) | z14/z35 (0.4/0.2) | R-9 | — | W-3 | A2/B2 (60/40) | 17.3 | 5.9 | 5.2 |

TABLE 3-continued

| | | | KrF Positive Resist | | | | | | |
|---|---|---|---|---|---|---|---|---|---|
| Ex. No. | Compound A (g) | Acid Generator (g) | Resin (10 g) | Basic Compound (g) | Surfactant (0.002 g) | Solvent (mass ratio) | Sensitivity (mJ/cm$^2$) | γ Value | LER (nm) |
| Ex. 19 | A36 (0.10) | z18/z42 (0.2-0.05) | R-14 | C-1 (0.03) | W-1 | A3/B2 (60/40) | 16.5 | 6.3 | 4.8 |
| Ex. 20 | A63 (0.05) | z25/z28 (0.2/0.2) | R-17 | — | W-3 | A4/B1 (60/40) | 15.3 | 6.5 | 4.6 |
| Comp. Ex. 3 | A'-1 (0.20) | z1 (0.3) | R-2 | — | W-1 | A1/B1 (70/30) | 27.8 | 3.6 | 10.1 |

Resins (R-2), (R-7), (R-8), (R-9), (R-14) and (R-17) shown in Table 3 are the resins exemplified above. The molar ratio of repeating units and weight average molecular weight of each resin are shown in Table 4 below.

and filtrating the solution through a polytetrafluoroethylene filter having a pore size of 0.1 μm.

Each of the prepared negative resist solutions is evaluated in the same manner as in Example 15 (KrF positive exposure), and the results obtained are shown in Table 5.

TABLE 5

| | | | KrF Negative Resist | | | | | | |
|---|---|---|---|---|---|---|---|---|---|---|
| Ex. No. | Compound A (g) | Acid Generator (g) | Resin (10 g) | Crosslinking Agent (g) | Basic Compound (g) | Surfactant (0.002) | Solvent (mass ratio) | Sensitivity (mJ/cm$^2$) | γ Value | LER (nm) |
| Ex. 21 | A3 (0.20) | z1 (0.3) | P-1 | CL-1 (3.0) | — | W-1 | A1/B1 (60/40) | 20.6 | 6.1 | 13.3 |
| Ex. 22 | A9 (0.10) | z4 (0.4) | P-1 | CL-2 (2.5) | — | W-2 | A1/B1 (80/20) | 20.1 | 6.3 | 12.6 |
| Ex. 23 | A18 (0.20) | z10 (0.25) | P-2 | CL-3 (2.0) | — | W-1 | A2/B2 (70/30) | 19.5 | 6.4 | 11.7 |
| Ex. 24 | A24 (0.30) | z14/z27 (0.4/0.2) | P-2 | CL-4 (3.0) | C-1 (0.02) | W-3 | A2/B2 (60/40) | 18.9 | 6.5 | 11.5 |
| Ex. 25 | A36 (0.10) | z18/z31 (0.2/0.05) | P-3 | CL-5 (3.0) | C-3 (0.03) | W-1 | A3/B2 (60/40) | 18.6 | 6.5 | 11.3 |
| Ex. 26 | A63 (0.05) | z25/z38 (0.2/0.2) | P-3 | CL-6 (2.5) | — | W-3 | A4/B1 (60/40) | 18.5 | 6.8 | 11.0 |
| Comp. Ex. 4 | A'-1 (0.20) | z1 (0.3) | P-3 | CL-1 (3.0) | — | W-1 | A1/B1 (70/30) | 30.2 | 4.5 | 18.5 |

TABLE 4

| Resin | Molar Ratio of Repeating Units (correspondent from the left hand in order) | Weight Average Molecular Weight Mw |
|---|---|---|
| R-2 | 60/20/20 | 12,000 |
| R-7 | 60/30/10 | 18,000 |
| R-8 | 60/20/20 | 12,000 |
| R-9 | 60/40 | 13,000 |
| R-14 | 60/15/25 | 12,000 |
| R-17 | 80/20 | 15,000 |

From the results shown in Table 3, it is apparent that the photosensitive compositions in the invention have also excellent performances as the positive resist compositions in KrF excimer laser exposure.

Examples 21 to 26 and Comparative Example 4

Preparation of Resist

A negative resist solution having the concentration of solids content of 14 mass % is prepared by dissolving the components in the solvents respectively shown in Table 5 below, The structures, molecular weights, and molecular weight distributions of the alkali-soluble resins and crosslinking agents in Table 5 are shown below.

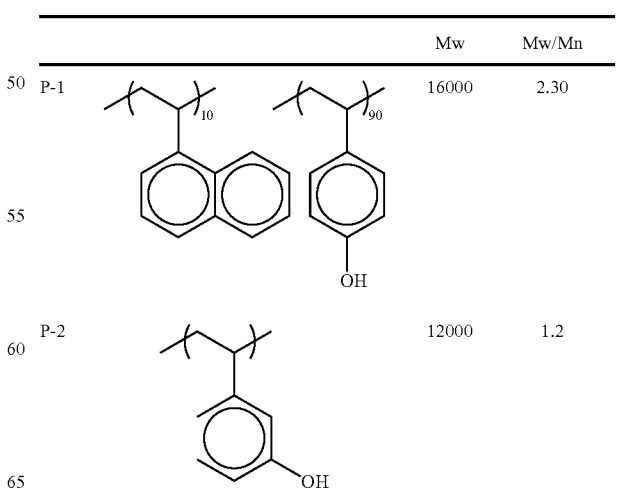

-continued

| | | Mw | Mw/Mn |
|---|---|---|---|
| P-3 | 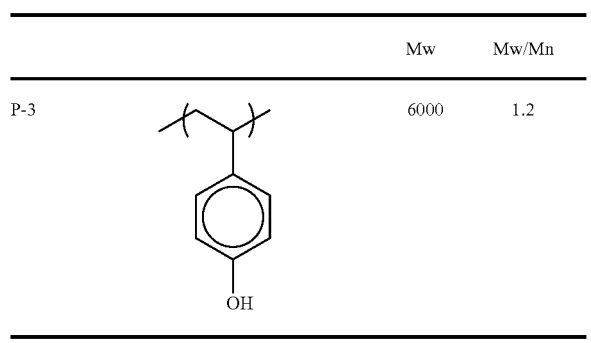 | 6000 | 1.2 |

VP-5000 (manufactured by Nippon Soda Co., Ltd.)

CL-1
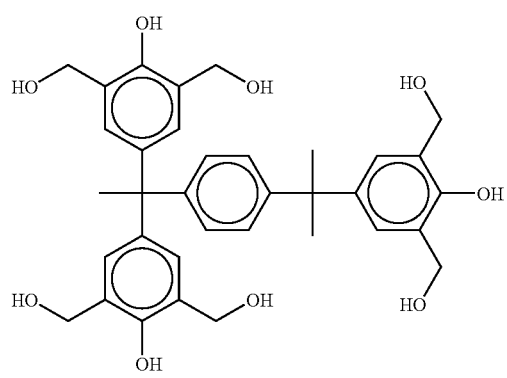

CL-2
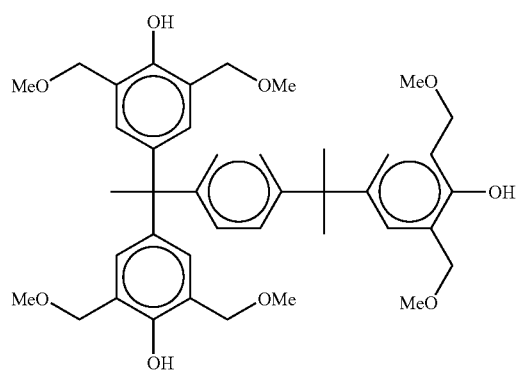

CL-3
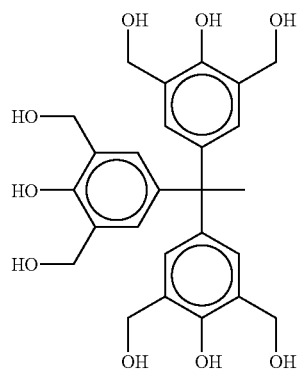

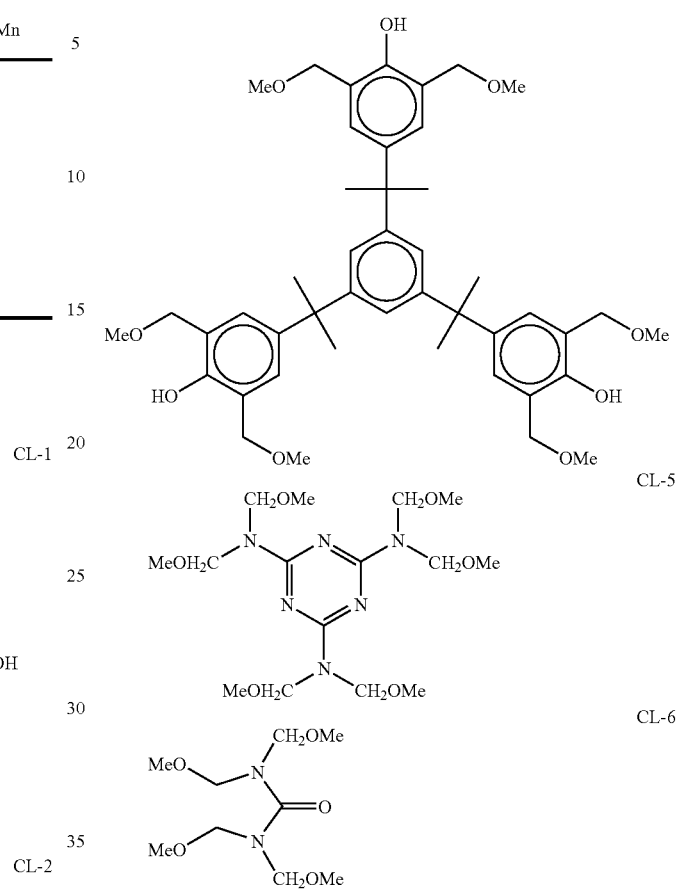

From the results shown in Table 5, it can be seen that the photosensitive compositions in the invention have also excellent performances as the negative resist compositions in KrF excimer laser exposure.

Examples 27 to 32 and Comparative Example 5

Preparation of Resist

A positive resist solution having the concentration of solids content of 12 mass % is prepared by dissolving the components in the solvents respectively shown in Table 3, and filtrating the solution through a polytetrafluoroethylene filter having a pore size of 0.1 μm.

Evaluation of Resist:

The prepared positive resist solution is uniformly coated on a silicon substrate having been subjected to hexamethyldisilazane treatment by a spin coater, and dried by heating on a hot plate at 120° C. for 60 seconds to form a resist film having a thickness of 0.3 μm.

The resist film is irradiated with an electron beam projection lithographic apparatus (accelerating voltage: 100 keV, manufactured by Nikon Corporation), and heated on a hot plate at 110° C. for 90 seconds just after irradiation. Further, the resist film is developed with a 2.38 mass % tetramethylammonium hydroxide aqueous solution at 23° C. for 60 seconds, rinsed with pure water for 30 seconds, and then dried to form a line and space pattern. Performances are evaluated in the same manner as in Example 1.

Sensitivity and Resolution (γ Value):

The resist film is subjected to areal exposure with varying the exposure dose 0.1 by 0.1 µC/cm² within the range of exposure dose of from 0 to 10 µC/cm², and further to baking at 110° C. for 90 seconds. After that, a dissolution rate of the resist film at each exposure dose is measured with a 2.38 mass % tetramethylammonium hydroxide (TMAH) aqueous solution to obtain a sensitivity curve.

In the sensitivity curve, the exposure dose at the time when the dissolution rate of the resist is saturated is taken as sensitivity, and dissolution contrast (γ value) is computed from the gradient of the straight line part of the sensitivity curve.

Line Edge Roughness (LER):

In regard to 50 µm in the machine direction of the line pattern of 150 nm in the irradiation dose showing the above sensitivity, the distance from the intrinsic base line of the edge is measured at arbitrary 30 points with a scanning electron microscope (S-9220, manufactured by Hitachi, Ltd.), and the standard deviation is found, from which 3σ is computed.

Outgassing Performance (the Coefficient of Fluctuation in the Film Thickness after Exposure):

The resist film is irradiated with 2.0 times the irradiation dose at the sensitivity determined by areal exposure with electron beam (µC/cm²), and the thickness of the film after exposure (before post-baking) is measured, and the coefficient of fluctuation from the film thickness at unexposed time is found according to the following equation.

Coefficient of fluctuation in film thickness (%)=[(film thickness at unexposed time−film thickness after exposure)/film thickness at unexposed time]×100

The results of evaluation are shown in Table 6 below.

TABLE 6

Electron Beam Exposure of Positive Resist

| | Evaluation | | | |
|---|---|---|---|---|
| Example No. | Sensitivity (µC/cm²) | γ Value | LER (nm) | Outgassing Performance (evaluation of film thickness) (%) |
| Example 27 | 4.5 | 7.6 | 6.5 | 3.3 |
| Example 28 | 4.6 | 7.8 | 5.9 | 3.5 |
| Example 29 | 4.2 | 8.0 | 5.7 | 3.1 |
| Example 30 | 4.1 | 8.2 | 5.4 | 2.9 |
| Example 31 | 3.8 | 8.0 | 5.2 | 2.8 |
| Example 32 | 3.5 | 8.3 | 5.1 | 2.6 |
| Comparative Example 5 | 8.6 | 4.3 | 10.4 | 10.5 |

From the results shown in Table 6, it can be seen that the photosensitive compositions in the invention also have excellent performances as the positive resist compositions for electron beam irradiation.

Examples 33 to 38 and Comparative Example 6

Preparation of Resist

A negative resist solution having the concentration of solids content of 12 mass % is prepared by dissolving the components in the solvents respectively shown in Table 5, and filtrating the solution through a polytetrafluoroethylene filter having a pore size of 0.1 µm.

Evaluation of Resist:

The prepared negative resist solution is uniformly coated on a silicon substrate having been subjected to hexamethyldisilazane treatment by a spin coater, and dried by heating on a hot plate at 120° C. for 60 seconds to form a resist film having a thickness of 0.3 µm.

The resist film is irradiated with an electron beam projection lithographic apparatus (accelerating voltage: 100 keV, manufactured by Nikon Corporation), and heated on a hot plate at 110° C. for 90 seconds just after irradiation. Further, the resist film is developed with a 2.38 mass % tetramethylammonium hydroxide aqueous solution at 23° C. for 60 seconds, rinsed with pure water for 30 seconds, and then dried to form a line and space pattern. Performances are evaluated in the same manner as in Example 27 (electron beam exposure of positive resist).

The results obtained are shown in Table 7 below.

TABLE 7

Electron Beam Exposure of Negative Resist

| | Evaluation | | | |
|---|---|---|---|---|
| Example No. | Sensitivity (µC/cm²) | γ Value | LER (nm) | Outgassing Performance (evaluation of film thickness) (%) |
| Example 33 | 5.6 | 7.3 | 10.0 | 3.5 |
| Example 34 | 4.6 | 7.8 | 9.5 | 3.2 |
| Example 35 | 4.3 | 7.9 | 9.3 | 3.1 |
| Example 36 | 4.1 | 8.3 | 9.5 | 3.0 |
| Example 37 | 4.0 | 8.5 | 9.1 | 2.5 |
| Example 38 | 3.8 | 8.6 | 8.6 | 2.4 |
| Comparative Example 6 | 9.6 | 5.1 | 17.3 | 10.1 |

From the results shown in Table 7, it can be seen that the photosensitive compositions in the invention have also excellent performances as the negative resist compositions for electron beam irradiation.

Examples 39 to 44 and Comparative Example 7

A positive resist solution having the concentration of solids content of 8 mass % is prepared by dissolving the components in the solvents respectively shown in Table 3, and filtrating the solution through a polytetrafluoroethylene filter having a pore size of 0.1 µm. Evaluations are performed as follows.

Evaluation of Resist:

The prepared positive resist solution is uniformly coated on a silicon substrate having been subjected to hexamethyldisilazane treatment by a spin coater, and dried by heating on a hot plate at 120° C. for 60 seconds to form a resist film having a thickness of 0.15 µm.

Sensitivity and γ Value:

The obtained resist film is subjected to areal exposure with EUV ray (wavelength: 13 nm) with varying the exposure dose 0.5 by 0.5 mJ within the range of dose of from 0 to 10.0 mJ, and the resist film is further baked at 110° C. for 90 seconds. After that, a dissolution rate of the resist film at each exposure dose is measured with a 2.38 mass % tetramethylammonium hydroxide (TMAH) aqueous solution to obtain a sensitivity curve.

In the sensitivity curve, the exposure amount at the time when the dissolution rate of the resist is saturated is taken as sensitivity, and dissolution contrast (γ value) is computed from the gradient of the straight line part of the sensitivity curve. The greater the γ value, the better is the dissolution contrast.

Outgassing Performance (the Coefficient of Fluctuation in the Film Thickness after Exposure):

The resist film is irradiated with 2.0 times the dose of irradiation at the sensitivity determined by areal exposure with EUV (mJ/cm²), and the thickness of the film after exposure (before post-baking) is measured, and the coefficient of fluctuation from the film thickness at unexposed time is found according to the following equation.

Coefficient of fluctuation in film thickness (%)=[(film thickness at unexposed time–film thickness after exposure)/film thickness at unexposed time]×100

The results of evaluation are shown in Table 8 below.

TABLE 8

EUV Exposure of Positive Resist

| Example No. | Evaluation | | |
|---|---|---|---|
| | Sensitivity (mJ/cm²) | γ Value | Outgassing Performance (evaluation of film thickness) (%) |
| Example 39 | 6.3 | 6.1 | 2.3 |
| Example 40 | 6.0 | 6.3 | 2.2 |
| Example 41 | 5.8 | 6.4 | 2.6 |
| Example 42 | 5.6 | 6.4 | 2.4 |
| Example 43 | 5.5 | 6.5 | 2.3 |
| Example 44 | 5.1 | 6.8 | 2.5 |
| Comparative Example 7 | 10.5 | 3.5 | 11.0 |

Examples 45 to 50 and Comparative Example 8

A negative resist solution having the concentration of solids content of 8 mass % is prepared by dissolving the components in the solvents respectively shown in Table 5, and filtrating the solution through a polytetrafluoroethylene filter having a pore size of 0.1 μm. Each of the prepared resists is evaluated as follows.

Evaluation of Resist:

The prepared negative resist solution is uniformly coated on a silicon substrate having been subjected to hexamethyldisilazane treatment by a spin coater, and dried by heating on a hot plate at 120° C. for 60 seconds to form a resist film having a thickness of 0.15 μm.

Sensitivity and γ Value:

The obtained resist film is subjected to areal exposure with EUV ray (wavelength: 13 nm) with varying exposure dose 0.5 by 0.5 mJ within the range of exposure dose of from 0 to 10.0 mJ, and the resist film is further baked at 110° C. for 90 seconds. After that, a dissolution rate of the resist film at each exposure dose is measured with a 2.38 mass % tetramethylammonium hydroxide (TMAH) aqueous solution to obtain a sensitivity curve.

Evaluation was performed in the same manner as in Example 39 (EUV exposure of positive resist). The results obtained are shown in Table 9 below.

TABLE 9

EUV Exposure of Negative Resist

| Example No. | Evaluation | | |
|---|---|---|---|
| | Sensitivity (mJ/cm²) | γ Value | Outgassing Performance (evaluation of film thickness) (%) |
| Example 45 | 5.6 | 5.4 | 2.9 |
| Example 46 | 5.3 | 5.6 | 2.5 |
| Example 47 | 5.4 | 5.4 | 2.6 |
| Example 48 | 5.5 | 5.9 | 2.4 |
| Example 49 | 5.1 | 6.1 | 2.3 |
| Example 50 | 4.9 | 6.2 | 2.2 |
| Comparative Example 8 | 10.3 | 3.2 | 11.2 |

From the results shown in Tables 8 and 9, it can be seen that the resist compositions in the invention are high in both sensitivity and contrast and excellent in outgassing performance in the characteristic evaluation by irradiation with EUV ray as compared with comparative compositions.

The invention can provide a photosensitive composition excellent in sensitivity, resolution, line edge roughness and outgassing characteristics; a compound for use in the photosensitive composition; and a pattern forming method with the photosensitive composition.

The entire disclosure of each and every foreign patent application from which the benefit of foreign priority has been claimed in the present application is incorporated herein by reference, as if fully set forth.

What is claimed is:
1. A photosensitive composition comprising:
(A) a compound represented by the following formula (I):

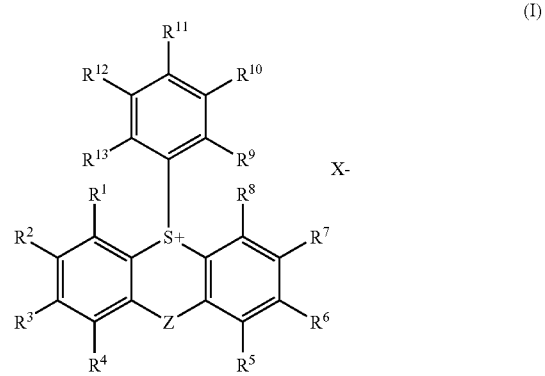

wherein
$R^1$ to $R^{13}$ each independently represents a hydrogen atom or a substituent;
Z represents a single bond, an alkylene group, an arylene group, an ether group or a thioether group;
$X^-$ represents an anion containing a proton acceptor functional group; and
the proton acceptor functional group is a functional group having a basicity selected from the group consisting of an amino group, an anilino group, a pyridine group, an amidino group and a guanidino group.

2. The photosensitive composition according to claim 1, further comprising:
(B) a compound which generates an acid by decomposition of the compound upon irradiation with an actinic ray or radiation.

3. The photosensitive composition according to claim 2, wherein the compound (B) is a sulfonium compound.

4. The photosensitive composition according to claim 2, wherein the compound (B) contains a sulfonate anion.

5. The photosensitive composition according to claim 1, further comprising:
(C) a resin, of which a solubility in an alkali developing solution increases by decomposition of the resin by action of an acid.

6. The photosensitive composition according to claim 5, wherein the resin (C) contains at least one of an alicyclic structure and an aromatic cyclic structure.

7. The photosensitive composition according to claim 1, further comprising:
(D) a resin which is soluble in an alkali developing solution; and
(E) an acid crosslinking agent which crosslinks with the resin (D) by action of an acid.

8. The photosensitive composition according to claim 1, further comprising:
(F) a basic compound.

9. The photosensitive composition according to claim 1, further comprising:
(G) at least one of a fluorine surfactant and a silicon surfactant.

10. The photosensitive composition according to claim 1, further comprising:
a solvent.

11. The photosensitive composition according to claim 10, wherein the solvent comprises a propylene glycol monomethyl ether acetate.

12. The photosensitive composition according to claim 11, wherein the solvent further comprises a propylene glycol monomethyl ether.

13. The photosensitive composition according to claim 1, which is exposed with X-rays, electron beams or EUV.

14. A pattern forming method comprising:
a process of forming a photosensitive film with the photosensitive composition according to claim 1;
a process of exposing the photosensitive film; and
a process of developing the photosensitive film.

15. The photosensitive composition according to claim 1, wherein $X^-$ in formula (I) is a disulfonamide anion.

16. A compound represented by the following formula (I):

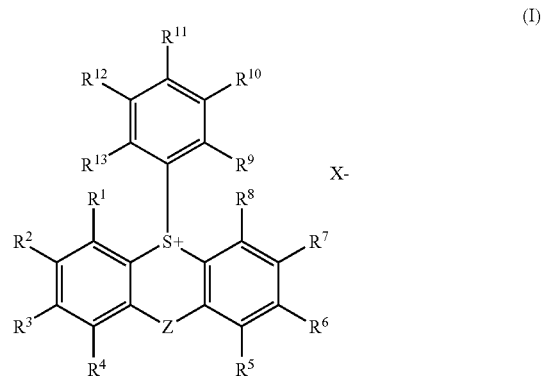

wherein
$R^1$ to $R^{13}$ each independently represents a hydrogen atom or a substituent;
Z represents a single bond, an alkylene group, an arylene group, an ether group or a thioether group;
$X^-$ represents an anion containing a proton acceptor functional group; and
the proton acceptor functional group is a functional group having a basicity selected from the group consisting of an amino group, an anilino group, a pyridine group, an amidino group and a guanidino group.

* * * * *